United States Patent [19]
Kobayashi et al.

[11] Patent Number: 6,057,337
[45] Date of Patent: May 2, 2000

[54] 1,2-DI-SUBSTITUTED PIPERIDINE DERIVATIVE, HAIR GROWTH PROMOTER AND EXTERNAL COMPOSITION FOR SKIN USING THE SAME

[75] Inventors: Koji Kobayashi; Hirotada Fukunishi; Kenichi Umishio; Akihiro Ishino, all of Kanagawa, Japan

[73] Assignee: Shiseido Co., Ltd., Tokyo, Japan

[21] Appl. No.: 09/239,960

[22] Filed: Jan. 29, 1999

[30] Foreign Application Priority Data

Feb. 2, 1998 [JP] Japan ................................. 10-035454

[51] Int. Cl.[7] ........................... C07D 211/22; A61K 7/06
[52] U.S. Cl. ....................... 514/316; 514/326; 514/330; 514/252; 514/235.5; 544/130; 544/160; 546/189; 546/275; 546/278; 546/281; 546/298; 546/301; 546/323; 546/321 N; 546/326
[58] Field of Search ................... 546/326, 281, 546/328, 298, 309, 373, 278, 275, 184; 544/130, 360; 514/316, 326, 330, 252, 235.5

[56] References Cited

U.S. PATENT DOCUMENTS

| | | | |
|---|---|---|---|
| 3,133,061 | 5/1964 | Kirchner | 260/247 |
| 3,332,949 | 7/1967 | Kirchner | 260/268 |
| 4,873,236 | 10/1989 | Engel | 514/220 |

FOREIGN PATENT DOCUMENTS

| | | | |
|---|---|---|---|
| 0 273 239 A1 | 7/1988 | European Pat. Off. | C07D 471/04 |
| 07304736 | 11/1995 | Japan | C07D 209/08 |
| 07316022 | 12/1995 | Japan | A61K 7/06 |
| 07316023 | 12/1995 | Japan | A61K 7/06 |
| 08020521 | 1/1996 | Japan | A61K 7/48 |
| 08026942 | 1/1996 | Japan | A61K 7/06 |
| 8-020521 | 1/1996 | Japan | C07D 213/89 |

OTHER PUBLICATIONS

Shapiro et al. "Antihypertensive Agents. I. Dialkylaminoalkoxyalkylpiperidines and Pyrrolidines," Journal of the American Chemical Society, vol. 80, 1958, pp. 2743–2745, Jun.

Werbel et al. "N–Momno–and N,N–Dialkyl–N'–1–naphthylalkylenediamines," Journal of Medicinal Chemistry, vol. 6, No. 6, 1963 pp. 637–646, Nov.

Primary Examiner—Robert Gerstl
Attorney, Agent, or Firm—Snider & Associates; Ronald R. Snider

[57] ABSTRACT

A 1,2-di-substituted piperidine derivative or a salt thereof expressed by the following Formula (I):

$$R^4 \text{—piperidine—} (Y)_l\text{—A}, (CH_2)_{\overline{m}}\text{—Z—B} \quad (I)$$

wherein one of A and B is a hydrocarbon group of $C_{1-30}$ expressed by $R^1$ and the other is $-(CH_2)n-NR^2R^3$; Y is $-CO-$, $-CONR^5-$ or $-COO-$; Z is $-O-$, $-OCO-$, $-OCONR^6-$ or $-NR^6-$; $R^2$ and $R^3$ individually represent a hydrogen a lower alkyl, a phenyl or a benzyl group, or together represent a heterocycle having 3–7 members; $-NR^5-(CH_2)n-NR^2R^3$ and $-NR^6-(CH_2)n-NR^2R^3$ of $-(Y)_l-A$ and $-Z-B$ may be the following Group W:

$$-N\underset{E}{\overset{}{\frown}}N-R^2 \quad (W)$$

wherein ring E is a heterocycle of 6 or 7 members including two nitrogen atoms and $R^2$ is a hydrogen, a lower alkyl, a phenyl or a benzyl group; $R^4$ is a hydrogen, a halogen, a lower alkyl, a lower acyl, a nitro, a cyano, a lower alkoxycarbonyl, a carbamoyl, a lower alkylcarbamoyl, a lower alkylamino, a lower acylamino, a lower alkoxy or a lower acyloxy group; each of $R^5$ and $R^6$ is a hydrogen, a lower alkyl, a lower acyl, a lower alkylcarbamoyl group, or a part of said ring E; l is 0 or 1; m is an integer of 2–5; and n is an integer of 0–5. The 1,2-di-substituted piperidine derivative or the salt thereof has excellent hair growth and regrowth promoting effects, which are useful for care, improvement or prevention of hair loss in mammals and, in particular, in human.

18 Claims, 49 Drawing Sheets

Fig. 1 Reaction Formula AA

Reaction Formula AB

Reaction Formula AC

Reaction Formula AD

Reaction Formula AE

Reaction Formula AF

Reaction Formula AG

Reaction Formula AH

Fig. 9 Reaction Formula AI

Reaction Formula BA

Reaction Formula BB

Reaction Formula BC

Reaction Formula BD

Reaction Formula BE

Fig. 15
Reaction Formula CA
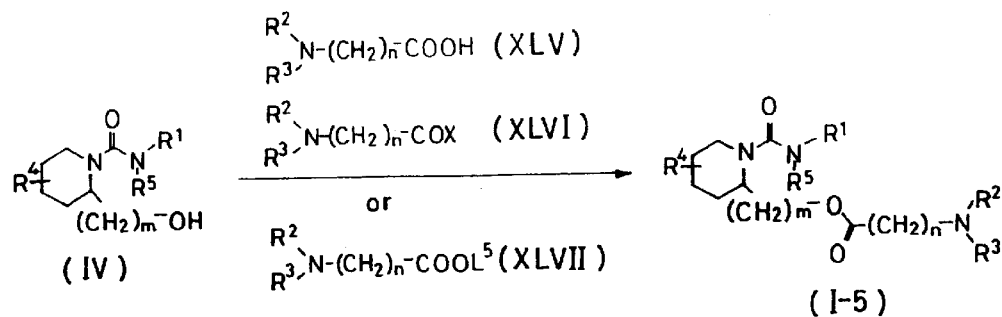
Fig. 16
Reaction Formula CB
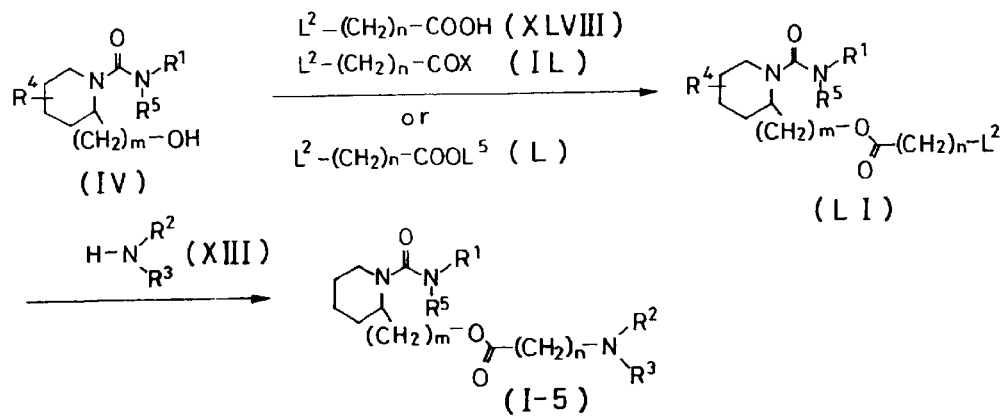
Fig. 17
Reaction Formula CC
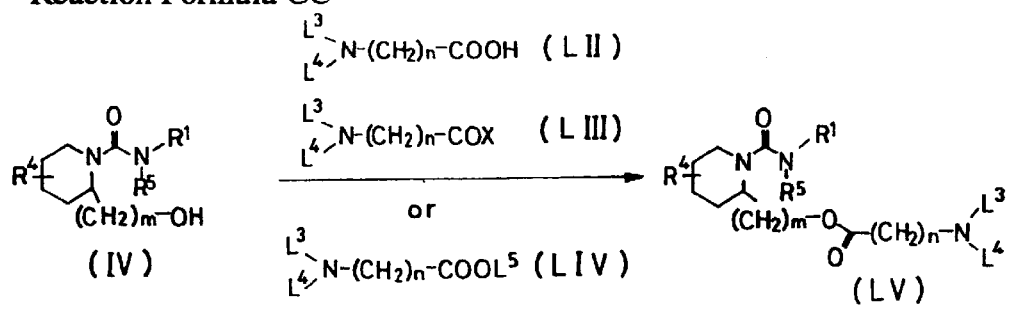
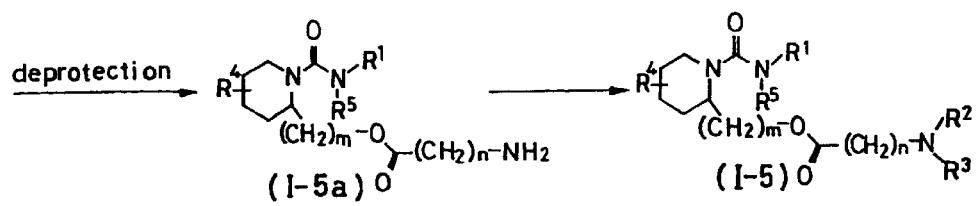

Fig. 18
Reaction Formula CD
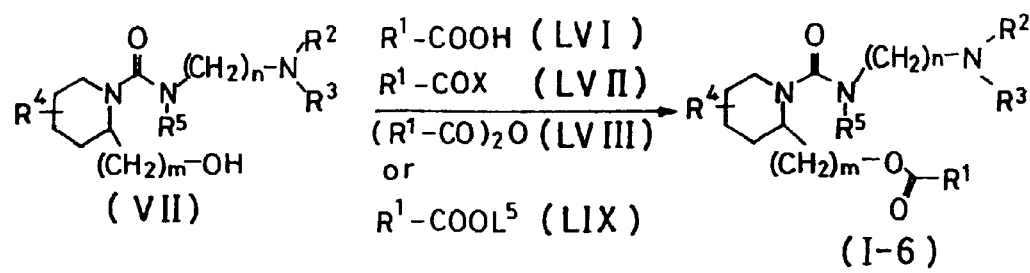
Fig. 19
Reaction Formula CE
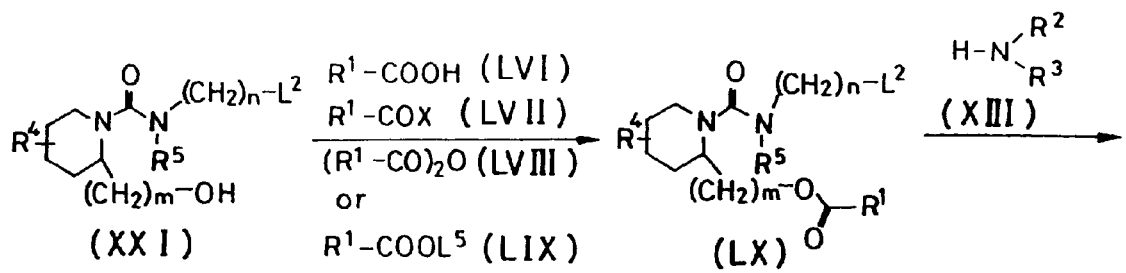
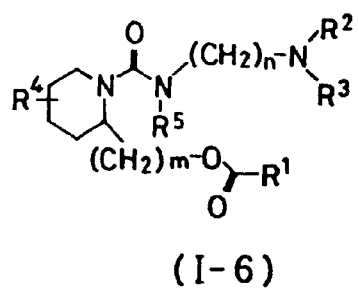
(I-6)

Reaction Formula CF

Reaction Formula CG

Reaction Formula DA

Reaction Formula DB

Fig. 24
Reaction Formula DC
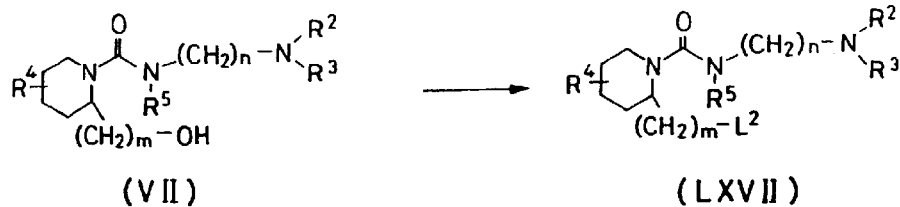
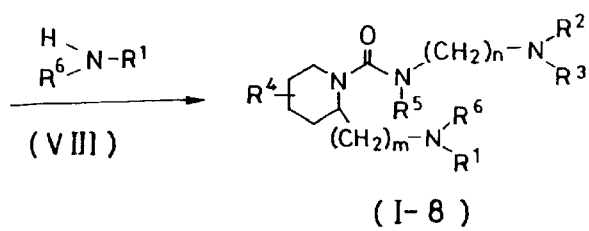
Fig. 25
Reaction Formula DD
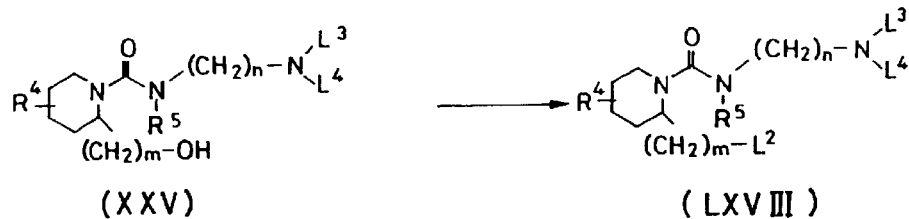
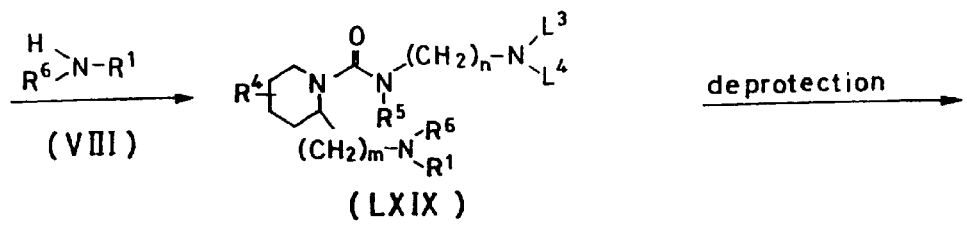
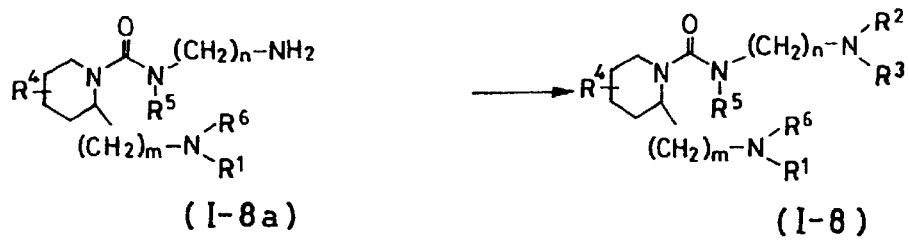

Reaction Formula DE

Reaction Formula EA

Reaction Formula EB

Reaction Formula EC

Reaction Formula ED

Reaction Formula EE

Reaction Formula EF

Reaction Formula EG

Fig. 34
Reaction Formula FA
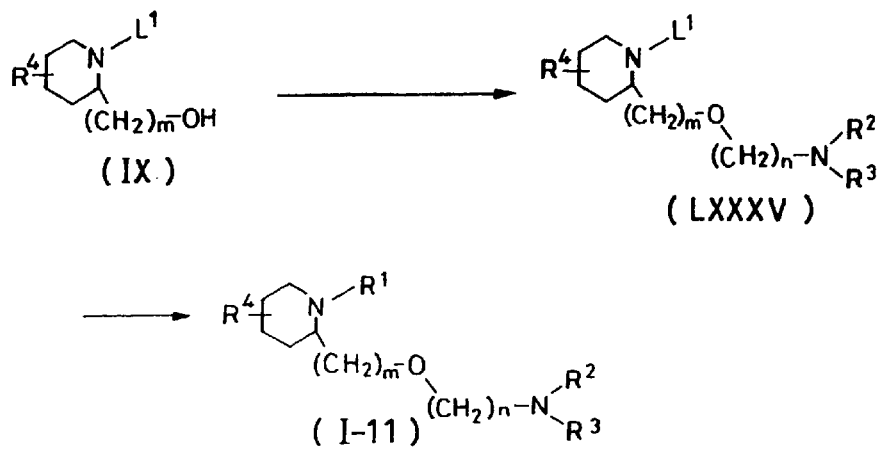
Fig. 35
Reaction Formula FB
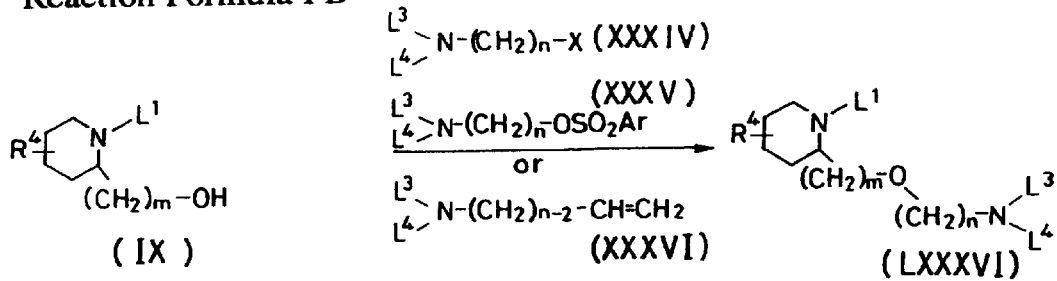
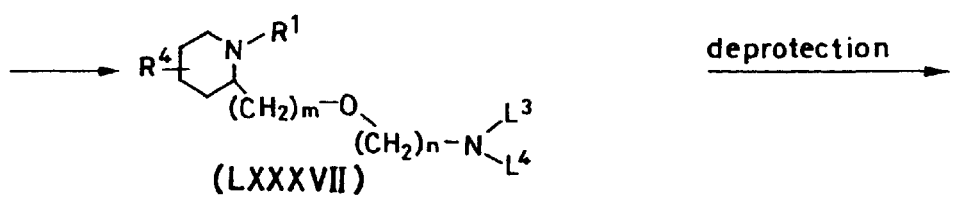
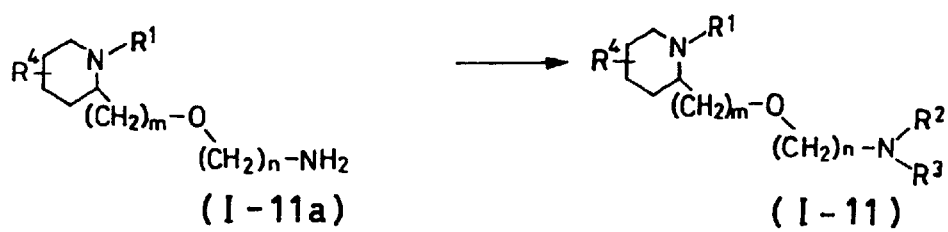

Reaction Formula FC

Reaction Formula GA

Reaction Formula GB

Reaction Formula GC

Fig. 40
Reaction Formula GD
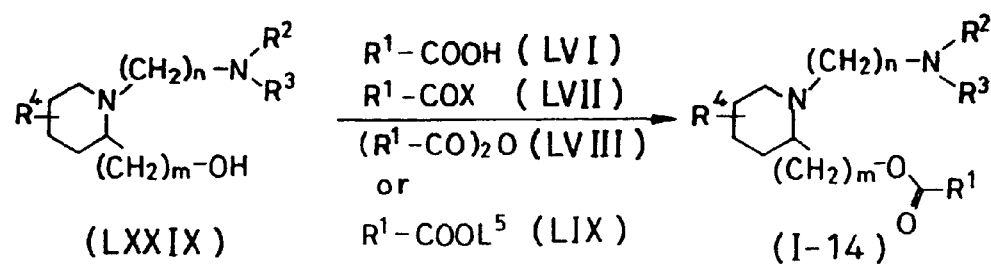
Fig. 41
Reaction Formula GE
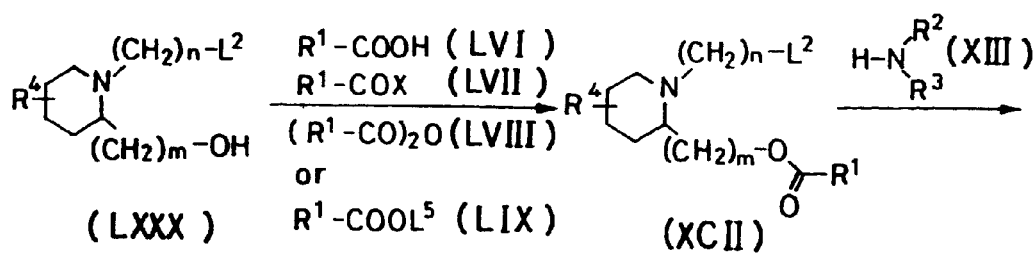
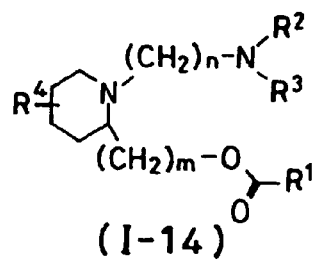

Reaction Formula GF

Reaction Formula GG

Fig. 44
Reaction Formula HA
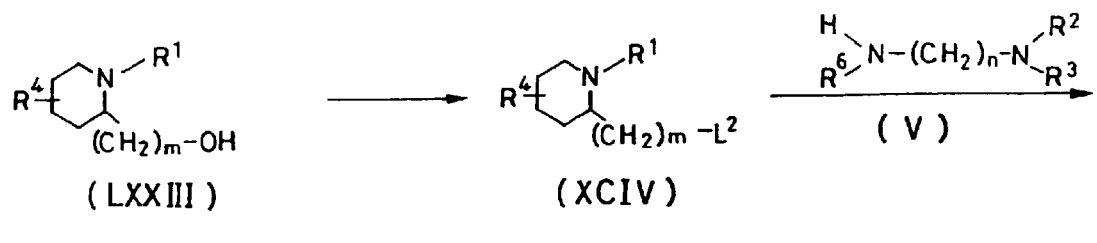
(LXXIII)   (XCIV)
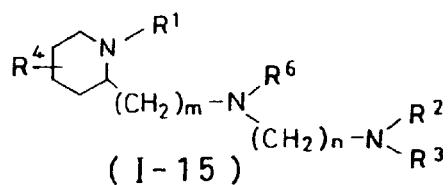
(I-15)
Fig. 45
Reaction Formula HB
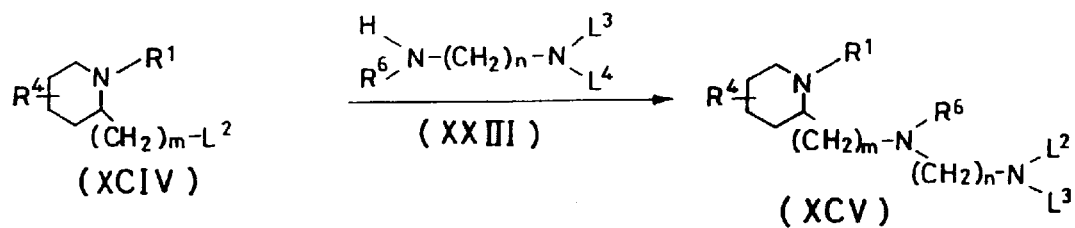
(XCIV)   (XCV)
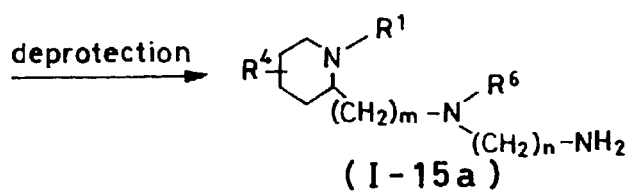
(I-15a)
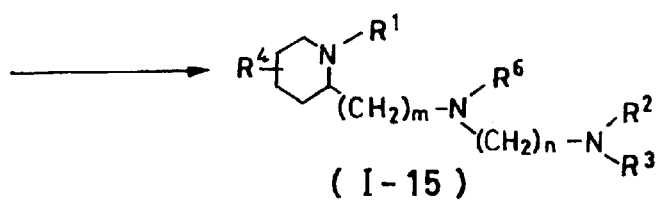
(I-15)

Reaction Formula HC

Reaction Formula HD

Reaction Formula HE

Reaction Formula IA

Reaction Formula IB

Reaction Formula IC

Reaction Formula ID

Reaction Formula IE

Reaction Formula IF

Reaction Formula IG

Reaction Formula JA

Reaction Formula JB

Reaction Formula JC

Reaction Formula JD

Reaction Formula JE

Fig. 61
Reaction Formula KA
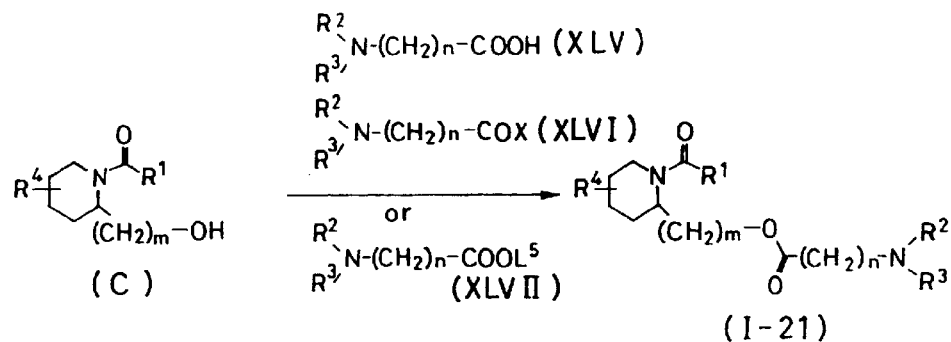
Fig. 62
Reaction Formula KB
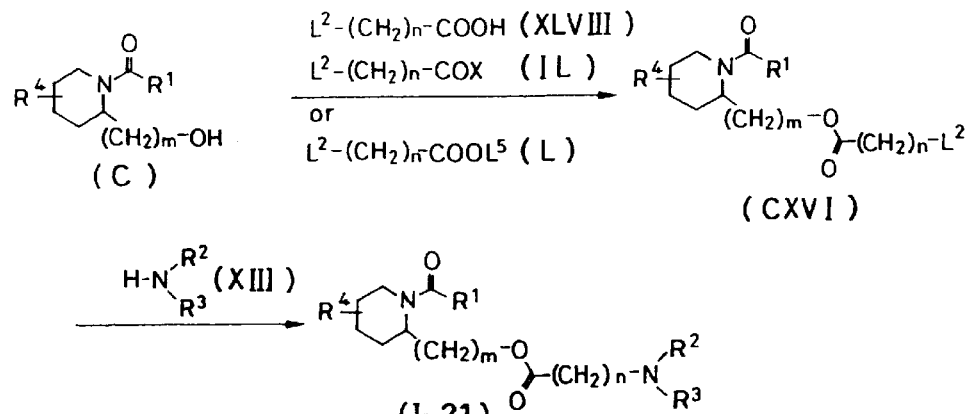
Fig. 63
Reaction Formula KC
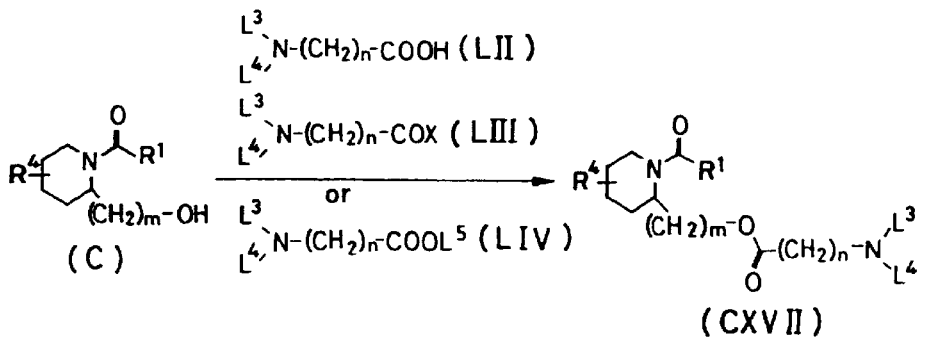
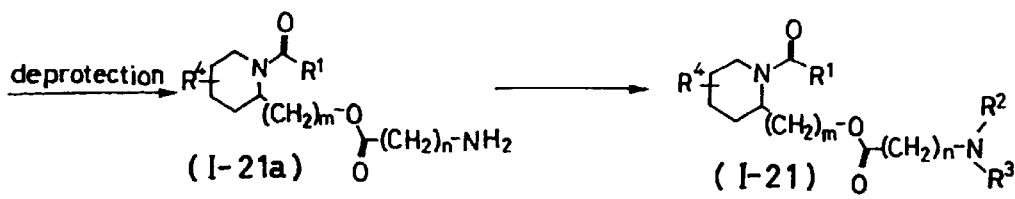

Fig. 64
Reaction Formula KD
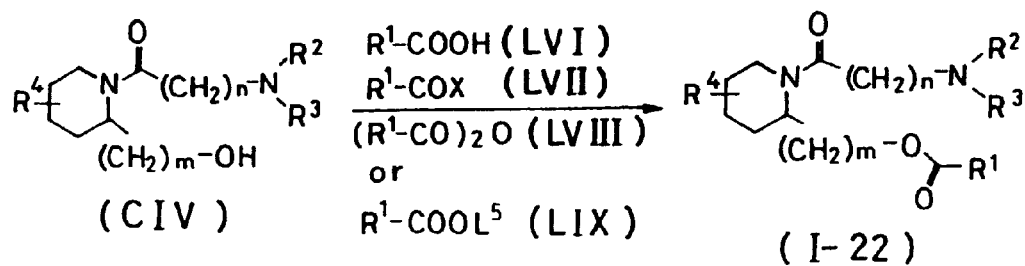
Fig. 65
Reaction Formula KE
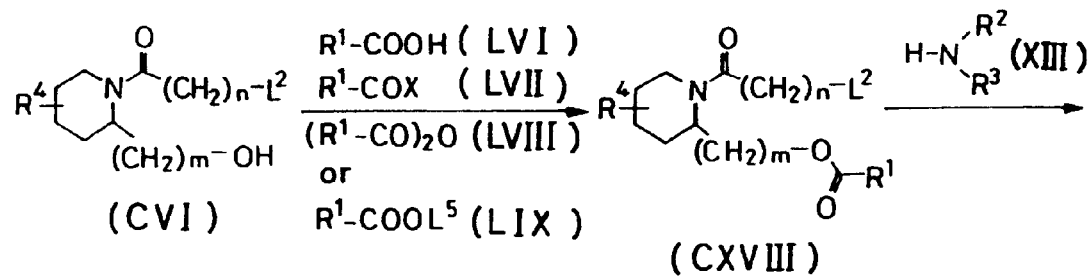
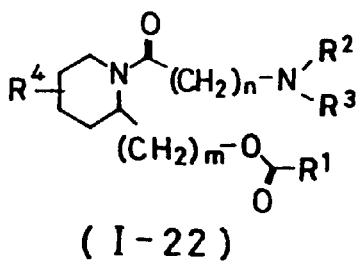
( I-22 )

Reaction Formula KF

Reaction Formula KG

Reaction Formula LA

Reaction Formula LB

Fig. 70
Reaction Formula LC
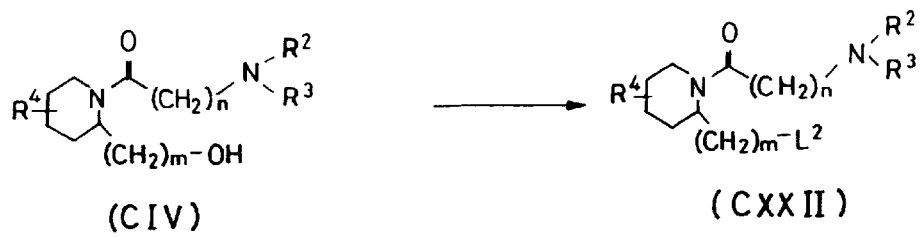
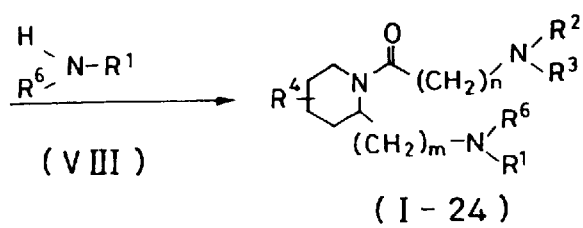
Fig. 71
Reaction Formula LD
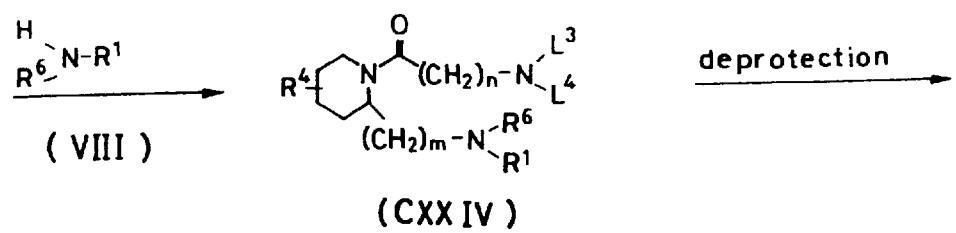
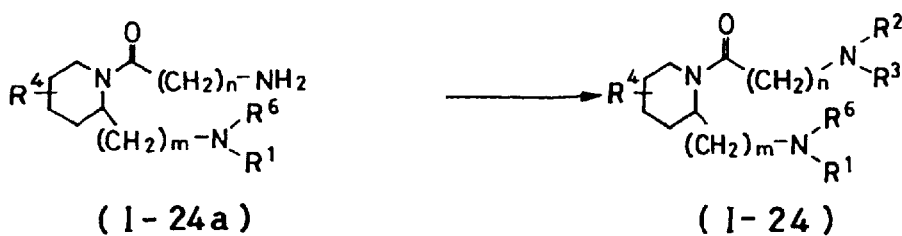

Fig. 72
Reaction Formula LE
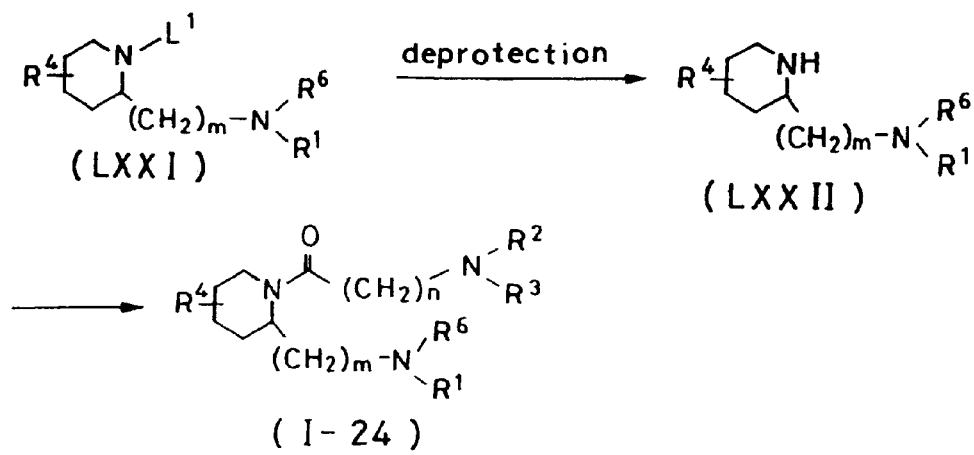
Fig. 73
Reaction Formula MA
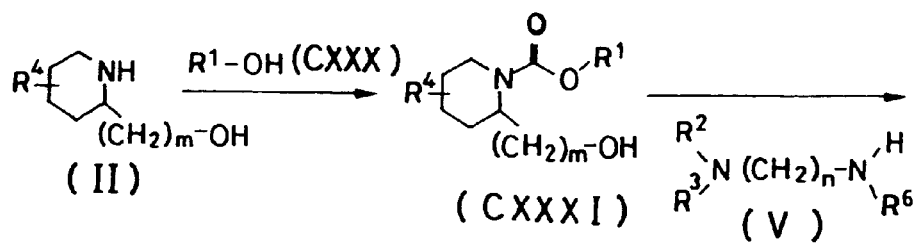
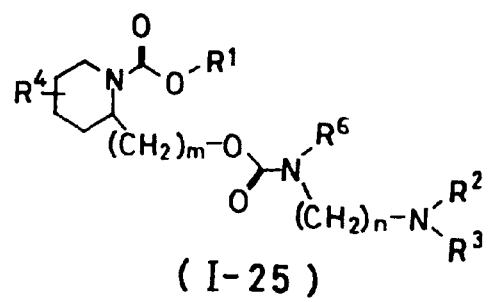

Reaction Formula MB

Reaction Formula MC

Fig. 76
Reaction Formula MD
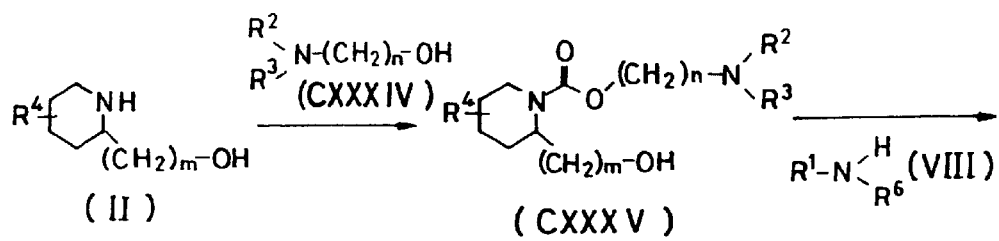
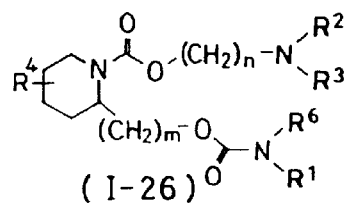
Fig. 77
Reaction Formula ME
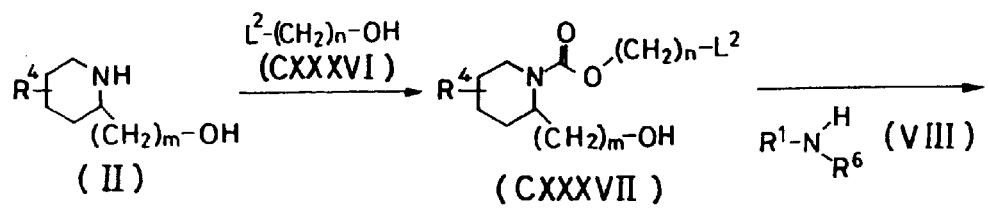
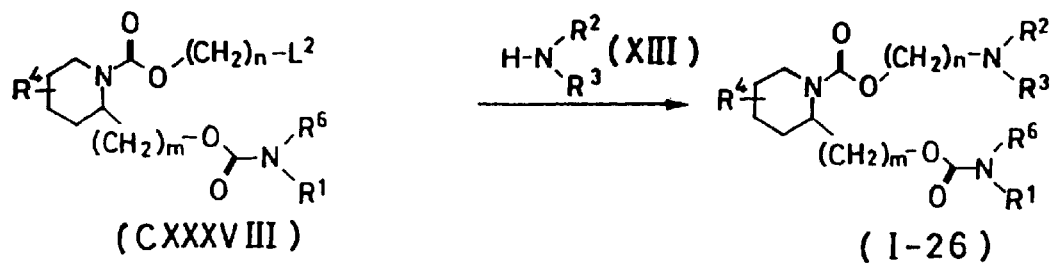

Reaction Formula MF

Reaction Formula MG

Reaction Formula NA

Reaction Formula NB

Reaction Formula NC

Reaction Formula ND

Reaction Formula NE

Reaction Formula OA

Reaction Formula OB

Reaction Formula OC

Reaction Formula OD

Reaction Formula OE

Reaction Formula OF

Reaction Formula OG

Fig. 92
Reaction Formula PA
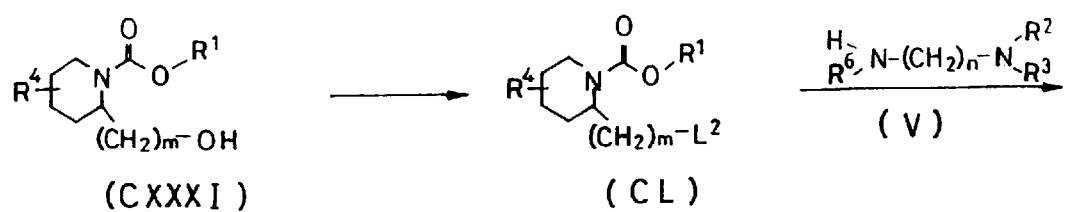
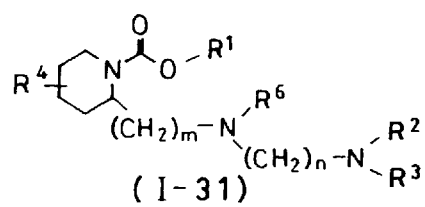
Fig. 93
Reaction Formula PB
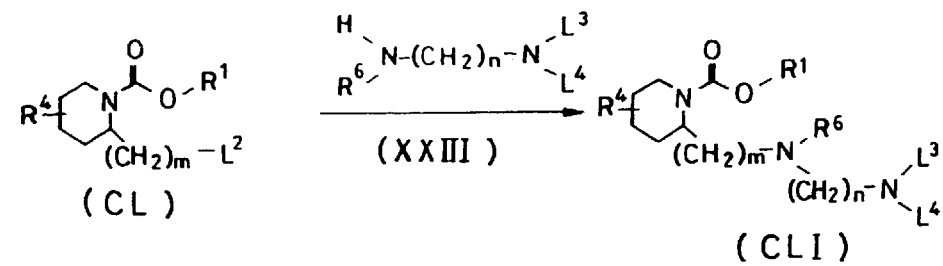
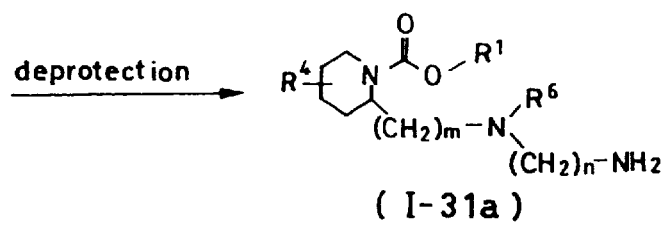
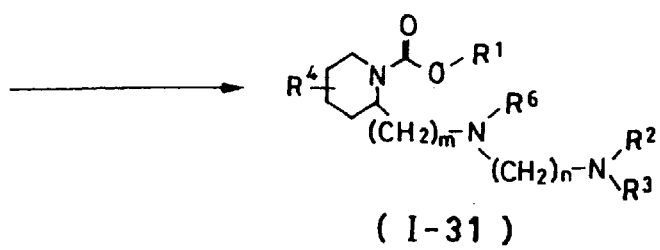

Reaction Formula PC

Reaction Formula PD

Reaction Formula PE

1,2-DI-SUBSTITUTED PIPERIDINE DERIVATIVE, HAIR GROWTH PROMOTER AND EXTERNAL COMPOSITION FOR SKIN USING THE SAME

RELATED APPLICATIONS

This application claims the priority of Japanese Patent Application No. 10-35454 filed on Feb. 2, 1998, which is incorporated herein by reference.

FIELD OF THE INVENTION

The present invention relates to a 1,2-di-substituted piperidine derivative and, in particular, to a 1,2-di-substituted piperidine derivative that has excellent hair growth effect.

BACKGROUND OF THE INVENTION

At the present time, scalp abnormality due to activation of androgen in an organ such as hair root or sebaceous gland, lowering of blood stream toward hair follicle, excess secretion of sebum, generation of peroxide and the like has been considered as a cause of baldness or hair loss. Accordingly, a compound or composition that can remove or reduce the above-mentioned problems has been generally included into a hair growth promoting composition to promote hair growth and regrowth and to prevent hair loss, for a long time (in the present invention, "hair growth promoting composition" includes hair regrowth promoting composition, and the like).

At present, compounds or crude drug extracts having various functions have been compounded to the hair growth promoting composition. These functions include blood flow promoting action, topical stimulation, hair follicle activating action, antiandrogen action, antiseborrheic action and the like have been known. Examples of drugs having blood flow promoting action include swertia herb extract, vitamin E and its derivative, and benzyl nicotinate. Examples of drugs which promote blood circulation by topical stimulation include capsicum tincture, cantharides tincture, camphor and vanillic acid nonylamide. Examples of drugs having hair follicle activating action include hinokitiol, placental extract, photosensitizing dye, pantothenic acid and derivative thereof. Examples of drugs having antiandrogen action include estradiol and estrone. Examples of drugs having antiseborrheic action include sulfur, thioxolone and vitamin $B_6$.

In addition to these drugs, salicylic acid, resorcine and the like that have corneocyte desquamating action and antibacterial action can be compounded to hair growth promoting composition for the purpose of preventing dandruff. Further, glycyrrhizic acid, menthol and the like can be compounded in order to prevent inflammation of scalp. Furthermore, amino acids, vitamins, extracts of crude drugs and the like can be compounded so as to aliment to hair follicle and activate enzyme activity.

Meanwhile, for example, D (L)-pantolactone (Unexamined Japanese Patent Publication No. Hei 8-26942), 2(1H)-pyridone derivative (Unexamined Japanese Patent Publication No. Hei 8-20521), $N^G$-nitro-L-arginine (Unexamined Japanese Patent Publication No. Hei 7-316023), 3-methyleneisoindolin-1-one derivative (Unexamined Japanese Patent Publication No. Hei 7-316022), indole derivative (Unexamined Japanese Patent Publication No. Hei 7-304736) are disclosed in recent patents as drugs having hair regrowth effect, hair growth effect, and hair loss protecting effect.

However, although the drugs described above are compounded to the conventional hair growth promoting compositions, they do not always exhibit sufficient hair regrowth and growth promoting effect.

SUMMARY OF THE INVENTION

In view of the foregoing problem in the prior art, an object of the present invention is to provide a compound, which is excellent in hair growth and regrowth promoting effect on human hair, and a hair growth promoting composition comprising the same as an active ingredient.

As a result of diligent studies of the inventors for attaining the above mentioned objects, it has been found that certain 1,2-di-substituted piperidine derivative and its salt have excellent hair growth and regrowth promoting effect, thereby accomplishing the present invention.

Namely, a 1,2-di-substituted piperidine derivative or a salt thereof in accordance with the present invention is expressed by the following Formula (I):

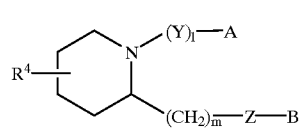

(I)

wherein each of A and B is $R^1$ or —$(CH_2)n$-$NR^2R^3$, wherein when A is $R^1$, B is —$(CH_2)n$-$NR^2R^3$ and when A is —$(CH_2)n$-$NR^2R^3$, B is $R^1$;

Y is —CO—, —$CONR^5$— or —COO—;

Z is —O—, —OCO—, —$OCONR^6$— or —$NR^6$—;

$R^1$ is a hydrocarbon group of $C_{1-30}$;

$R^2$ and $R^3$ individually represent a hydrogen atom, a lower alkyl group, a phenyl group or a benzyl group, or together represent a heterocycle having 3–7 members;

when —$(Y)_l$—A is —$CONR^5$—$(CH_2)n$-$NR_2R^3$ and when —Z—B is —$OCONR^6$—$(CH_2)n$-$NR^2R^3$ or —$NR^6$—$(CH_2)n$-$NR^2R^3$, —$NR^5$—$(CH_2)n$-$NR^2R^3$ and —$NR^6$—$(CH_2)n$-$NR^2R^3$ of —$(Y)_l$—A and —Z—B may be the following Group W:

(W)

wherein ring E is a heterocycle of 6 or 7 members including two nitrogen atoms and $R^2$ is a hydrogen atom, a lower alkyl group, a phenyl group or a benzyl group;

$R^4$ is selected from the group consisting of a hydrogen atom, a halogen atom, a lower alkyl group, a lower acyl group, a nitro group, a cyano group, a lower alkoxycarbonyl group, a carbamoyl group, a lower alkylcarbamoyl group, a lower alkylamino group, a lower acylamino group, a lower alkoxy group and a lower acyloxy group;

$R^5$ is a hydrogen atom, a lower alkyl group, a lower acyl group or a lower alkylcarbamoyl group; when —$(Y)_l$—A is —$CONR^5$—$(CH_2)n$-$NR^2R^3$, —$(Y)_l$—A may be —CO—W;

$R^6$ is a hydrogen atom, a lower alkyl group, a lower acyl group or a lower alkylcarbamoyl group; when —Z—B is —$OCONR^6$—$(CH_2)n$-$NR^2R^3$ or —$NR^6$—$(CH_2)n$-$NR^2R^3$, —Z—B may be —OCO—W or said Group W;

l is 0 or 1;

m is an integer of 2–5; and n is an integer of 0–5.

A hair growth promoting composition in accordance with the present invention is characterized by comprising said 1,2-di-substituted piperidine derivative or the pharmacologically acceptable salt thereof as an effective ingredient.

An external preparation for skin in accordance with the present invention is characterized by comprising said 1,2-di-substituted piperidine derivative or the pharmacologically acceptable salt thereof.

A method for promoting hair growth in accordance with the present invention is characterized by applying an effective amount of said 1,2-di-substituted piperidine derivative or the pharmacologically acceptable salt thereof on the skin of mammals and, in particular, on human scalp.

BEST MODE FOR CARRYING OUT THE INVENTION

Figure 1:
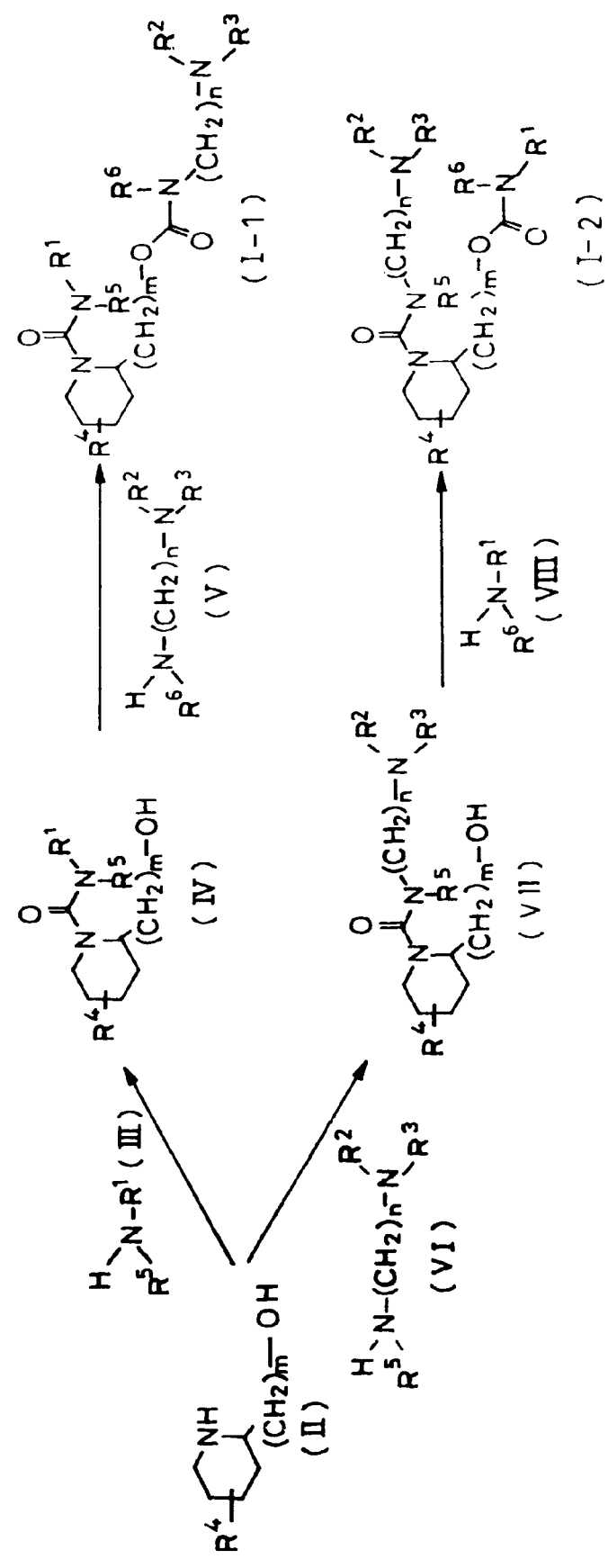
FIGS. 1–96 show examples of steps for manufacturing the 1,2-di-substituted piperidine derivative in accordance with the present invention.

In a compound of the present invention, a hydrocarbon group of $C_{1-30}$ shown by $R^1$ refers to a straight or branched alkyl group having 1–30 carbon atoms, a straight or branched alkenyl group having 2–30 carbon atoms or a straight or branched alkynyl group having 2–30 carbon atoms and may have a saturated ring or aromatic ring in $R^1$.

Examples of the above-mentioned straight alkyl group include methyl, ethyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, henicosyl, docosyl, tetracosyl, hexacosyl octacosyl and the like.

Examples of the above-mentioned branched alkyl group include isopropyl, isobutyl, sec-butyl, tert-butyl, 2-methylpentyl, 3-metylpentyl, 4-methylpentyl, 4-ethylpentyl, 6-methyldecyl, 9-methyldecyl, 6-ethylnonyl, 5-propyloctyl, 11-methyldodecyl, 12-methyltridecyl, 4-methyltetradecyl, 13-methyltetradecyl, 14-ethylhexadecyl, 10-methyloctadecyl, 15-ethylheptadecyl, 10-methyldococyl, 2-pentyloctadecyl, 22-methyltricosyl, 12-hexyloctadecyl, 6-methyltetracosyl, 24-methylheptacosyl, 2-decylhexadecyl, 2-nonyloctadecyl, 2-dodecyloctadecyl and the like.

Examples of the straight or branched alkenyl group having 2–30 carbon atoms and straight or branched alkynyl group having 2–30 carbon atoms include the alkenyl or alkynyl groups corresponding to the above-mentioned alkyl groups such as 3-octenyl, 2-nonenyl, 3-hexynyl, 4-decenyl, 7-dodecenyl, 9-octadodecenyl or 3-dodecynyl.

Also, examples of the hydrocarbon group having a saturated ring or an aromatic ring in $R^1$ include cyclohexyl, 12-cyclohexyldodecyl, phenyl, 4-butylphenyl, 2-phenylethyl, 8-phenyloctyl, biphenylyl, and the like.

Among these groups, $R^1$ is preferably a straight or branched alkyl group having 10–30 carbon atoms and, more preferably, a straight or branched alkyl group having 10–21 carbon atoms and, particularly preferably, octadecyl group. Also, when —(Y)$_1$—A is —O—$R^1$, or when —Z—B is —OCO—$R^1$, $R^1$ is preferably heptadecyl or henicosyl group. The hair growth effect tends to deteriorate in the case where the carbon number of $R^1$ is too small.

Each of $R^2$ and $R^3$, which may be identical or different from each other, can be a hydrogen, a lower alkyl, a phenyl or a benzyl group. Also, $R^2$ and $R^3$ together can represent a heterocycle having 3–7 members. Further, when —(Y)$_1$—A is —CONR$^5$—(CH$_2$)n-NR$^2$R$^3$ and when —Z—B is —OCONR$^6$—(CH$_2$)n-NR$^2$R$^3$ or —NR$^6$—(CH$_2$)n-NR$^2$R$^3$, —NR$^5$—(CH$_2$)n-NR$^2$R$^3$ and —NR$^6$—(CH$_2$)n-NR$^2$R$^3$ of —(Y)$_1$—A and —Z—B may be said Group W.

In $R^2$ and $R^3$, the lower alkyl group refers to a straight or branched alkyl group having 1–6 carbon atoms. Examples of the lower alkyl group include methyl, ethyl, propyl, butyl, isopropyl, isobutyl, 1-methylpropyl, tert-butyl, pentyl, 1-ethylpropyl, isoamyl, hexyl and the like. For the lower alkyl group in $R^2$ and $R^3$, methyl or ethyl group is preferable. In the present invention, the definition of lower alkyl group is the same as mentioned above if there is no further description.

Also, the lower alkyl group in $R^2$ and $R^3$ may be substituted by a hydroxyl group. Examples of such a hydroxy lower alkyl group include 2-hydroxyethyl group.

In $R^2$ and $R^3$, a phenyl and a benzyl group may be unsubstituted or substituted by a halogen, a lower alkyl, a lower acyl, a nitro, a cyano, a lower alkoxycarbonyl, a lower alkylamino, a lower alkoxy or a lower acyloxy group, respectively. The definition of each substituent referred in here is explained as follows:

The halogen atom represents chlorine, bromine, iodine or fluorine.

The lower alkyl group is as mentioned above and, preferably, methyl or ethyl group.

The lower acyl group is a straight or branched acyl group having 2–7 carbon atoms. Examples of the lower acyl group include acetyl, propionyl, butyryl, isobutyryl, pivaloyl, benzoyl group and the like.

The lower alkoxycarbonyl group represents a carboxyl group whose hydrogen atom is substituted by a lower alkyl group. A preferable example of the lower alkoxycarbonyl group is methoxycarbonyl or ethoxycarbonyl group.

The lower alkylamino group represents an amino group whose hydrogen atom is substituted by one or two of the same or different lower alkyl group. A preferable example of the lower alkylamino group is methylamino or dimethylamino group.

The lower alkoxy group represents a hydroxyl group whose hydrogen atom is substituted by a lower alkyl group. A preferable example of the lower alkoxy group is methoxy or ethoxy group.

The lower acyloxy group represents a hydroxyl group whose hydrogen atom is substituted by a lower acyl group, wherein said lower acyl group is as above-mentioned. A preferable example of the lower acyloxy group is acetoxy or propionyloxy group.

In $R^2$ and $R^3$, the heterocycle having 3–7 members which is formed by $R^2$ and $R^3$ together represents a saturated or unsaturated heterocycle having 3–7 members containing nitrogen atom to which $R^2$ and $R^3$ are bonded. In addition to the nitrogen atom, a hetero atom such as nitrogen atom or oxygen atom may be contained in the heterocycle. Examples of the heterocycle include aziridine, azetidine, pyrrolidine, piperidine, homopiperidine, piperazine, morpholine, pyrrole, pyrazole, and imidazole ring. Among these heterocycles, pyrrolidine, piperidine, piperazine or morpholine ring is preferable. The heterocycle may be substituted by one or two of the same or different substituent. Such a substituent can be selected from the group consisting of a lower alkyl, a lower alkoxy, a lower acyl and a nitro group. The lower alkyl group is preferably methyl or ethyl group. The lower alkoxy group is preferably methoxy or ethoxy group. The lower acyl group is preferably acetyl or propionyl group.

In said Group W, the heterocyclic ring E having 6–7 members can be formed by $R^3$ together with $R^5$ or $R^6$ to contain two nitrogen atoms. R in Group W can be a hydrogen, a lower alkyl, a phenyl or a benzyl group and, preferably, methyl or benzyl group. As for the heterocyclic ring E, a piperazine ring is preferable.

In the present invention, it is preferable that $R^2$ and $R^3$ are lower alkyl groups, or together forms a heterocycle having 3–7 members or a part of Group W.

$R^4$ can be a hydrogen atom, a halogen atom, a lower alkyl group, a lower acyl group, a nitro group, a cyano group, a lower alkoxycarbonyl group, a carbamoyl group, a lower alkylcarbamoyl group, a lower alkylamino group, a lower acylamino group, a lower alkoxy group or a lower acyloxy group.

As for $R^4$, the definitions for halogen, lower alkyl, lower acyl, lower alkoxycarbonyl, lower alkylamino, lower alkoxy and lower acyloxy groups are identical to those in $R^2$ and $R^3$.

The lower alkylcarbamoyl group in $R^4$ represents a carbamoyl group whose one or two hydrogen atoms are substituted by a lower alkyl group. A preferable example of the lower alkylcarbamoyl group is methylcarbamoyl or ethylcarbamoyl group.

The lower acylamino group in $R^4$ represents an amino group whose one or two hydrogen atoms are substituted by a lower acyl group. The lower acyl group is as mentioned above. A preferable example of the lower acylamino group is acetylamino, propionylamino or benzoylamino group.

Preferably, $R^4$ is a hydrogen atom.

$R^5$ can be a hydrogen atom, a lower alkyl group, a lower acyl group or a lower alkylcarbamoyl group. Also, when $-(Y)_1-A$ is $CONR^5-(CH_2)n-NR^2R^3$, $-(Y)_1-A$ may be $-CO-W$. Preferably, $R^5$ is a hydrogen atom.

$R^6$ can be a hydrogen atom, a lower alkyl group, a lower acyl group or a lower alkylcarbamoyl group. Also, when $-Z-B$ is $-OCONR^6-(CH_2)n-NR^2R^3$ or $-NR^6-(CH_2)n-NR^2R^3$, $-Z-B$ may be $-OCO-W$ or Group W. Preferably, $R^6$ is a hydrogen atom or forms a part of Group W.

As for $R^5$ and $R^6$, the definitions for lower alkyl and lower acyl groups are identical to those in $R^2$ and $R^3$ and the definition for lower alkylcarbamoyl group is identical to that in $R^4$.

Y is a divalent group expressed by $-CO-$, $-CONR^5-$ or $-COO-$.

Z is a divalent group expressed by $-O-$, $-OCO-$, $-OCONR^6-$ or $-NR^6-$ and, preferably, $-OCONR^6-$.

In the present invention, l is 0 or 1.

Also, m is an integer of 2–5 and, preferably, 2.

Further, n is an integer of 0–5 and, preferably, an integer of 2–5 and, more preferably, 2 or 3.

In the present invention, a preferable compound having Group W may be expressed by the following Formula (IA):

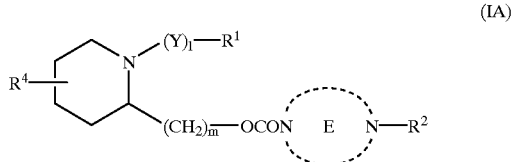

(IA)

wherein ring E is a heterocycle of 6 or 7 members including two nitrogen atoms;

$R^1$ is a hydrocarbon group of $C_{1-30}$;
$R^2$ is a hydrogen atom, a lower alkyl group, a phenyl group or a benzyl group;
$R^4$ is selected from the group consisting of a hydrogen atom, a halogen atom, a lower alkyl group, a lower acyl group, a nitro group, a cyano group, a lower alkoxycarbonyl group, a carbamoyl group, a lower alkylcarbamoyl group, a lower alkylamino group, a lower acylamino group, a lower alkoxy group and a lower acyloxy group;
Y is $-CO-$, $-CONR^5-$ or $-COO-$;
l is 0 or 1; and
m is an integer of 2–5.

In Formula (IA), it is preferable that l is 1 and Y is $-CO-$.

The Compound(I) of the present invention may have a conformational isomer because of having a piperidine ring. Also, there may be the other isomers such as optical isomers based on an asymmetric carbon or geometrical isomers. The present invention can comprise any isomers and the mixture thereof.

The Compound (I) provided in the present invention can be manufactured by using well-known reactions. Although the representative synthetic examples will be shown in the following, the present invention should not be restricted thereto. Also, in the following manufacturing methods, $R^1$, $R^2$, $R^3$, $R^4$, $R^5$, $R^6$, l, m and n are the same as shown in the definitions of Formula (I), unless otherwise indicated.

Compounds (I-1) and (I-2) (l=1, Y=$-CONR^5-$, Z=$-OCONR^6-$)

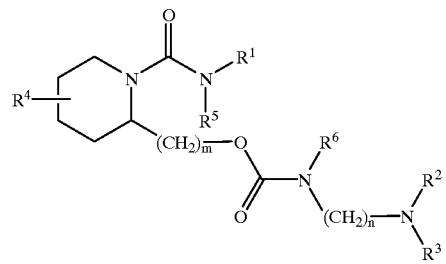

(I-1)

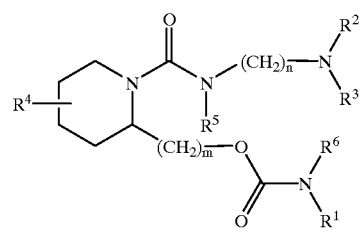

(I-2)

Compounds (I-1) and (I-2), for example, can be manufactured according to Reaction Formulae AA to AE of FIGS. 1 to 5.

Although in Reaction Formulae AA to AE, $R^2$ and $R^3$ are defined as in the above-mentioned Formula (I), it is preferable to manufacture Compounds (I-1) and (I-2) by using the following synthetic method according to the kind thereof.

It is preferable to manufacture them according to Reaction Formula AA, AB, AC or AE in the case where $R^2$ and $R^3$ each is a lower alkyl or benzyl group.

It is preferable to manufacture them according to Reaction Formula AA, AB, AC or AE in the case where either $R^2$ or $R^3$ is a lower alkyl or benzyl group while the other is a lower acyl or phenyl group.

It is preferable to manufacture them according to Reaction Formula AC or AE in the case where either $R^2$ or $R^3$ is a lower alkyl or benzyl group while the other is a hydrogen atom.

It is preferable to manufacture them according to Reaction Formula AA, AB or AC in the case where both $R^2$ and $R^3$ are lower acyl groups or phenyl groups.

It is preferable to manufacture them according to Reaction Formula AA, AB, AC or AE in the case where either $R^2$ or $R^3$ is a lower acyl group while the other is a phenyl group.

It is preferable to manufacture them according to Reaction Formula AA, AB, AC or AE in the case where either $R^2$ or $R^3$ is a lower acyl group while the other is a hydrogen atom.

It is preferable to manufacture them according to Reaction Formula AC in the case where either $R^2$ or $R^3$ is a phenyl group while the other is a hydrogen atom.

It is preferable to manufacture them according to Reaction Formula AC or AD in the case where both $R^2$ and $R^3$ are hydrogen atoms.

It is preferable to manufacture them according to Reaction Formula AA, AB, AC or AE in the case where $R^2$ and $R^3$ together form a heterocyclic ring having 3–7 members. At the first step of Reaction Formula AA of FIG. 1, Compound (IV) can be obtained by reacting Compound (II) with amine (III). Compound (VII) can be obtained by reacting Compound (II) with amine (VI) as in the same way.

In this reaction, for example, after an amino group of Compound (II) is converted into its corresponding carbonate by using e.g., phenyl chlorocarbonate, phosgene, diphosgene, triphosgene, di-2-pyridylketone or the like, the carbonate is reacted with amine (III) or (VI). As an additive, a base such as triethylamine, N,N-diisopropylethylamine, pyridine or sodium carbonate can be used. As a solvent, for example, a halogenated hydrocarbon such as dichloromethane or chloroform; an aromatic hydrocarbon such as benzene, toluene or xylene; or an ether such as tetrahydrofuran or 1,4-dioxane can be used. While the reaction temperature and reaction time may be changed according to the starting materials and the reagents used, the reaction is usually effected at a temperature within the range of –15° C. to 200° C.

Specifically, for example, by using pyridine or N,N-diisopropylethylamine as an additive, Compound (II) is reacted with phenyl chlorocarbonate or triphosgene in a solvent such as chloroform or dichloromethane at a temperature within the range of –15° C. to room temperature. The resulting carbonate corresponding to Compound (II) is reacted with amine (III) or (VI) in the absence or the presence of a solvent such as chloroform or dichloromethane at a temperature within the range of room temperature to 100° C., thereby attaining the aimed object.

At the second step of Reaction Formula AA, Compound (I-1) can be obtained from Compound (IV) and amine (V). Also, Compound (I-2) can be obtained from Compound (VII) and amine (VIII). These reactions can be effected according to the first step of said Reaction Formula AA. Namely, after a hydroxyl group of Compound (IV) or (VII) is converted into its corresponding carbonate, the carbonate is reacted with amine (V) or (VIII).

In the reactions of the first and second steps of Reaction Formula AA, it is possible to synthesize by addition reaction with the isocyanate corresponding to each amine in the place of the reaction with amine (III), (VI), (V) or (VIII) in the case where $R^5$ and $R^6$ are hydrogen atoms. For example, the compound wherein $R^5=R^6=H$ in Compound (I-1) can be synthesized by adding isocyanate OCN—$R^1$ to Compound (II) and then by adding isocyanate OCN—$(CH_2)n$-$NR^2R^3$ to the resulting compound.

This addition reaction forms —NCONH— or —OCONH— by adding an isocyanate group to an amino or hydroxyl group. In this reaction, for example, an acid such as boron trifluoride, hydrochloric acid, aluminium chloride, dialkyltin dichloride or dialkyltin acetate or a base such as triethylamine, N,N-diisopropylethylamine, pyridine, N-methylmorpholine, N-methylpiperidine or sodium acetate can be used as an additive. As a solvent, for example, a halogenated hydrocarbon such as dichloromethane or chloroform; an aromatic hydrocarbon such as benzene, toluene or xylene; an ether such as tetrahydrofuran or 1,4-dioxane; or an amide such as N,N-dimethylformamide or N,N-dimethylacetamide can be used. While the reaction temperature and reaction time may be changed according to the starting materials and the reagents used, the reaction is usually effected at a temperature within the range of 0° C. to the reflux temperature of the solvent.

Such an isocyanate is commercially available or can be manufactured from its corresponding amine or carboxylic acid. For example, isocyanate OCN—$(CH_2)n$-$NR^2R^3$ can be synthesized from its corresponding amine $H_2N$—$(CH_2)n$-$NR^2R^3$ or its corresponding carboxylic acid $HO_2C$—$(CH_2)n$-$NR^2R^3$.

In the case where the isocyanate is synthesized from the amine, phosgene, diphosgene, triphosgene or the like is reacted with the amine in or without the presence of a base. In the case where the isocyanate is synthesized from the carboxylic acid diphenylphosphorylazide or the like is reacted with the carboxylic acid in the presence of a base. As for a base used in these reactions, for example, an organic base such as triethylamine, N,N-diisopropylethylamine or pyridine can be used. As a solvent, for example, a halogenated hydrocarbon such as dichloromethane or chloroform; an aromatic hydrocarbon such as benzene, toluene or xylene; an ether such as tetrahydrofuran or 1,4-dioxane; or an amide such as N,N-dimethylformamide or N,N-dimethylacetamide can be used.

The forming reaction of —NCONH— or —OCONH— by reaction of an amino or hydroxyl group with an isocyanate can be used in each Reaction Formula mentioned later. The isocyanate used in each case also can be synthesized in the same manner as the above-mentioned.

Figure 2:
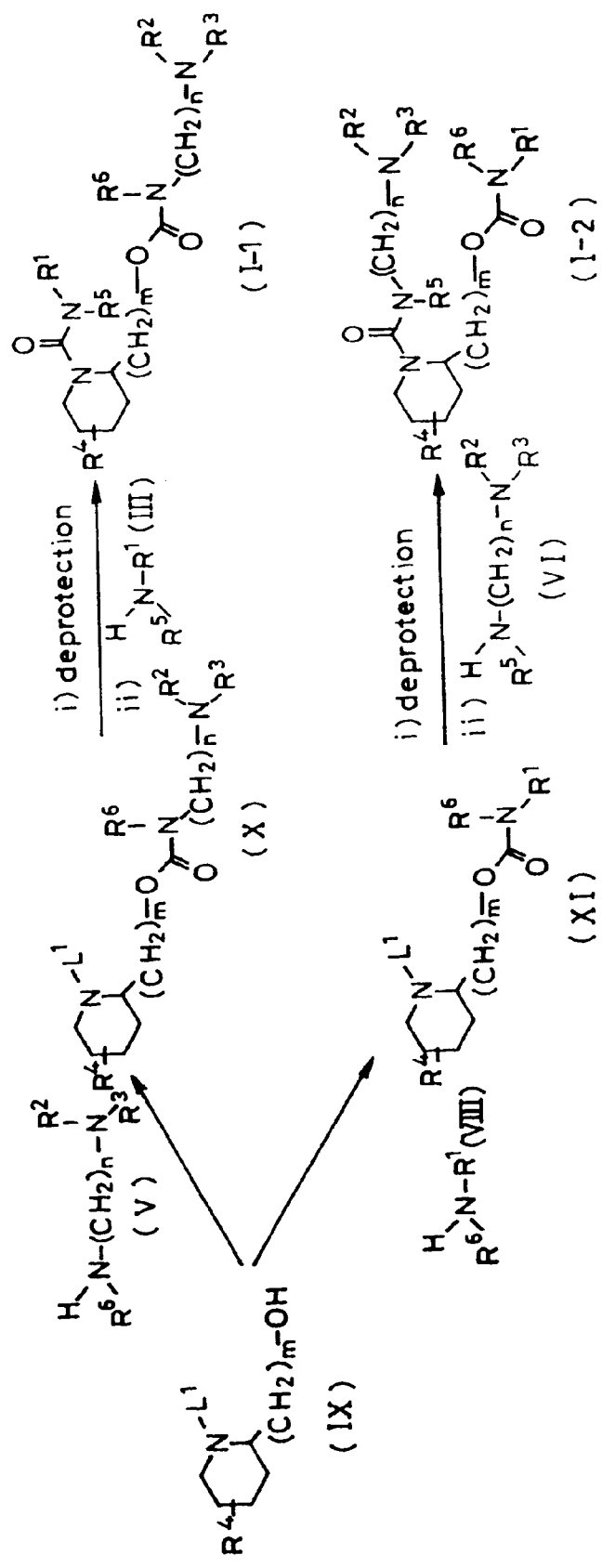

Compounds (I-1) and (I-2) also can be synthesized from Compound (IX) wherein a nitrogen atom of piperidine ring is protected by a protecting group $L^1$, as shown in Reaction Formula AB of FIG. 2. As a protecting group $L^1$, any protecting group can be used as long as the protecting group is not opposed to the object of the present Reaction Formula. For example, an urethane type protecting group such as tert-butyloxycarbonyl group, benzyloxycarbonyl group, 9-fluorenylmethyloxy-carbonyl group; a sulfonyl type protecting group such as 2-(trimethylsilyl) ethanesulfonyl group; a sulfenyl type protecting group such as 2,2,2-trifluoro-1,1-diphenylethanesulfenyl group; or an alkyl type protecting group such as benzyl group, trityl group or 9-phenylfluorenyl group can be used. The definition of $L^1$ is the same in the following.

At the first step of Reaction Formula AB, Compound (X) can be obtained from Compound (IX) and amine (V). Also, Compound (XI) can be obtained from Compound (IX) and amine (VIII). This reaction can be effected according to the first step of said Reaction Formula AA.

At the second step of Reaction Formula AB, Compound (X) or (XI) is deprotected and then reacted with amine (III) or (VI), thereby obtaining Compound (I-1) or (I-2). In the former deprotection reaction, various known methods can be used according to the kind of the amino protecting group $L^1$. Specifically, for example, when $L^1$ is a benzyloxycarbonyl group, by using palladium-carbon as a catalyst, the reaction is effected in a solvent such as ethanol or ethyl acetate under hydrogen gas atmosphere at a temperature within the range of room temperature to the reflux temperature of the solvent, thereby attaining the aimed object. The latter reaction with amine can be effected according to the first step of said Reaction Formula AA.

Figure 3:
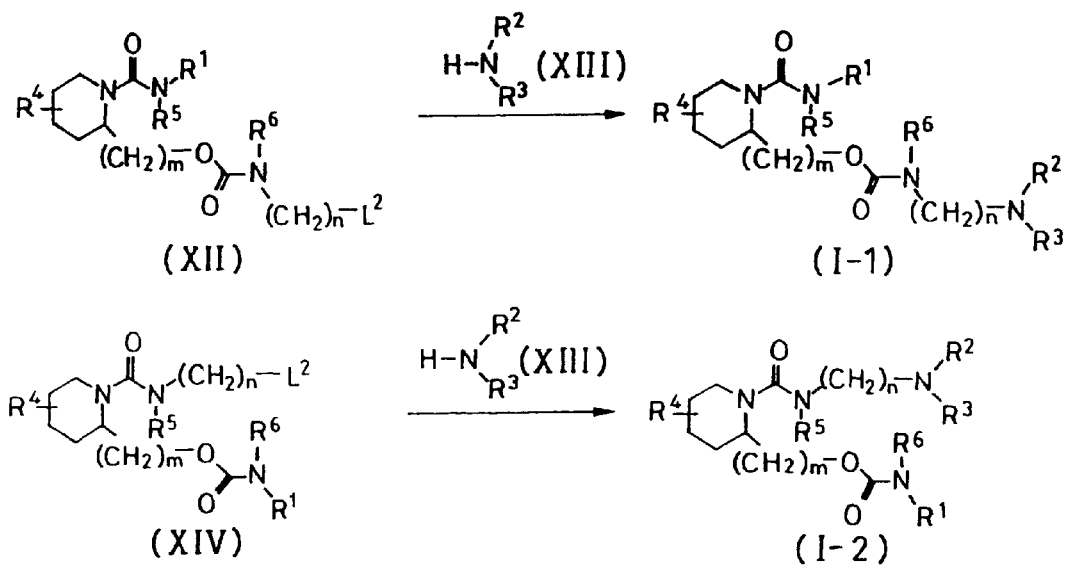

Compound (I-1) or (I-2) also can be synthesized by normally reacting Compound (XII) or (XIV) and amine (XIII) in the presence of a base, as shown in Reaction Formula AC of FIG. 3. $L^2$ in Compound (XII) or (XIV) means an atom or group that can be easily substituted with nitrogen. For example, a halogen atom, tosyloxy group, mesyloxy group or the like can be used therefor. The definition of $L^2$ is the same in the following.

As for a base used in this reaction, for example, an inorganic base such as potassium carbonate, potassium hydroxide, sodium hydroxide or sodium hydride or an organic base such as triethylamine or pyridine can be used. As a solvent, toluene, ether, tetrahydrofuran, acetone, N,N-dimethylformamide or the like can be used. Specifically, for example, by using potassium carbonate as a base, the reaction is effected in a solvent such as acetone or N,N-dimethylformamide at the temperature within a range of room temperature to the reflux temperature of the solvent, thereby attaining the aimed object.

Figure 4:
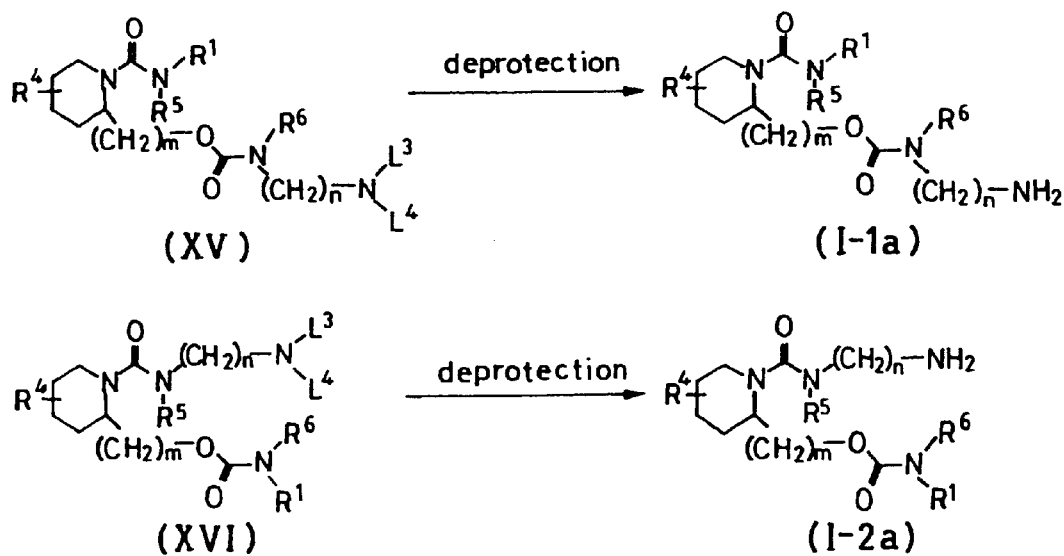

Also, as shown in Reaction Formula AD of FIG. 4, Compound (I-1a) or (I-2a) wherein both $R^2$ and $R^3$ are hydrogen atoms, also can be synthesized by deprotecting amino protecting compound (XV) or (XVI).

Either $L^3$ or $L^4$ in compounds (XV) and (XVI) is an amino protecting group i.e., an urethane type protecting group such as tert-butyloxycarbonyl group, benzyloxycarbonyl group or 9-fluorenylmethyloxycarbonyl group; a sulfonyl type protecting group such as 2-(trimethylsilyl)ethanesulfonyl group; a sulfenyl type protecting group such as 2,2,2-trifluoro-1,1-diphenylethanesulfenyl group; or an alkyl type protecting group such as benzyl group, trityl group or 9-phenylfluorenyl group, while the other is a hydrogen atom, or $L^3$ and $L^4$ together form a phthalimide type amino protecting group. Also, the other amino protecting groups can be used as long as the protecting group is not opposed to the object of the present Reaction Formula. The definitions of $L^3$ and $L^4$ are the same in the following.

In this deprotection reaction, various known methods can be used according to the kinds of amino protecting groups $L^3$ and $L^4$. Specifically, for example, when $L^3$ is a benzyloxycarbonyl group and $L^4$ is a hydrogen atom, by using palladium-carbon as a catalyst, the reaction is effected in a solvent such as ethanol or ethyl acetate under hydrogen gas atmosphere at the temperature within a range of room temperature to the reflux temperature of the solvent, thereby attaining the aimed object. Also, when a phthalimide amino protecting group that is formed by $L^3$ and $L^4$ together is used, by using hydrazine as a deprotecting agent, the reaction is effected in ethanol at a temperature within the range of room temperature to the reflux temperature of the solvent, thereby attaining the aimed object.

Figure 5:
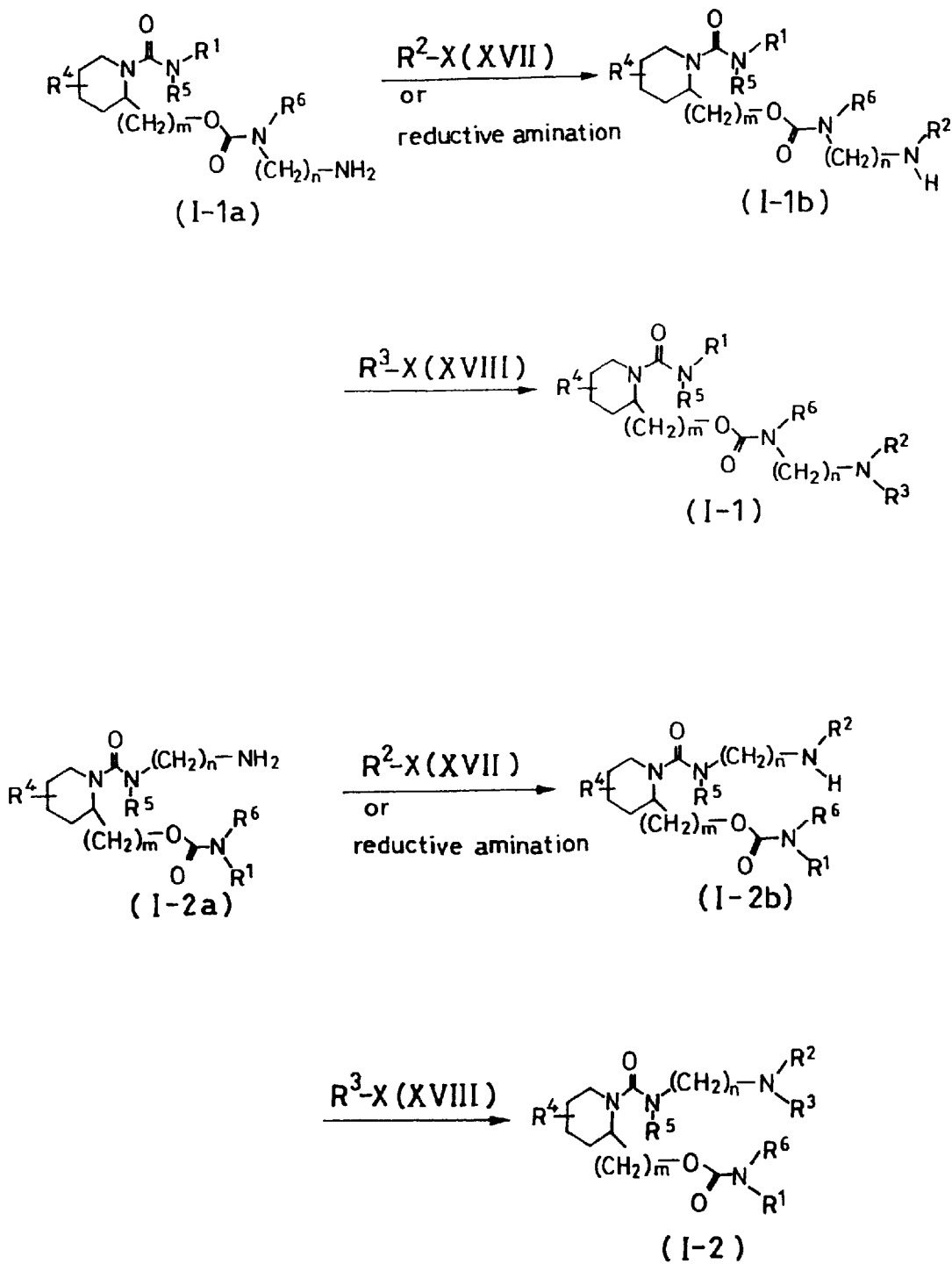

Compound (I-1a) or (I-2a) as shown in Reaction Formula AE of FIG. 5, is reacted with approximately one-equivalent amount of halogenated compound (XVII) in the presence of a base, or is effected to reductive amination reaction with approximately one-equivalent amount of the carbonyl compound corresponding to $R^2$, thereby yielding Compound (I-1b) or (I-2b), respectively. Also, Compound (I-1) or (I-2) can be obtained by reacting Compound (I-1b) or (I-2b) with halogenated compound (XVIII). X represents a halogen atom and the definition of X is the same in the following.

In the reaction with halogenated compound (XVII) or (XVIII), for example, when $R^2$ is a lower alkyl or benzyl group, an inorganic base such as potassium carbonate, potassium hydroxide, sodium hydroxide or sodium hydride or an organic base such as triethylamine or pyridine can be used as a base. Specifically, for example, by using potassium carbonate as a base, the reaction is effected in a solvent such as acetone or N,N-dimethylformamide at the temperature within a range of room temperature to the reflux temperature of the solvent, thereby attaining the aimed object. Also, when $R^2$ is a lower acyl group, an inorganic base such as potassium carbonate, potassium hydroxide or sodium hydroxide or an organic base such as triethylamine or pyridine can be used as a base. Specifically, for example, by using triethylamine or pyridine as a base, the reaction is effected in the solvent such as dichloromethane or benzene at the temperature within the range of 0° C. to room temperature, thereby attaining the aimed object.

The reductive amination reaction can be effected by condensing the carbonyl compound corresponding to $R^2$ with Compound (I-1a) or (I-2a) and then by reducing the produced imine or iminium ion with a reducing agent. It is possible to use cyano sodium borohydride as a reducing agent, or to effect the reaction under the condition of catalytic reduction that uses palladium or the like as a catalyst. Specifically, for example, by using palladium-carbon as a catalyst, the reaction with the carbonyl compound corresponding to $R^2$ is effected in a solvent such as ethanol under the condition of catalytic reduction at a temperature within the range of room temperature to the reflux temperature of the solvent, thereby attaining the aimed object.

Compound (I-1a) or (I-2a) is reacted with approximately two-equivalent amount of halogenated compound (XVII) in the presence of a base in the similar manner to Reaction Formula AE, thereby yielding the compound wherein $R^2$ and $R^3$ in Compound (I-1) or (I-2) are the same, respectively. Also, in the similar manner to Reaction Formula AE, the compound wherein $R^2$ and $R^3$ together form a heterocyclic ring having 3–7 members, Compound (I-1) or (I-2) can be obtained by reacting Compound (I-1a) or (I-2a) with its corresponding dihalogenated compound.

The compound wherein $R^5$ and/or $R^6$ is a lower alkyl, lower acyl or lower alkylcarbamoyl group in Compound (I-1) or (I-2), can be synthesized according to the above-mentioned Reaction Formulae. In addition, such compound can be synthesized by producing the compound wherein $R^5$ and/or $R^6$ is a hydrogen atom in Compound (I-1) or (I-2) according to the above-mentioned Reaction Formulae and reacting the produced compound with its corresponding halogenated compound such as alkyl halide, acyl halide or alkylcarbamoyl halide in or without the presence of a base. This is the same in the synthesis of the present invention's compound mentioned in later.

Figure 6:
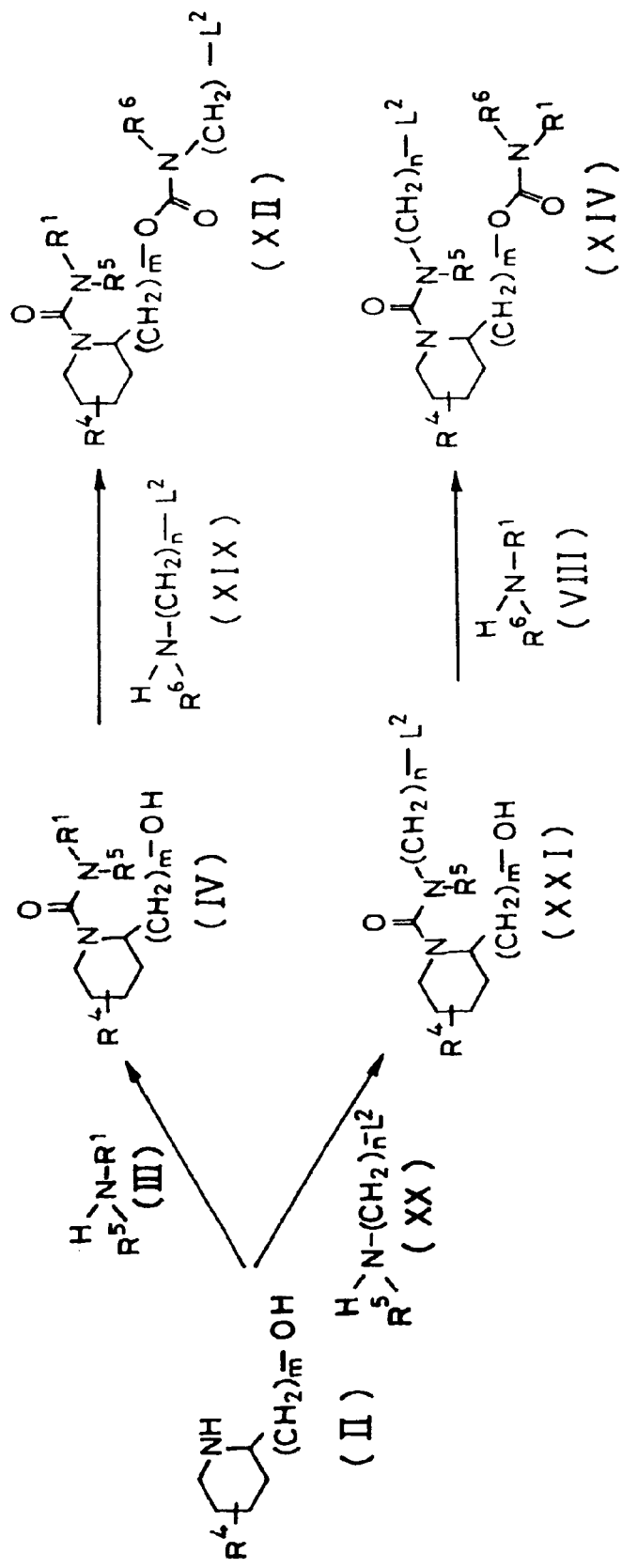
Figure 7:
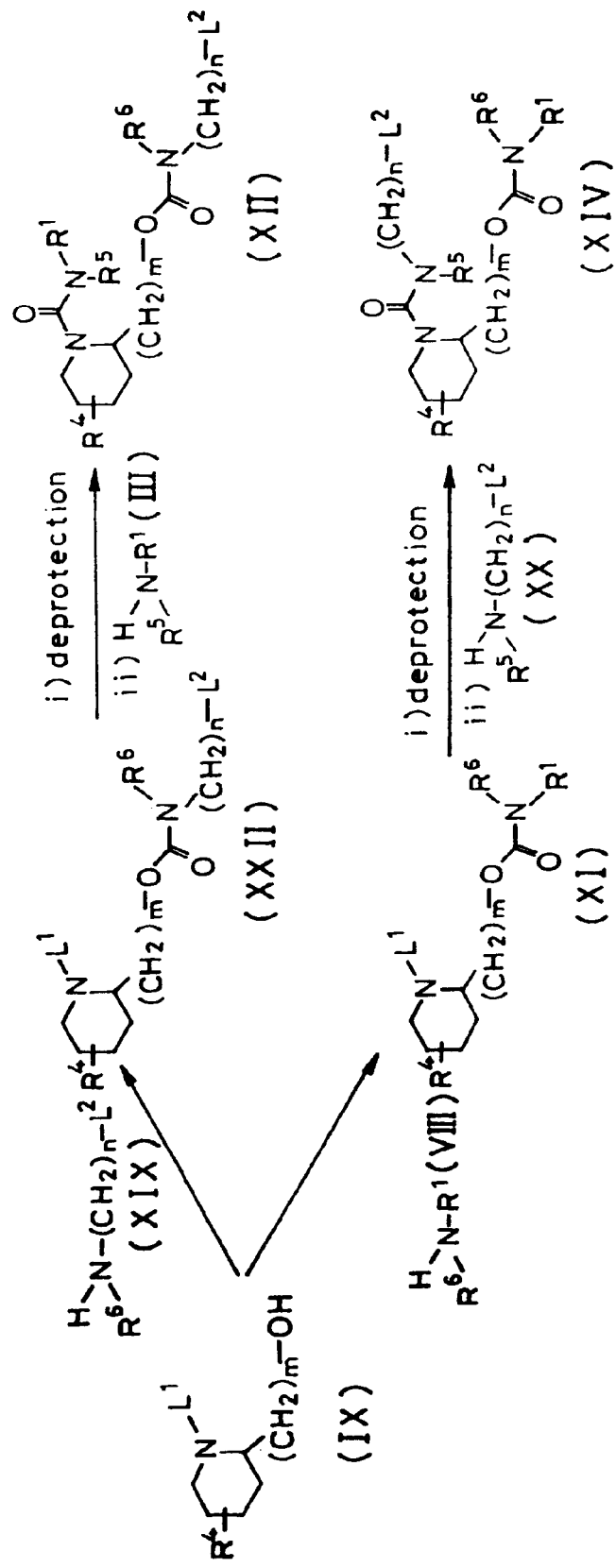

The starting materials (XII) and (XIV) can be synthesized according to Reaction Formulae AF to AG of FIGS. 6 to 7.

Compound (II) is a starting material in Reaction Formula AF. Namely, Compound (IV) synthesized from Compound (II) and amine (III) is reacted with amine (XIX). In the same way, Compound (XXI) synthesized from Compound (II) and amine (XX) is reacted with amine (VIII), thereby obtaining the starting material (XIV). These reactions can be effected according to said Reaction Formula AA.

Compound (IX) is a starting material in Reaction Formula AG. Namely, Compound (XXII) is synthesized from Compound (IX) and amine (XIX). After deprotection of Compound (XXII), the resulting compound is reacted with amine (III), thereby obtaining Compound (XII). In the same way, Compound (XI) synthesized from Compound (IX) and amine (VIII) is deprotected and then the resulting compound is reacted with amine (XX), thereby obtaining Compound (XIV). These reactions can be effected according to said Reaction Formula AB.

Figure 8:
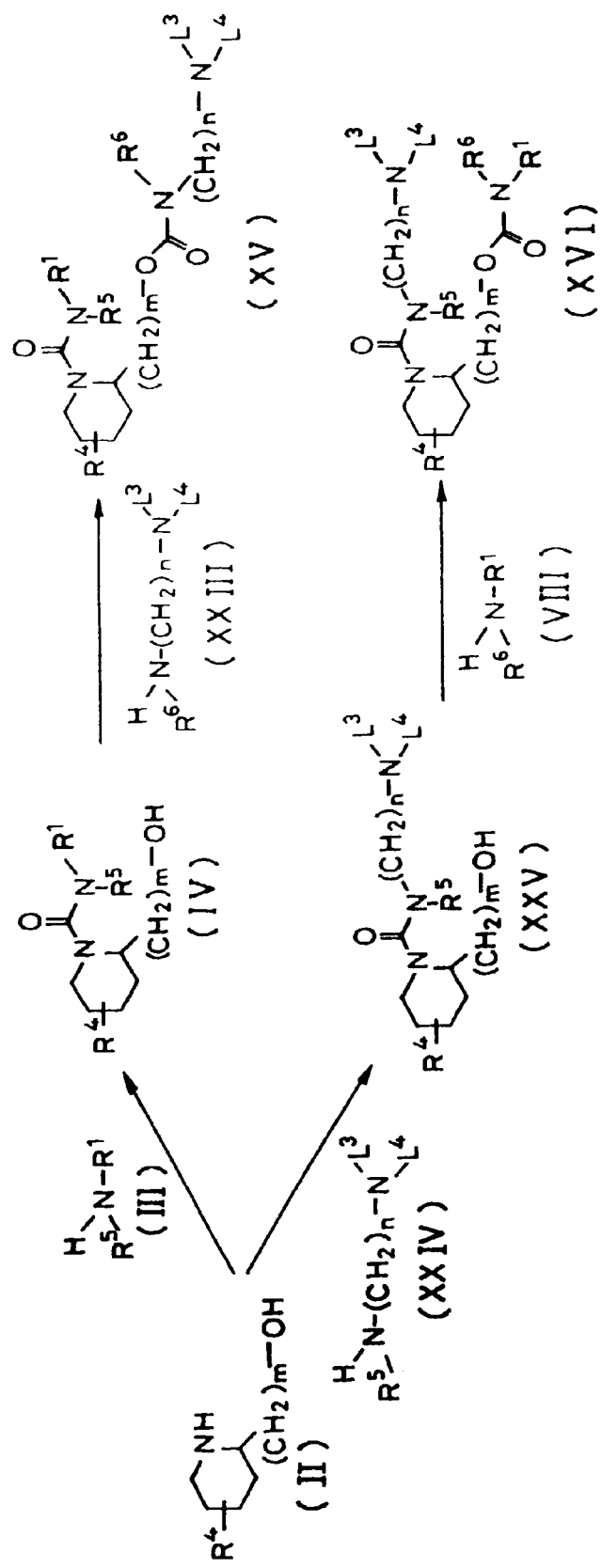
Figure 9:
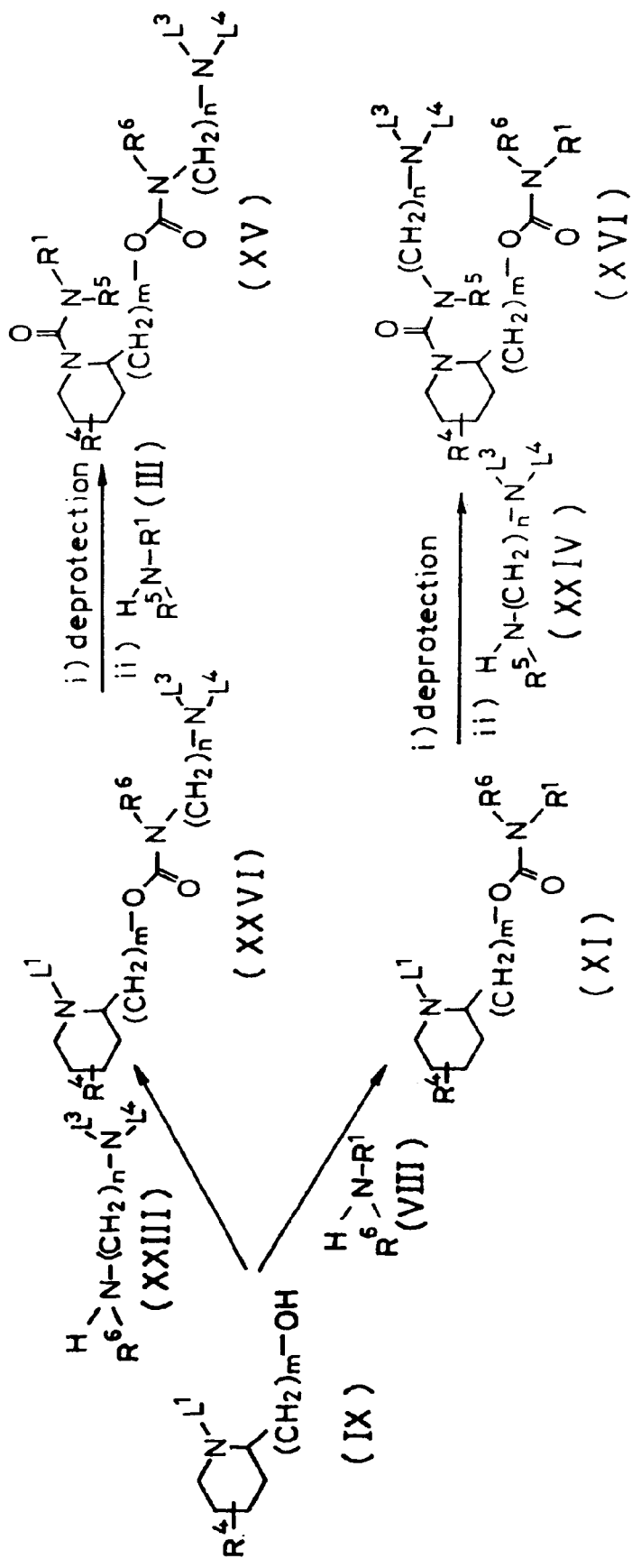

The starting materials (XV) and (XVI) can be synthesized according to Reaction Formulae AH to AI of FIGS. 8 to 9.

Compound (II) is a starting material in Reaction Formula AH. Namely, Compound (IV) synthesized from Compound (II) and amine (III) is reacted with amine (XXIII), thereby obtaining the starting material (XV). In the same way, Compound (XXV) synthesized from Compound (II) and amine (XXIV) is reacted with amine (VIII), thereby obtaining the starting material (XVI). These reactions can be effected according to said Reaction Formula AA.

Compound (IX) is a starting material in Reaction Formula AI. Namely, Compound (XXVI) synthesized from Compound (IX) and amine (XXIII) is deprotected and then the deprotected compound is reacted with amine (III), thereby obtaining Compound (XV). In the same way, Compound (XI) synthesized from Compound (IX) and amine (VIII) is deprotected and then the deprotected compound is reacted with amine (XXIV), thereby obtaining Compound (XVI). These reactions can be effected according to said Reaction Formula AB.

Compounds (I-3) and (I-4) (l=1, Y=—CONR$^5$—, Z=—O—)

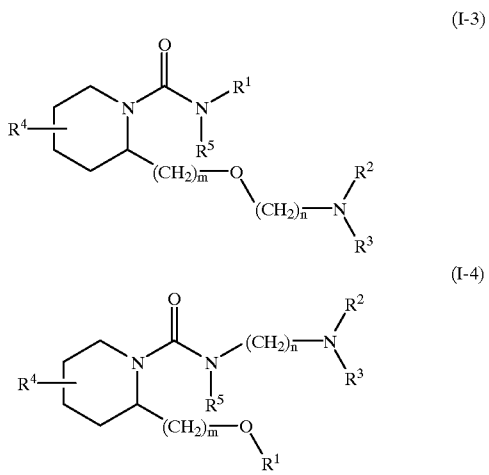

Figure 10:
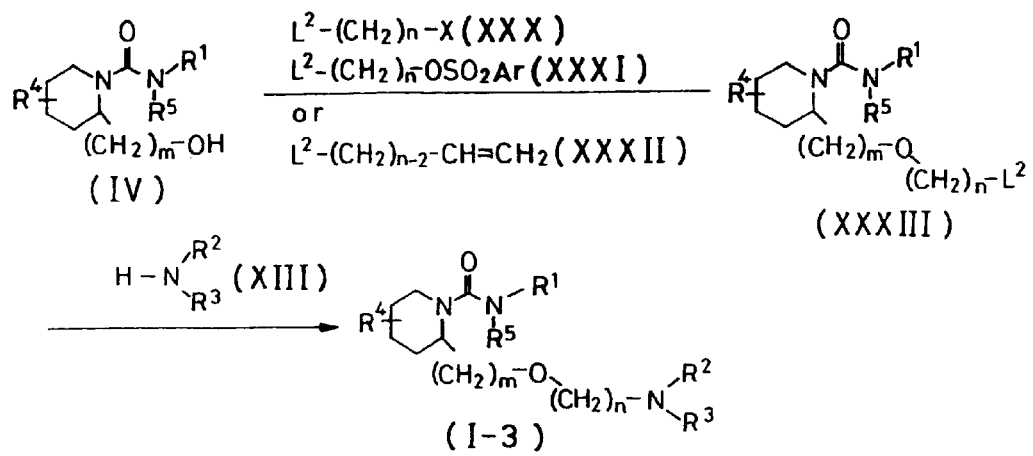
Figure 11:
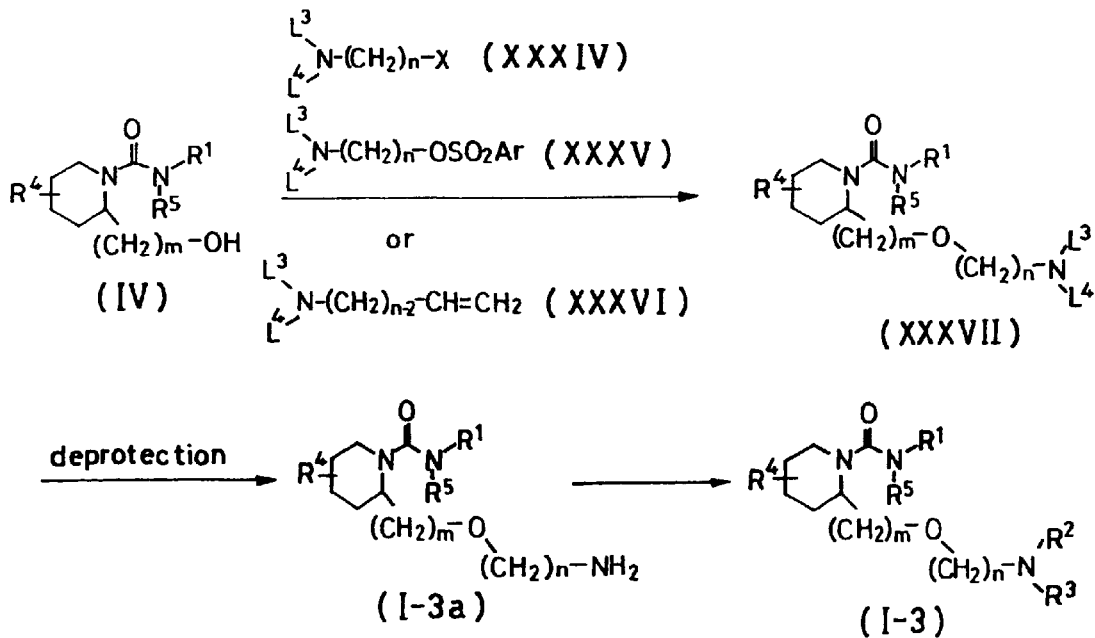

Compound (I-3) can be synthesized according to Reaction Formulae BA to BB of FIGS. 10 to 11.

In Reaction Formula BA, Compound (XXXIII) is synthesized by alkylating a hydroxyl group of Compound (IV) obtained in said Reaction Formula AA. Then, Compound (I-3) can be obtained by reacting Compound (XXXIII) with amine (XIII).

The alkylation reaction at the first step of Reaction Formula BA can be effected by substitution reaction of Compound (IV) with halogenated Compound (XXX) or sulfonate (XXXI) or by addition reaction with alkene (XXXII) in the case where n is 3 or more.

In the substitution reaction with halogenated Compound (XXX), Compound (IV) can be converted into its corresponding alkoxide by using metallic sodium, sodium hydride or the like, and then the alkoxide can be reacted with halogenated Compound (XXX). Also, Compound (IV) and halogenated Compound (XXX) may be directly reacted in the presence of a base. As a base in this occasion, sodium amide, potassium carbonate, sodium hydroxide, barium oxide, silver oxide or the like can be used. As a solvent, an aromatic hydrocarbon such as benzene, toluene or xylene; an ether such as tetrahydrofuran or 1,4-dioxane; an amide such as N,N-dimethylformamide, N,N-dimethylacetamide or hexamethylphosphorylamide; acetonitrile; dimethylsulfoxide; or the like can be used. While the reaction temperature and reaction time may be changed according to the starting materials and the reagents used, the reaction is usually effected at a temperature within the range of 0° C. to the reflux temperature of the solvent. Specifically, for example, Compound (IV) and halogenated Compound (XXX) are reacted in acetone in the presence of potassium carbonate at a temperature of room temperature to the reflux temperature, thereby attaining the aimed object.

In the substitution reaction with sulfonate (XXXI), benzene, tetrahydrofuran, 1,4-dioxane, N,N-dimethylformamide, dimethylsulfoxide, dichloromethane, water or the like can be used as a solvent. While the reaction temperature and reaction time may be changed according to the starting materials and the reagents used, the reaction is usually effected at a temperature within the range of 0° C. to the reflux temperature of the solvent. Sulfonate (XXXI) can be easily synthesized from its corresponding alcohol and p-toluenesulfonyl chloride in the presence of a base such as pyridine. Specifically, for example, 1,4-dioxane solution of the corresponding alcohol and p-toluenesulfonyl chloride is added to an aqueous solution of sodium hydroxide at a temperature of 0° C. to room temperature. Then, Compound (IV) is added to the solution, thereby attaining the aimed object. In sulfonate (XXXI), Ar represents 4-methylphenyl or naphthyl group. The definition of Ar is the same in the following.

Also, in the method of using such sulfonate, substitution reaction can be effected in the same way by using the other ester instead of the sulfonate. For example, a carbonate or trichloroacetimidate corresponding to the sulfonate can be used.

The addition reaction with alkene (XXXII) is effected in the presence of an acidic catalyst. As a catalyst, hydrochloric acid, sulfuric acid, boron trifluoride, trifluoromethane sulfonic acid, tetrafluoroboric acid or the like can be used. An organic metal compound such as sodium methoxide can be used in the place of the acidic catalyst. This reaction is effected in or without the presence of the solvent. As a solvent, benzene, tetrahydrofuran, diethylether, 1,4-dioxane, N,N-dimethylformamide, dichloromethane or the like can be used. While the reaction temperature and reaction time may be changed according to the starting materials and the reagents used, the reaction is usually effected at a temperature within the range of −100° C. to 200° C. Specifically, for example, trifluoromethane sulfonic acid is added to dichloromethane solution of Compound (IV) and alkene (XXXII) at the temperature of −78° C. to 0° C., thereby attaining the aimed object.

The reaction at the second step in Reaction Formula BA can be effected according to Reaction Formula AC.

In Reaction Formula BB of FIG. 11, Compound (XXXVII) synthesized by alkylating a hydroxyl group of Compound (IV), and then deprotected, thereby producing Compound (I-3a) wherein both R$^2$ and R$^3$ are hydrogen atoms. This alkylation reaction can be effected according to said Reaction Formula BA, while deprotection reaction can be effected according to said Reaction Formula AD.

Further, Compound (I-3a) can be leaded to Compound (I-3) according to said Reaction Formula AE.

Figures 12, 13, 14:
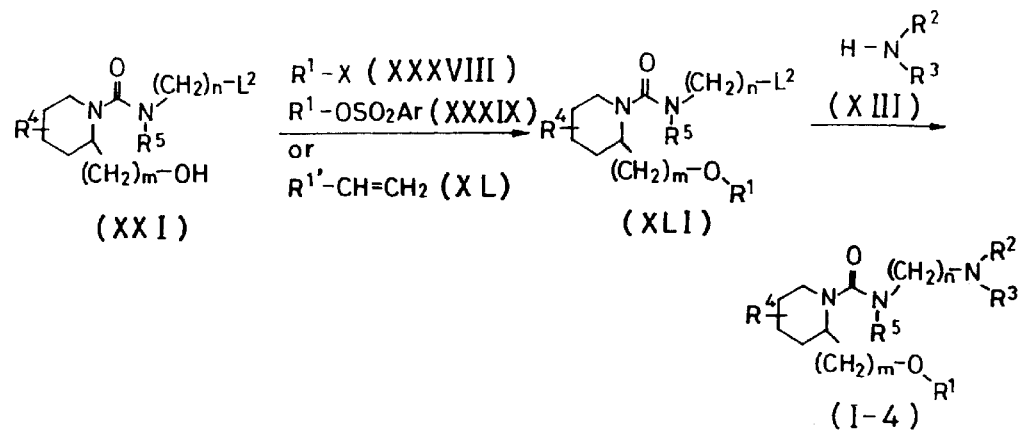

On the other hand, Compound (I-4) can be synthesized according to Reaction Formulae BC to BE of FIGS. 12 to 14.

In Reaction Formula BC of FIG. 12, Compound (XLI) is synthesized by alkylating a hydroxyl group of Compound (XXI) and then is reacted with amine (XIII), thereby obtaining Compound (I-4).

This alkylation reaction can be effected similar to Reaction Formula BA, by substitution reaction of Compound (XXI) with halogenated Compound (XXXVIII) or sulfonate (XXXIX) or by addition reaction with alkene (XL) in the case where $R^1$ have 2 or more carbon numbers. $R^{1,}$ in alkene (XL) can be selected so as that the alkene can correspond to $R^1$. For example, $R^{1,}$ represents a hexadecyl group when $R^1$ is an octadecyl group.

The second step of Reaction Formula BC can be effected according to with Reaction Formula AC.

In Reaction Formula BD of FIG. 13, Compound (XLII) is synthesized by alkylating a hydroxyl group of Compound (XXV) and then deprotected, thereby producing Compound (I-4a) wherein both $R^2$ and $R^3$ are hydrogen atoms. This alkylation reaction can be effected according to said Reaction Formula BA, while the deprotection reaction can be effected according to said Reaction Formula AD.

Further, Compound (I-4a) can be leaded to Compound (I-4) in the similar manner to said Reaction Formula AE.

Compound (I-4) also can be synthesized by using Compound (IX) as a starting material as shown in Reaction Formula BE of FIG. 14. Namely, Compound (XLIII) can be obtained by alkylating a hydroxyl group of Compound (IX) according to Reaction Formula BA. Then, Compound (I-4) can be obtained by reactions according to: the second step of said Reaction Formula AB; the second step of said Reaction Formula AG; and Reaction Formula AC; or the second step of Reaction Formula AI and Reaction Formulae AD to AE, by way of Compound (XLIII) and Compound (XLIV).

Compounds (I-5) and (I-6) (l=1, Y=—$CONR^5$—, Z=—OCO—)

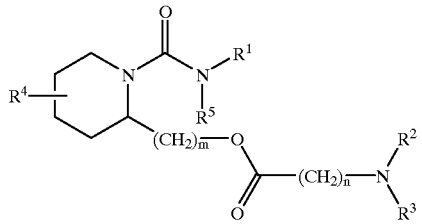

(I-5)

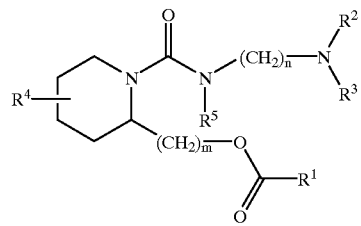

(I-6)

Compound (I-5) can be synthesized as shown in Reaction Formulae CA to CC of FIGS. 15 to 17.

In Reaction Formula CA, Compound (I-5) can be obtained by acylating a hydroxyl group of Compound (IV). This reaction can be effected by dehydrating condensation reaction of Compound (IV) with carboxylic acid (XLV), reaction with acid halide (XLVI) or ester-interchange reaction with ester (XLVII).

In the dehydrating condensation reaction with carboxylic acid (XLV), there is a method wherein both compounds are directly reacted in the presence of an acid catalyst, a method wherein carboxylic acid (XLV) is converted into an activated ester and then the latter is reacted with Compound (IV), or the like. In the former method, a mineral acid such as hydrochloric acid, sulfuric acid or boric acid; an organic acid such as aromatic sulfonic acid; Lewis acid such as boron trifluoride; or the like can be used as an acid catalyst. As a solvent, an aromatic hydrocarbon such as benzene, toluene or xylene; an ether such as tetrahydrofuran or 1,4-dioxane; an amide such as N,N-dimethylformamide or N,N-dimethylacetamide; a halogenated hydrocarbon such as dichloromethane or dichloroethane; or the like can be used. While the reaction temperature and reaction time may be changed according to the starting materials and the reagents used, the reaction is usually effected at a temperature within the range of 0° C. to the reflux temperature of the solvent. Specifically, for example, the reaction is effected at a temperature of room temperature to the reflux temperature of the solvent after adding concentrated sulfuric acid to dichloroethane solution of Compound (IV) and carboxylic acid (XLV), or by reacting the mixture of Compound (IV), carboxylic acid (XLV) and boron trifluoride is reacted at a temperature of room temperature to the reflux temperature of the solvent, thereby attaining the aimed object.

In the method by way of activated ester of carboxylic acid (XLV), after converting carboxylic acid (XLV) into its corresponding activated ester by using trifluoroacetic anhydride, N,N-dicyclohexylcarbodiimide (DCC) or the like, the activated ester is reacted with Compound (IV). As a solvent, benzene, tetrahydrofuran, N,N-dimethylformamide, dichloromethane or the like can be used. While the reaction temperature and reaction time may be changed according to the starting materials and the reagents used, the reaction is usually effected at a temperature within the range of 0° C. to the reflux temperature of the solvent. Specifically, for example, trifluoroacetic anhydride is added to benzene solution of carboxylic acid (XLV) at a temperature within the range of 0° C. to room temperature so as that carboxylic acid (XLV) can be converted into its corresponding activated ester. Then, the activated ester is reacted with Compound (IV), thereby attaining the aimed object.

The reaction with acid halide (XLVI) is usually effected in the presence of a base. As a base, an inorganic base such as sodium hydroxide or potassium hydroxide or an organic base such as pyridine, dimethylaniline or triethylamine can be used. As a solvent, benzene, tetrahydrofuran, 1,4-dioxane, N,N-dimethylformamide, dichloro-methane, water or the like can be used. While the reaction temperature and reaction time may be changed according to the starting materials and the reagents used, the reaction is usually effected at a temperature within the range of 0° C. to the reflux temperature of the solvent. Specifically, for example, the reaction is effected at a temperature within the range of 0° C. to room temperature after adding acid halide (XLVI) to dichloromethane solution of Compound (IV) and pyridine or an aqueous solution of sodium hydroxide is added dropwise into the mixture of Compound (IV) and acid halide (XLVI), thereby attaining the aimed object.

In ester interchange reaction with ester (XLVII), an acid such as sulfuric acid or p-toluenesulfonic acid or a base such as potassium alkoxide or titan (IV) alkoxide can be used as a catalyst. The reaction is effected in or without the presence of the solvent. From the nature of the reaction, it is preferable to use excessively either of Compound (IV) or ester (XLVII) or to remove the produced alcohol $L^5OH$ from reaction system. As a solvent, benzene, toluene, tetrahydrofuran, 1,4-dioxane, N,N-dimethylformamide, dichloromethane or the like can be used. While the reaction temperature and reaction time may be changed according to the starting materials and the reagents used, the reaction is usually effected at a temperature within the range of 0° C. to 200° C., and preferably, room temperature to the reflux temperature of the solvent. Specifically, for example, after titan (IV) alkoxide is added to benzene solution of Compound (IV) and ester (VLVII), the reaction is effected at a temperature within the range of room temperature to the reflux temperature of the solvent, thereby attaining the aimed object. $L^5$ in ester (XLVII) may be any group as long as the group can form an ester which is usable in this ester interchange reaction in usual. For example, an alkyl group such as methyl or ethyl group can be used therefor. The definition of $L^5$ is the same in the following.

In Reaction Formula CB of FIG. 16, Compound (LI) is synthesized by acylating a hydroxyl group of Compound (IV) and then reacted with amine (XIII), thereby obtaining Compound (I-5).

The acylation reaction at the first step can be effected according to said Reaction Formula CA, while the reaction at the second step can be effected according to said Reaction Formula AC.

In Reaction Formula CC of FIG. 17, amino-protecting compound (LV) is synthesized by acylating a hydroxyl group of Compound (IV) and then deprotected, thereby obtaining Compound (I-5a) wherein both $R^2$ and $R^3$ are hydrogen atoms. This acylation reaction can be effected according to said Reaction Formula CA, while the deprotection reaction can be effected according to said Reaction Formula AD.

Further, Compound (I-5a) can be leaded to Compound (I-5) in the similar manner to said Reaction Formula AE.

On the other hand, Compound (I-6) can be synthesized according to Reaction Formulae CD to CG of FIGS. 18 to 21.

In Reaction Formula CD of FIG. 18, Compound (I-6) can be obtained by acylating a hydroxyl group of Compound (VII). This reaction can be effected in the similar manner to Reaction Formula CA, by dehydrating condensation reaction of Compound (VII) and carboxylic acid (LVI), reaction with acid halide (LVII) or acid anhydride (LVIII) or ester interchange reaction with ester (LIX). When acid anhydride (LVIII) that was not described in Reaction Formula CA is used, it is possible to use the same way as the case of using acid halide.

In Reaction Formula CE of FIG. 19, Compound (LX) is synthesized by acylating a hydroxyl group of Compound (XXI) and then reacted with amine (XIII), thereby obtaining Compound (I-6). This acylation reaction can be effected according to said Reaction Formula CA, while the reaction at the second step can be effected according to said Reaction Formula AC.

Figure 20:
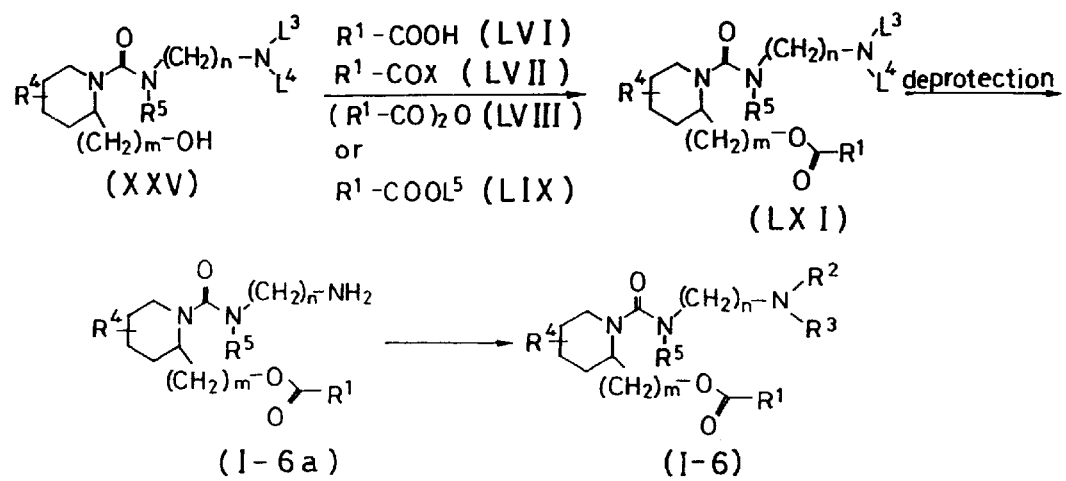
Figure 21:
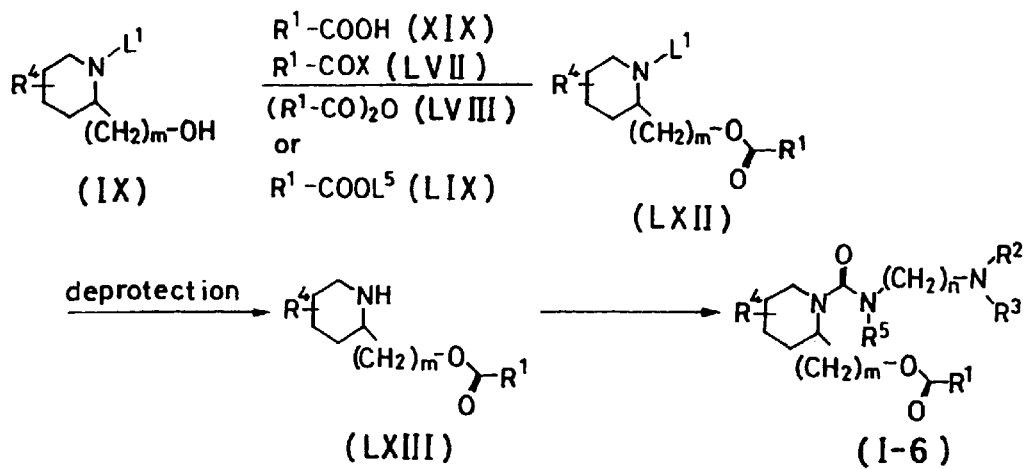

In Reaction Formula CF of FIG. 20, amino protection compound (LXI) is synthesized by acylating a hydroxyl group of Compound (XXV). Amino protection compound (LXI) is effected to deprotection reaction, thereby yielding the present invention's Compound (I-6a) that both $R^2$ and $R^3$ are a hydrogen atom. This acylation reaction can be effected according to said Reaction Formula CA, while deprotection reaction can be effected according to Reaction Formula AD.

Further, Compound (I-6a) can be leaded to Compound (I-6) in the similar manner to Reaction Formula AE.

As shown in Reaction Formula CG, Compound (1-6) also can be synthesized by using Compound (IX) as a starting material. Namely, Compound (LXII) is synthesized by acylating a hydroxyl group of Compound (IX). Then, Compound (I-6) can be obtained by reactions according to: the second step of said Reaction Formula AB; the second step of Reaction Formula AG; and Reaction Formula AC; or the second step of Reaction Formula AI and Reaction Formulae AD to AE, by way of Compound (LXII) and Compound (LXIII).

Compounds (I-7) and (I-8) (l=1, Y=—CONR$^5$—, Z=—NR$^6$—)

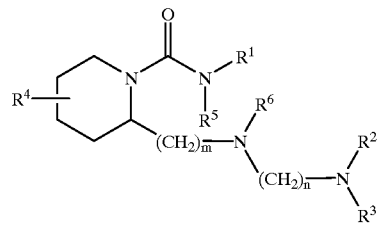

(I-7)

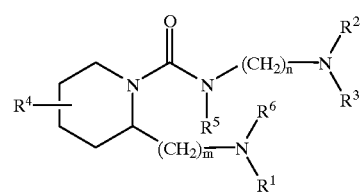

(I-8)

Figure 22:
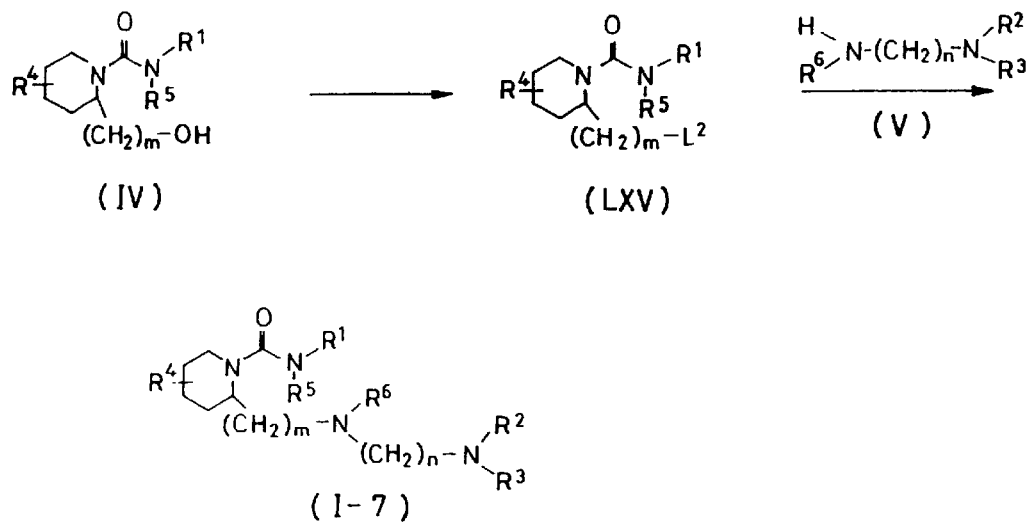
Figure 23:
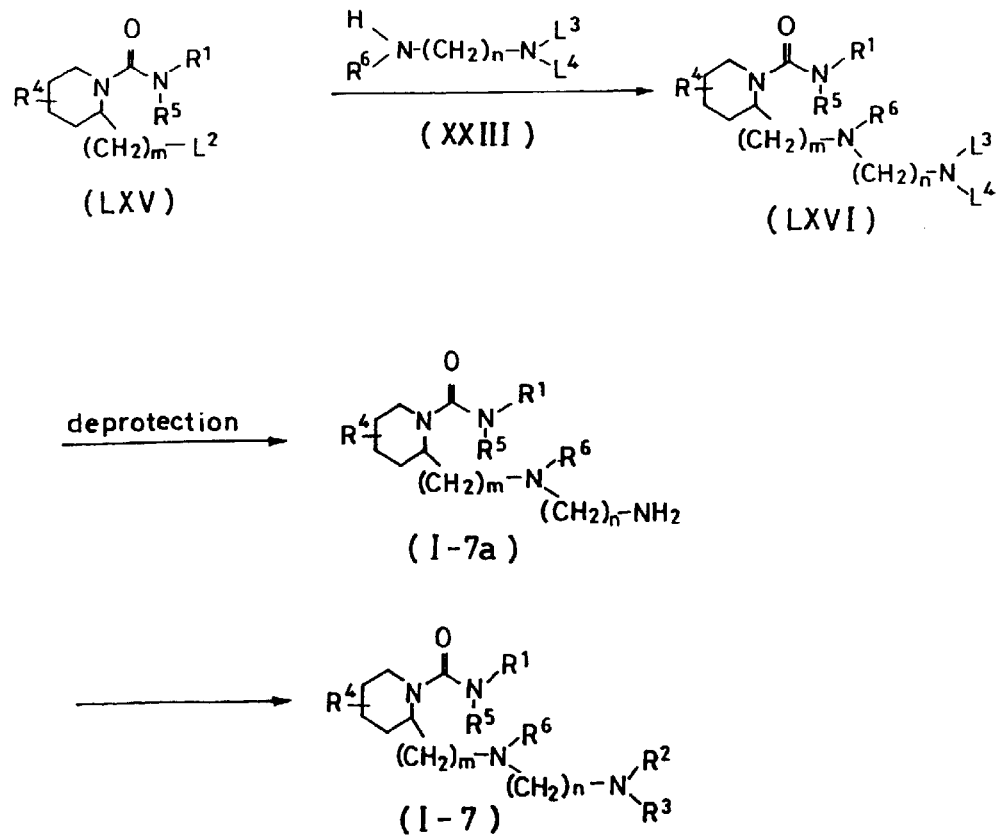

Compound (I-7), for example, can be synthesized as shown in Reaction Formulae DA to DB of FIGS. 22 to 23.

In Reaction Formula DA, Compound (LXV) is synthesized by substituting a hydroxyl group of Compound (IV) to the group $L^2$ that is easily substituted for nitrogen atom. Then, by reacting Compound (LXV) with amine (V), Compound (I-7) can be obtained.

In the first step of Reaction Formula DA, for example, phosphoric pentachloride, phosphoric trichloride, thionyl chloride or the like can be used in the case where $L^2$ is a halogen atom. As an additive, for example, an organic acid such as triethylamine, pyridine or N-methylmorpholine can be used. As a solvent, for example, a halogenated hydrocarbon such as dichloromethane or chloroform; an aromatic such as benzene, toluene, xylene or pyridine; an ether such as diethylether, tetrahydrofuran or 1,4-dioxane; an amide such as N,N-dimethylformamide or N,N-dimethylacetamide; a sulfoxide such as dimethylsulfoxide; or a mixed solvent thereof can be used. While the reaction temperature and reaction time may be changed according to the starting materials used, the reaction is usually effected at a temperature within the range of 0° C. to the reflux temperature of the solvent.

When $L^2$ is a tosyloxy, mesyloxy group or the like, it is possible to react Compound (IV) with p-toluenesulfonyl chloride, methylsulfonyl chloride or the like in the presence of a base such as pyridine. Specifically, for example, 1,4-dioxane solution of Compound (IV) and p-toluenesulfonyl chloride are added to an aqueous solution of sodium hydroxide at a temperature within the range of 0° C. to room temperature, thereby attaining the aimed object.

The second step of Reaction Formula DA can be effected according to Reaction Formula AC.

In Reaction Formula DB of FIG. 23, Compound (LXVI) is synthesized from Compound (LXV) and amine (XXIII) and then deprotected, thereby obtaining Compound (I-7a) wherein both $R^2$ and $R^3$ are hydrogen atoms. The reaction at the first step in Reaction Formula DB can be effected according to said Reaction Formula AC, while the deprotection reaction at the second step can be effected according to Reaction Formula AD.

Further, Compound (I-7a) can be leaded to Compound (I-7) in the similar manner to Reaction Formula AE.

Figure 26:
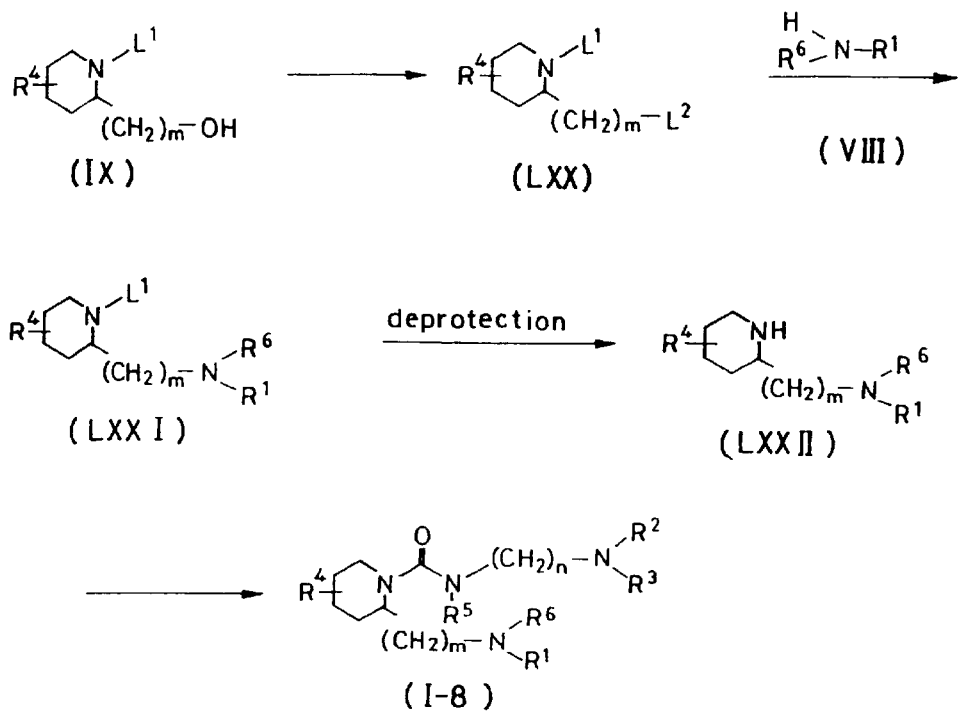

On the other hand, Compound (I-8) can be synthesized as shown in Reaction Formulae DC to DE of FIGS. 24 to 26.

Reaction Formula DC is effected in the similar manner to Reaction Formula DA.

The first and second steps of Reaction Formula DD can be effected according to the first step of Reaction Formula DA and Reaction Formula AC, respectively. The deprotection reaction at the third step can be effected according to Reaction Formula AD. Also, Compound (I-8a) wherein both $R^2$ and $R^3$ are hydrogen atoms can be leaded to Compound (I-8) in the similar manner to Reaction Formula AE.

The first and second steps of Reaction Formula DE can be effected according to the first step of Reaction Formula DA and Reaction Formula AC, respectively. The reaction of third and forth steps can be effected according to: the second step of Reaction Formula AB; the second step of Reaction Formula AG and Reaction Formula AC; or the second step of Reaction Formula AI and Reaction Formulae AD to AE.

Compounds (I-9) and (I-10) (l=0, Z=—OCONR$^6$—)

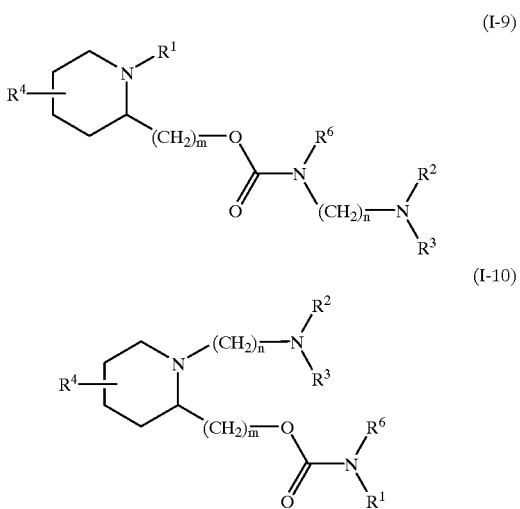

Figure 27:
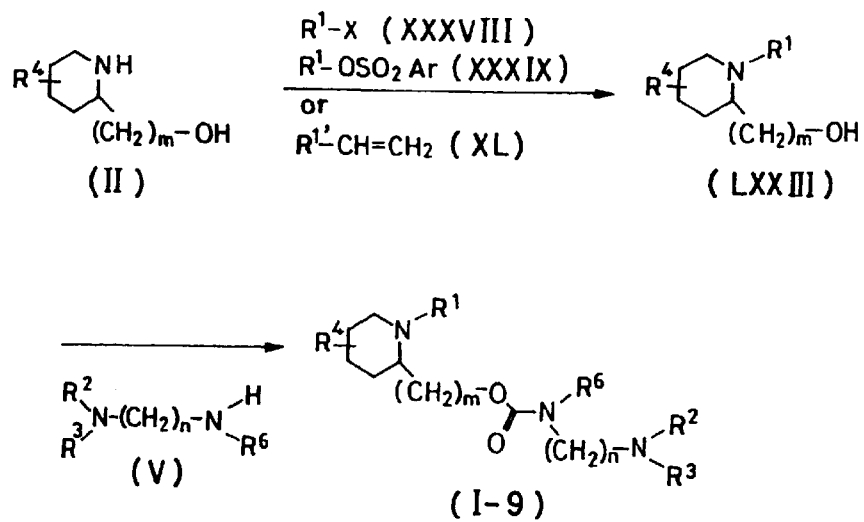
Figure 28:
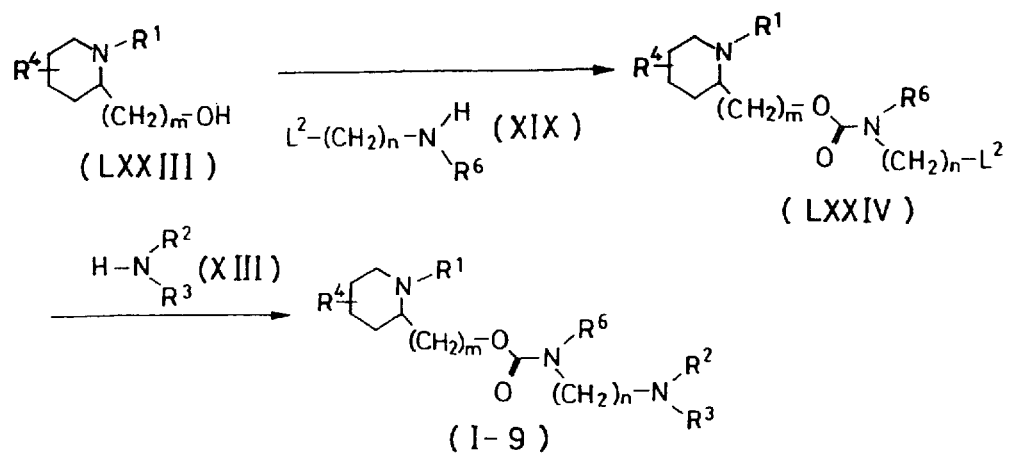
Figure 29:
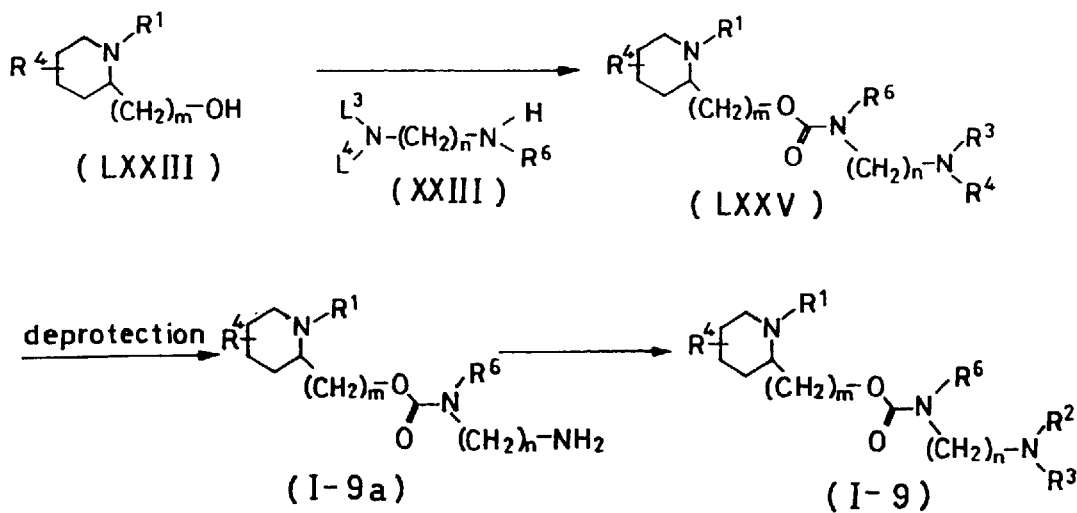

Compound (I-9) can be synthesized as shown in Reaction Formulae EA to EC of FIGS. 27 to 29.

In Reaction Formula EA of FIG. 27, Compound (LXXIII) is synthesized by alkylating an amino group of Compound (II) and then reacted with amine (V), thereby obtaining Compound (I-9).

This alkylation reaction can be effected by substitution reaction of Compound (II) with halogenated compound (XXXVIII) or sulfonate (XXXIX), or addition reaction with alkene (XL) according to the first step of said Reaction Formula BA.

Compound (LXXIII) can be also synthesized by reducing its corresponding amide compound or by reductive amination reaction with its corresponding carbonyl compound. Namely, in the former reaction, by using a reducing agent such as lithium aluminium hydride or diborane, amide (C) that is obtained at the first step of Reaction Formula IA mentioned later is reacted in a solvent such as diethylether, tetrahydrofuran or methylene chloride at a temperature within the range of 0° C. to the reflux temperature of the solvent, thereby attaining the aimed object. Also, the latter reductive amination reaction can be attained by condensing the carbonyl compound corresponding to $R^1$ with Compound (II) and then by reducing the produced imine or iminium ion. As a reducing method, for example, a method using a reducing agent such as lithium aluminium hydride, sodium borohydride, cyano sodium borohydride or diborane, or catalytic reduction method using palladium or the like as a catalyst can be used. Specifically, for example, by using palladium-carbon as a catalyst, the reaction with carbonyl compound corresponding to $R^1$ is effected in a solvent such as ethanol under the condition of catalytic reduction at a temperature within the range of room temperature to the reflux temperature of the solvent, thereby attaining the aimed object.

The reaction at the second step in Reaction Formula EA can be effected according to the second step of said Reaction Formula AA.

In Reaction Formula EB of FIG. 28, Compound (LXXIV) is synthesized from Compound (LXXIII) and amine (XIX) and then reacted with amine (XIII), thereby obtaining Compound (I-9). The reaction at the first step can be effected according to the second step of said Reaction Formula AF, while the reaction of the second step can be effected according to said Reaction Formula AC.

In Reaction Formula EC of FIG. 29, amino-protecting compound (LXXV) is synthesized from Compound (LXXIII) and amine (XXIII) and then deprotected, thereby obtaining Compound (I-9a) wherein both $R^2$ and $R^3$ are hydrogen atoms. The reaction at the first step can be effected according to the second step of said Reaction Formula AH, while the reaction of the second step can be effected according to said Reaction Formula AD.

Further, Compound (I-9a) can be leaded to Compound (I-9) in the similar manner to said Reaction Formula AE.

On the other hand, Compound (I-10) can be synthesized as shown in Reaction Formulae ED to EG of FIGS. 30 to 33.

Figure 30:
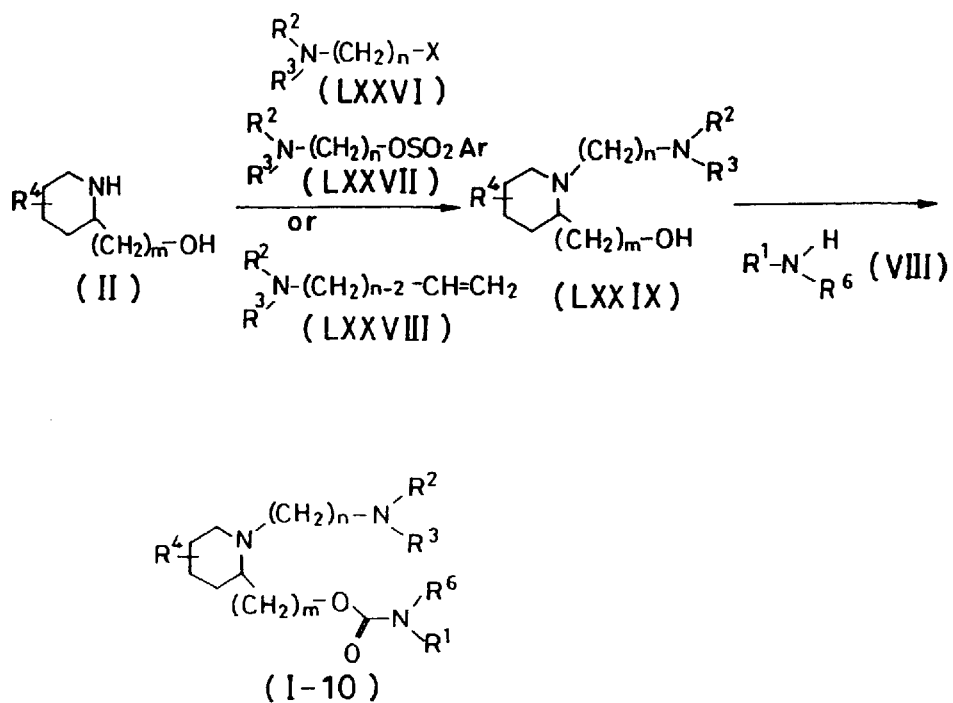

In Reaction Formula ED of FIG. 30, Compound (LXXIX) is synthesized by alkylating an amino group of Compound (II) and then reacted with amine (VIII), thereby obtaining Compound (I-10). This alkylation reaction can be effected according to the first step of said Reaction Formula BA, while the reaction of the second step can be effected according to the second step of said Reaction Formula AA.

Figure 31:
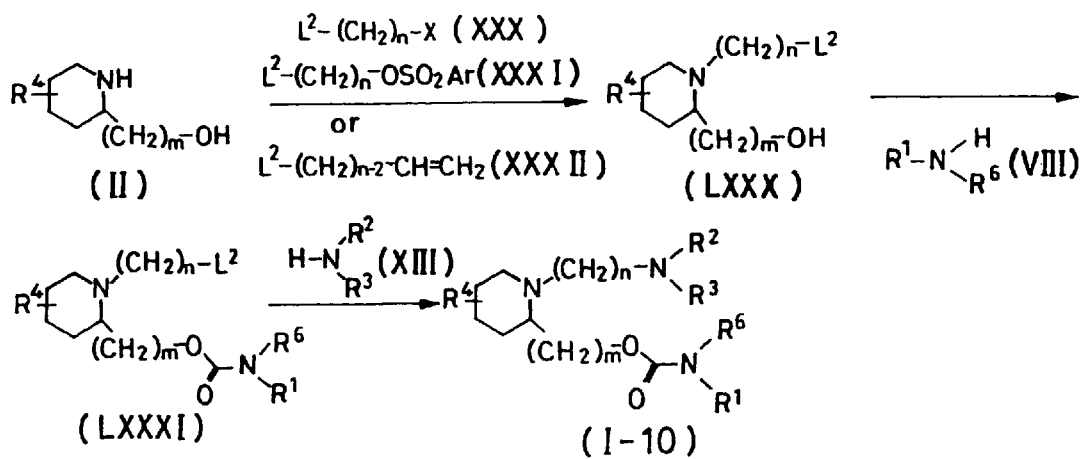

In Reaction Formula EE of FIG. 31, Compound (LXXX) is synthesized by alkylating an amino group of Compound (II) and then reacted with amine (VIII) and (XIII) successively, to obtain Compound (I-10). The alkylation reaction at the first step can be effected according to the first step of said Reaction Formula BA. The reaction at the second step can be effected according to the second step of said Reaction Formula AF, while the reaction of the third step can be effected in accordance with said Reaction Formula AC.

Figure 32:
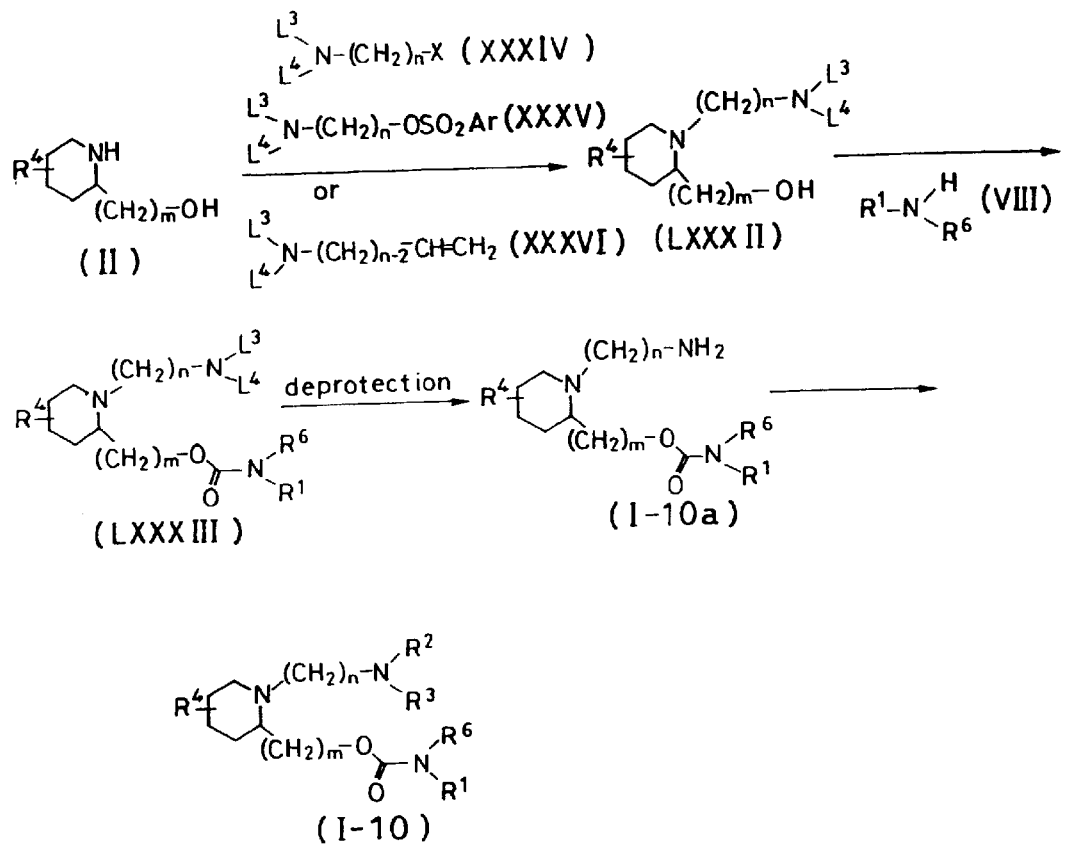

In Reaction Formula EF of FIG. 32, Compound (LXXXII) synthesized by alkylating an amino group of Compound (II) is reacted with amine (III), and then the produced compound is deprotected, thereby obtaining Compound (I-10a) wherein both $R^2$ and $R^3$ are hydrogen atoms. The alkylation reaction at the first step, the reaction of the second step and deprotection reaction of the third step can be effected according to the first step of Reaction Formula BA, the second step of Reaction Formula AA and Reaction Formula AD, respectively.

Further, Compound (I-10a) can be leaded to Compound (I-10) in the similar manner to said Reaction Formula AE.

Figure 33:
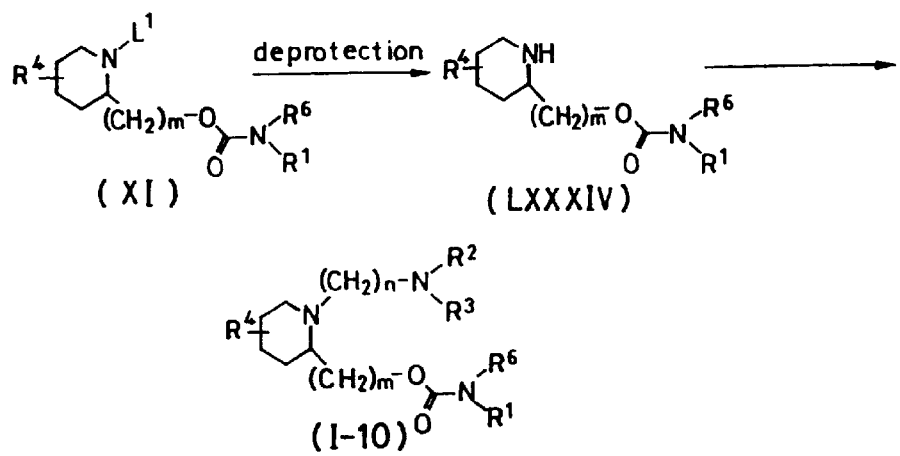

As shown in Reaction Formula EG of FIG. 33, Compound (I-10) also can be synthesized by using Compound (XI) obtained by said Reaction Formula AB as a starting material. Namely, Compound (LXXXIV) is synthesized from Compound (XI) according to deprotection reaction at the second step in said Reaction Formula AB. Then, Compound (LXXXIV) can be leaded to Compound (I-10) by reactions according to: the first step of Reaction Formula ED; the first and third steps of Reaction Formula EE; or the first, third and forth steps of Reaction Formula EF.

Compounds (I-11) and (I-12) (l=0, Z=—O—)

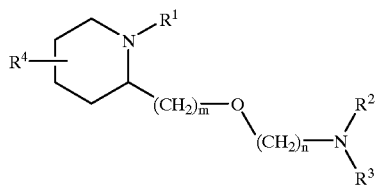
(I-11)

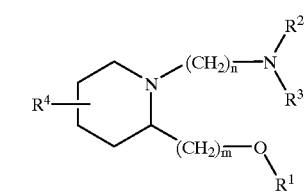
(I-12)

Compound (I-11), for example, can be synthesized as shown in Reaction Formulae FA to FB of FIGS. 34 to 35.

In Reaction Formula FA, Compound (LXXXV) is synthesized from Compound (IX) according to Reaction Formula BA. Then, deprotection reaction at the second step in Reaction Formula AB and alkylation reaction at the first step in Reaction Formula EA are effected successively, thereby obtaining Compound (I-11).

In Reaction Formula FB, Compound (LXXXVI) is synthesized from Compound (IX) according to the first step at Reaction Formula BB. Then, deprotection reaction at the second step in Reaction Formula AB and alkylation reaction at the first step in Reaction Formula EA are effected successively, thereby obtaining Compound (LXXXVII). Compound (I-11a) can be synthesized by deprotecting Compound (LXXXVII) according to Reaction Formula AD. Further, Compound (I-11a) can be leaded to Compound (I-11) according to said Reaction Formula AE.

Figure 36:
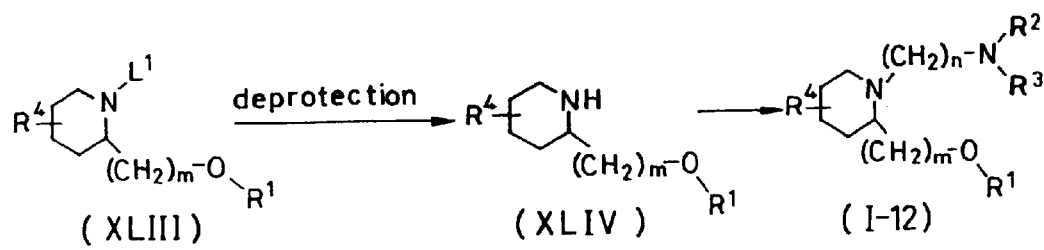

On the other hand, Compound (I-12) can be synthesized as shown in Reaction Formula FC of FIG. 36. In Reaction Formula FC, Compound (I-12) can be obtained from Compound (XLIII) by way of Compound (XLIV) in the similar manner to Reaction Formula EG.

Compounds (I-13) and (I-14) (l=0, Z=—OCO—)

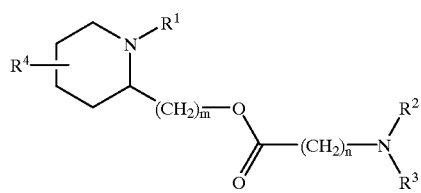
(I-13)

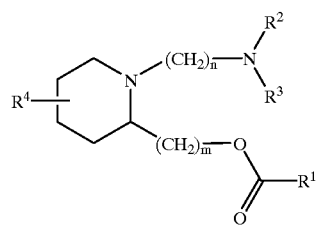
(I-14)

Figure 37:
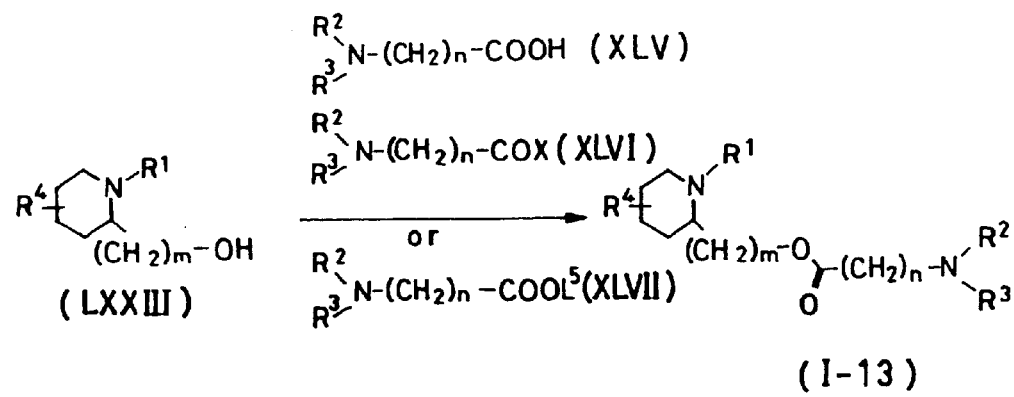
Figure 38:
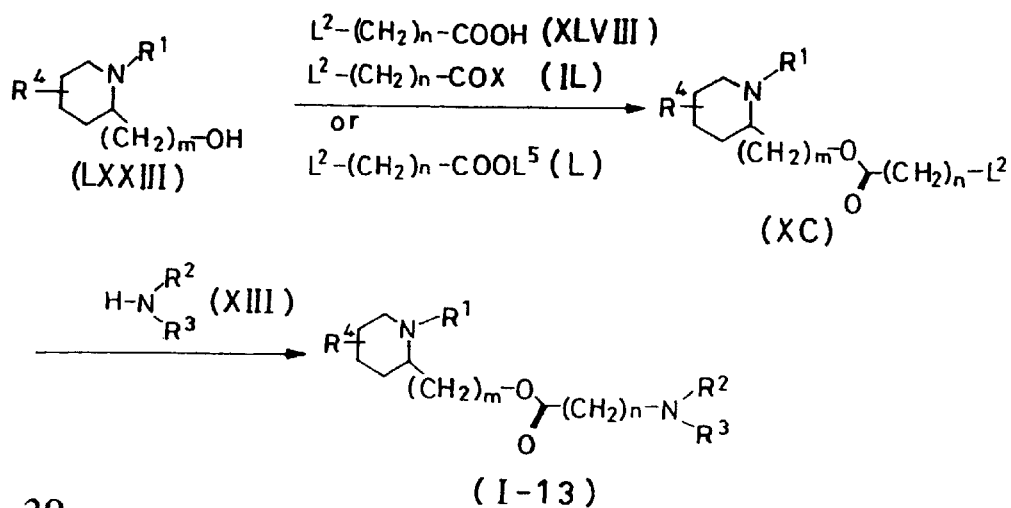
Figure 39:
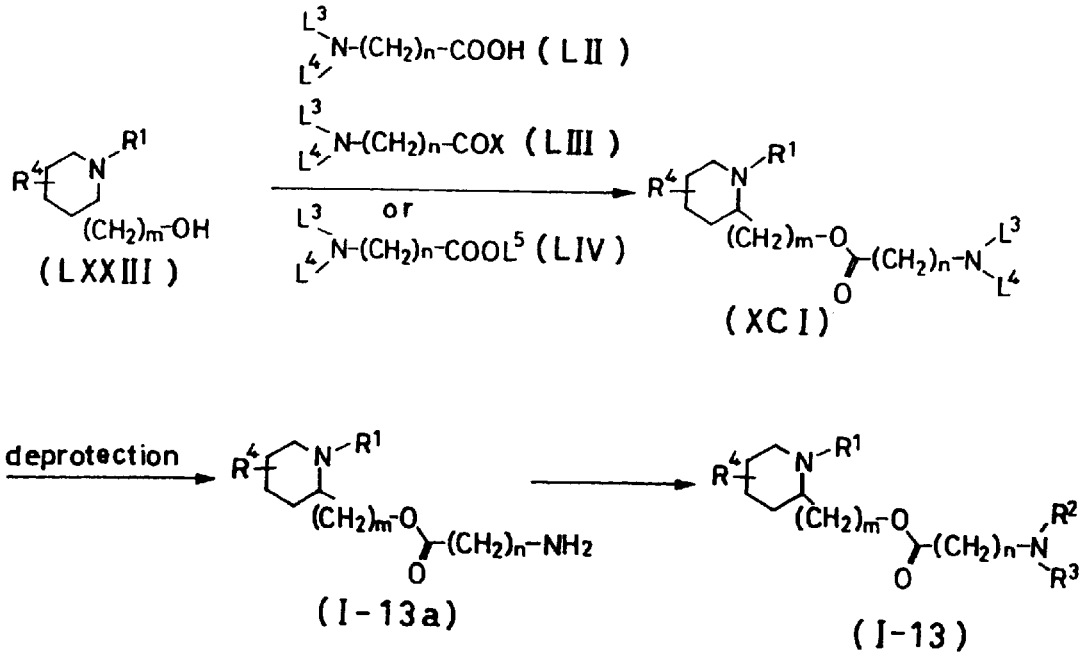
Figure 42:
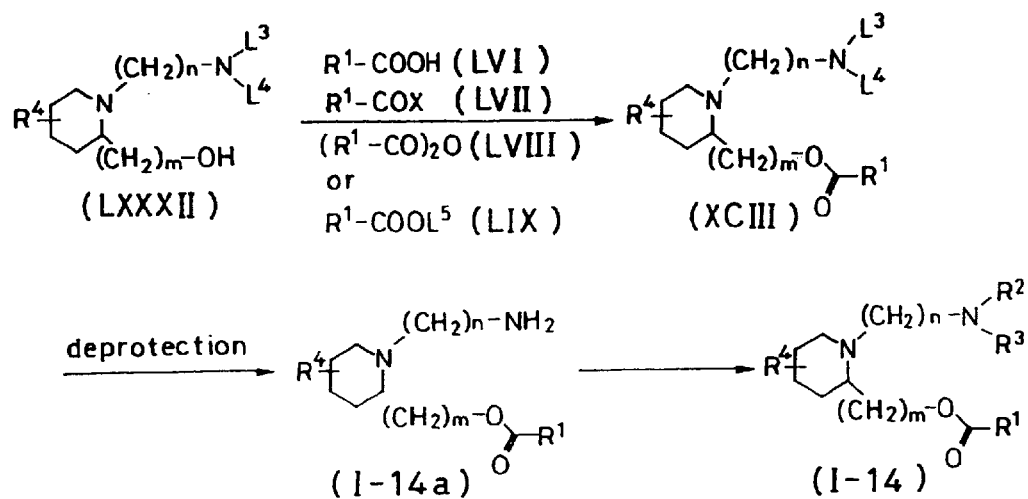
Figure 43:
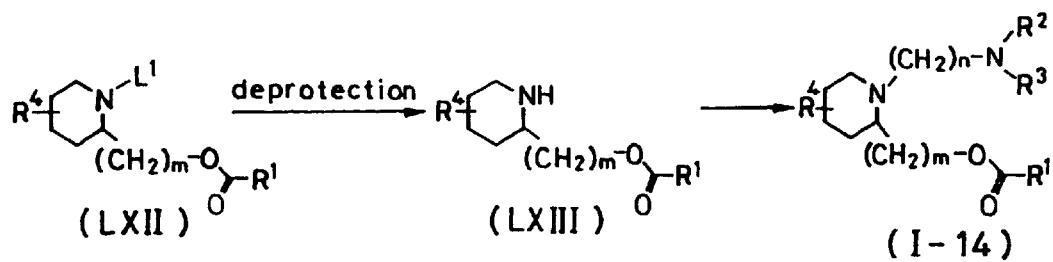

Compound (I-13), for example, can be synthesized as shown in Reaction Formulae GA to GC of FIGS. 37 to 39.
In Reaction Formulae GA to GC, Compound (I-13) can be obtained by reacting with the use of Compound (LXXXIII) obtained in said Reaction Formula EA in the place of the starting material (IV) in said Reaction Formulae CA to CC.

On the other hand, Compound (I-14) can be synthesized as shown in Reaction Formulae GD to GG of FIGS. 40 to 43.
In Reaction Formulae GD to GF, Compound (I-14) can be obtained by reacting with the uses of Compounds (LXXIX), (LXXX) and (LXXXII) in the place of the starting materials (VII), (XXI) and (XXV) in said Reaction Formulae CD to CF, respectively.

In Reaction Formula GG, Compound (I-14) can be obtained from Compound (LXII) by way of Compound (LXIII) in the similar manner to Reaction Formula EG.

Compounds (I-15) and (I-16) (l=0, Z=—NR$^6$—)

(I-15)

(I-16)

Compound (I-15), for example, can be synthesized as shown in Reaction Formulae HA to HB of FIGS. 44 to 45.
In Reaction Formulae HA to HB, the present invention's Compound (I-15) can be obtained by reacting with use of Compounds (LXXIII) and (XCIV) in the place of the starting materials (IV) and (LXV) in said Reaction Formulae DA to DB, respectively.

Figure 46:
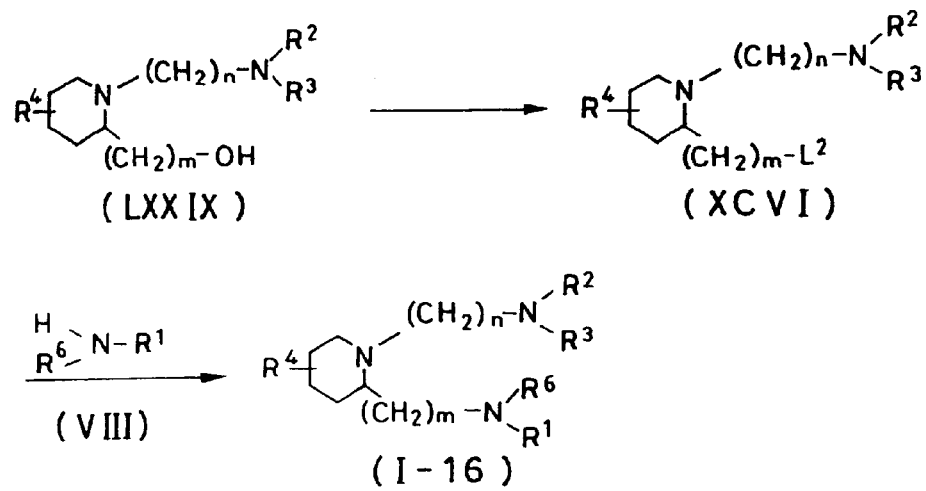
Figure 47:
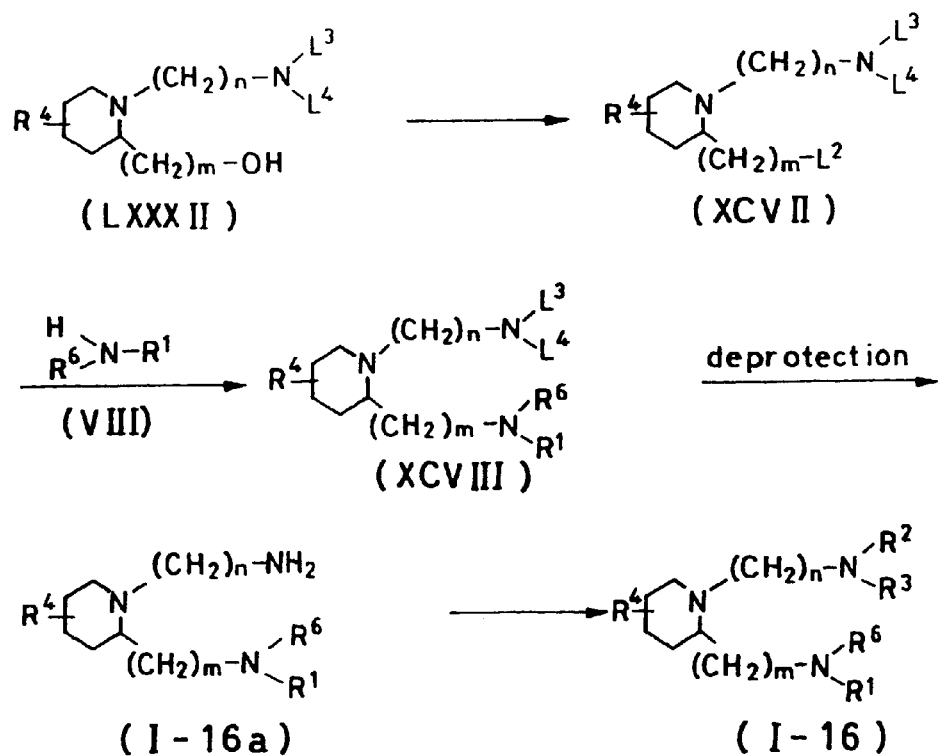
Figure 48:
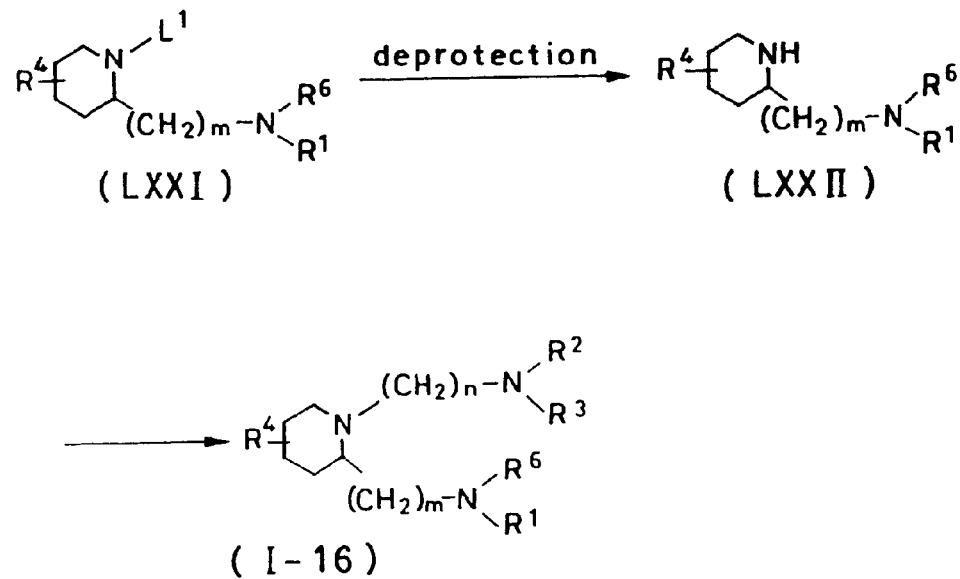

On the other hand, Compound (I-16) can be synthesized as shown in Reaction Formulae HC to HE of FIGS. 46 to 48.
In Reaction Formulae HC to HD, the present invention's Compound (I-16) can be obtained by reacting with the uses of Compounds (LXXIX) and (LXXXII) in the place of the starting materials (VII) and (XXV) in said Reaction Formulae DC to DD, respectively.

In Reaction Formula HE, Compound (I-16) can be obtained from Compound (LXXI) by way of Compound (LXXII) in the similar manner to Reaction Formula EG.

Compounds (I-17) and (I-18) (l=1, Y=—CO—, Z=—OCONR$^6$—)

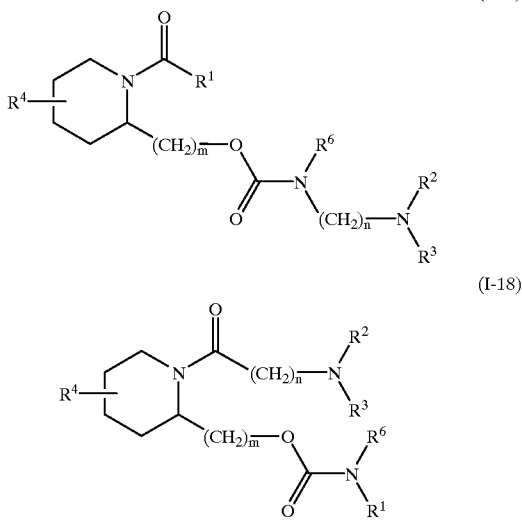

Figure 49:
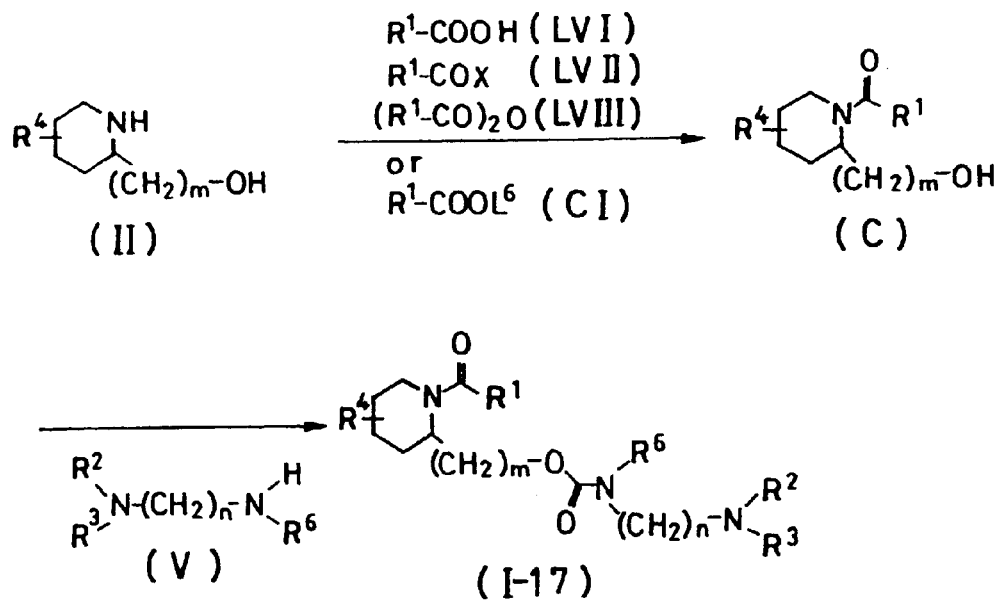
Figure 50:
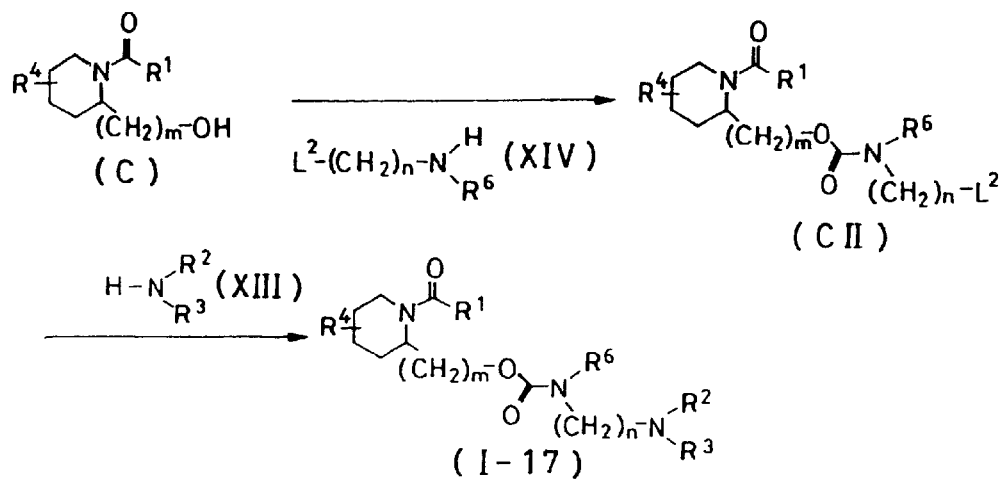
Figure 51:
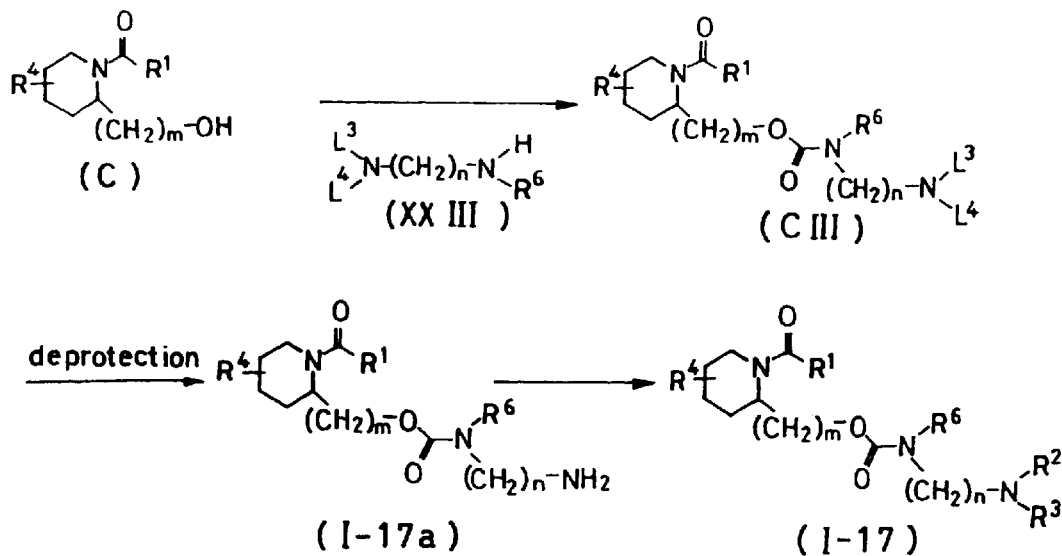

Compound (I-17), for example, can be synthesized as shown in Reaction Formulae IA to IC of FIGS. 49 to 51.

In Reaction Formula IA of FIG. 49, amide (C) is synthesized by acylating an amino group of Compound (II) and then reacted with amine (V), to obtain Compound (I-17). The acylation reaction at the first step can be effected by the reaction of Compound (II) with carboxylic acid (LVI), acid halide (LVII), acid anhydride (LVIII) or mixed acid anhydride (CI) or the like.

In condensation reaction of Compound (II) with carboxylic acid (LVI), for example, a carbodiimide such as N,N'-dicyclohexylcarbodiimide (DCC) or 1-(3-dimethylaminopropyl)-3-ethylcarbodiimide hydrochloride (WSCI); a carbonyldiimidazole such as 1,1'-carbonyldiimidazole; or a chloride such as titan tetrachloride or silicon tetrachloride can be used as a condensing agent. As a solvent, a halogenated hydrocarbon such as dichloromethane or chloroform; an aromatic such as benzene, toluene, xylene or pyridine; an ether such as tetrahydrofuran or 1,4-dioxane; or an amide such as N,N-dimethylformamide or N,N-dimethylacetamide can be used. This reaction may be effected by adding 1-hydroxybenzotriazole (HOBt), N-hydroxysuccinimide (HOSu) or the like as occasion demands. While the reaction temperature and reaction time may be changed according to the starting materials used, the reaction is usually effected at a temperature within the range of −78° C. to the reflux temperature of the solvent.

Also, carboxylic acid (LVI) may be converted into its corresponding azide by using an activator such as diphenylphosphoryl azide and then reacted with Compound (II) (Azide method). As an additive, for example, an organic base such as triethylamine, pyridine or N-methylmorpholine can be used. As a solvent, a halogenated hydrocarbon such as dichloromethane or chloroform; an aromatic such as benzene, toluene, xylene or pyridine; an ether such as tetrahydrofuran or 1,4-dioxane; an amide such as N,N-dimethylformamide or N,N-dimethylacetamide; or a sulfoxide such as dimethylsulfoxide can be used. While the reaction temperature and reaction time may be changed according to the starting materials used, the reaction is usually effected at a temperature within the range of 0° C. to the reflux temperature of the solvent.

In the case where acid halide (LVII) or acid anhydride (LVIII) is used, these compounds are reacted with Compound (II) in the presence of an organic base such as triethylamine, pyridine or N-methylmorpholine, an inorganic base such as sodium hydroxide or a salt such as sodium acetate or potassium carbonate. As a solvent, a halogenated hydrocarbon such as dichloromethane or chloroform; an aromatic such as benzene, toluene, xylene or pyridine; an ether such as diethylether, tetrahydrofuran or 1,4-dioxane; an amide such as N,N-dimethylformamide or N,N-dimethylacetamide; a sulfoxide such as dimethylsulfoxide; water; or a mixed solvent thereof can be used. While the reaction temperature and reaction time may be changed according to the starting materials used, the reaction is usually effected at a temperature within the range of 0° C. to the reflux temperature of the solvent.

In mixed acid anhydride method, after carboxylic acid (LVI) is converted into its corresponding mixed acid anhydride (CI) by using an activator such as ethyl chloroformate, isobutyl chloroformate, pivaloyl chloride, diphenylphosphinic chloride or phosphorus oxychloride, the mixed acid anhydride is reacted with Compound (II). As an additive, for example, an organic base such as triethylamine, pyridine or N-methylmorpholine can be used. As a solvent, a halogenated hydrocarbon such as dichloromethane or chloroform; an aromatic such as benzene, toluene, xylene or pyridine; an ether such as tetrahydrofuran or 1,4-dioxane; an amide such as N,N-dimethylformamide or N,N-dimethylacetamide; or a sulfoxide such as dimethylsulfoxide can be used. While the reaction temperature and reaction time may be changed according to the starting materials used, the reaction is usually effected at a temperature within the range of −15° C. to the reflux temperature of the solvent. $L^6$ in mixed acid anhydride (CI) represents a group corresponding to said activator. For example, ethoxycarbonyl, isobutyloxycarbonyl, pivaloyl group or the like can be used therefor. The definition of $L^6$ is the same in the following.

Specifically, when a condensing agent is used, for example, HOBt or WSCI is added to N,N-dimethylformamide solution of Compound (I) and carboxylic acid (LVI) and then the reaction is effected at a temperature within a range of 0° C. to room temperature, thereby attaining the aimed object.

The reaction at the second step in Reaction Formula IA can be effected according to the second step of said Reaction Formula AA.

In Reaction Formula IB of FIG. 50, Compound (I-17) can be obtained by reacting Compound (C) obtained by said Reaction Formula IA, with amine (XIV) and (XIII) successively. The reaction at the first step in this Reaction Formula can be effected according to the second step of said Reaction Formula AF, while the reaction of the second step can be effected according to said Reaction Formula AC.

In Reaction Formula IC of FIG. 51, amino protecting compound (CIII) is synthesized from Compound (C) and amine (XXIII) and then deprotected to obtain Compound (I-17a) wherein both $R^2$ and $R^3$ are hydrogen atoms. The reaction of the first step in this Reaction Formula can be effected according to the second step of said Reaction Formula AH, while the deprotection reaction at the second step can be effected according to said Reaction Formula AD.

Further, Compound (I-17a) can be leaded to Compound (I-17) in the similar manner to said Reaction Formula AE.

On the other hand, Compound (I-18) can be synthesized as shown in Reaction Formulae ID to IG of FIGS. 52 to 55.

Figure 52:
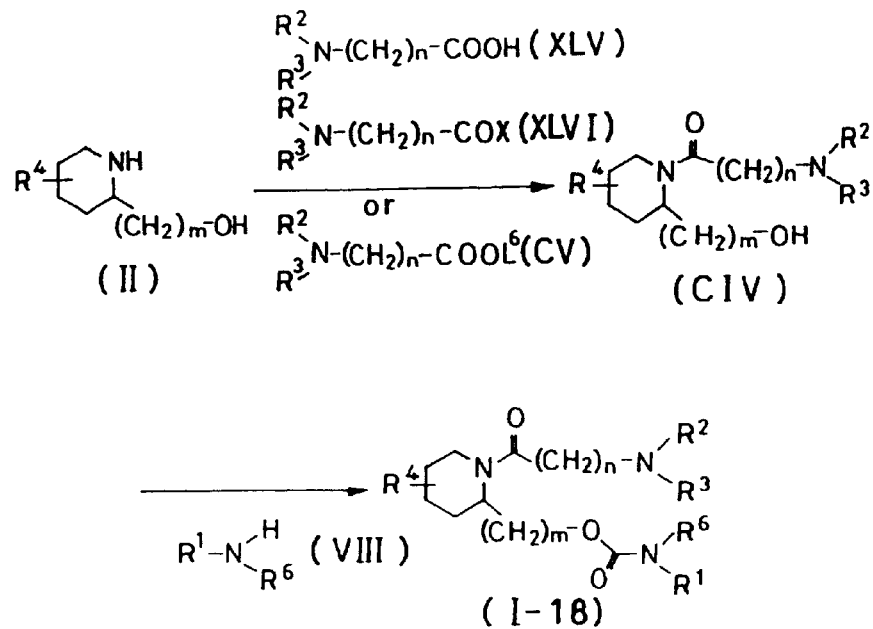

In Reaction Formula ID of FIG. 52, Compound (CIV) is synthesized by acylating an amino group of Compound (II) and then reacted with amine (VIII) to obtain Compound (I-18). The acylation reaction at the first step of Reaction Formula ID can be effected according to said Reaction Formula IA, while the reaction of the second step can be effected according to the second step of said Reaction Formula AA.

Figure 53:
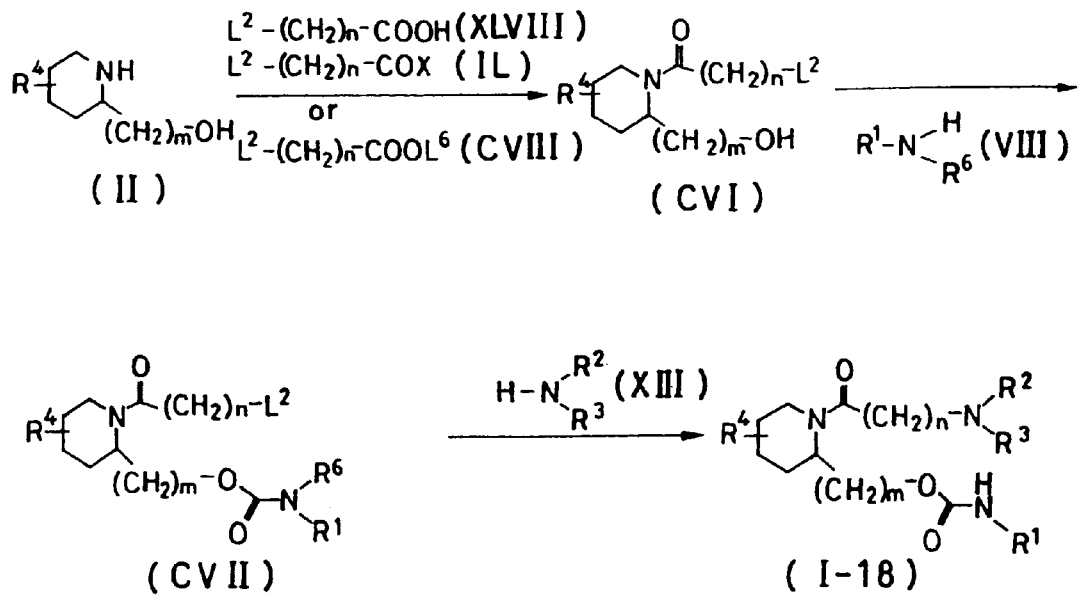

In Reaction Formulae IE of FIG. 53, Compound (CVII) is synthesized from Compound (II) in the similar manner to said Reaction Formula ID, and then reacted with amine (XIII) according to said Reaction Formula AC, thereby obtaining Compound (I-18).

Figure 54:
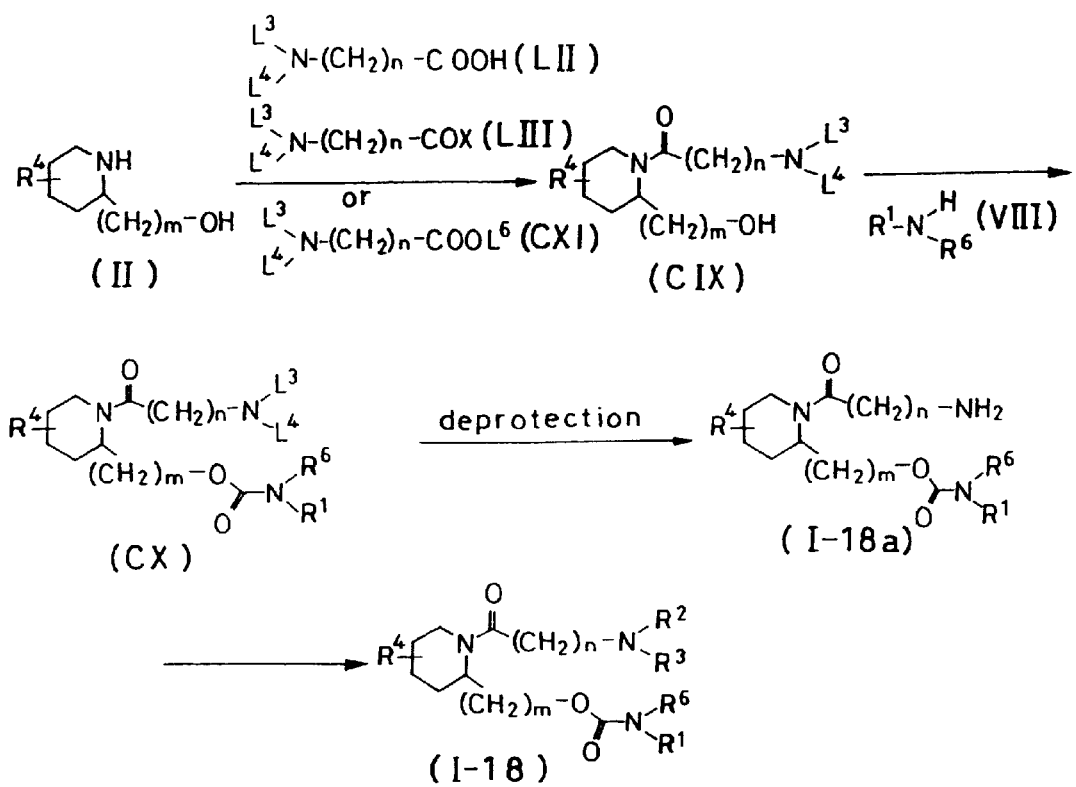

In Reaction Formula IF of FIG. 54, Compound (CX) is synthesized from Compound (II) in the similar manner to Reaction Formula ID, and then deprotected according to said Reaction Formula AD, thereby obtaining Compound (I-18a) wherein both $R^2$ and $R^3$ are hydrogen atoms. Further, Compound (I-18a) can be leaded to Compound (I-18) in the similar manner to said Reaction Formula AE.

Figure 55:
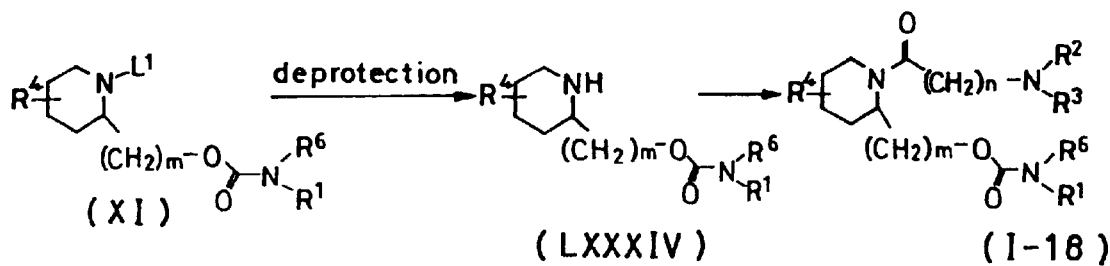

As shown in Reaction Formula IG of FIG. 55, Compound (I-18) also can be synthesized by using Compound (XI) obtained in said Reaction Formula AB as a starting material. Namely, Compound (LXXXIV) is synthesized from Compound (XI) according to deprotection reaction at the second step in said Reaction Formula AB. Then, Compound (LXXXIV) can be leaded to Compound (I-18) by reactions according to: the first step of Reaction Formula ID; the first and third steps of Reaction Formula IE; or the first, third and forth steps of Reaction Formula IF.

Compounds (I-19) and (I-20) (l=1, Y=—CO—, Z=—O—)

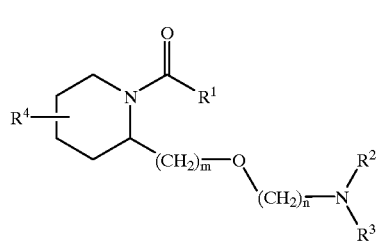
(I-19)

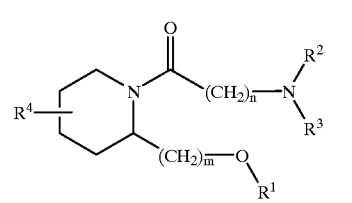
(I-20)

Figure 56:
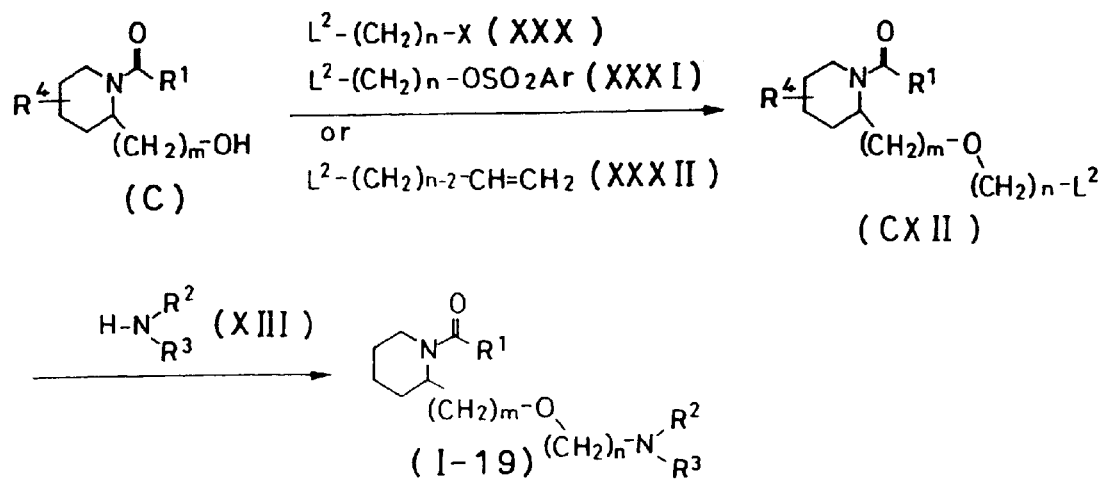
Figure 57:
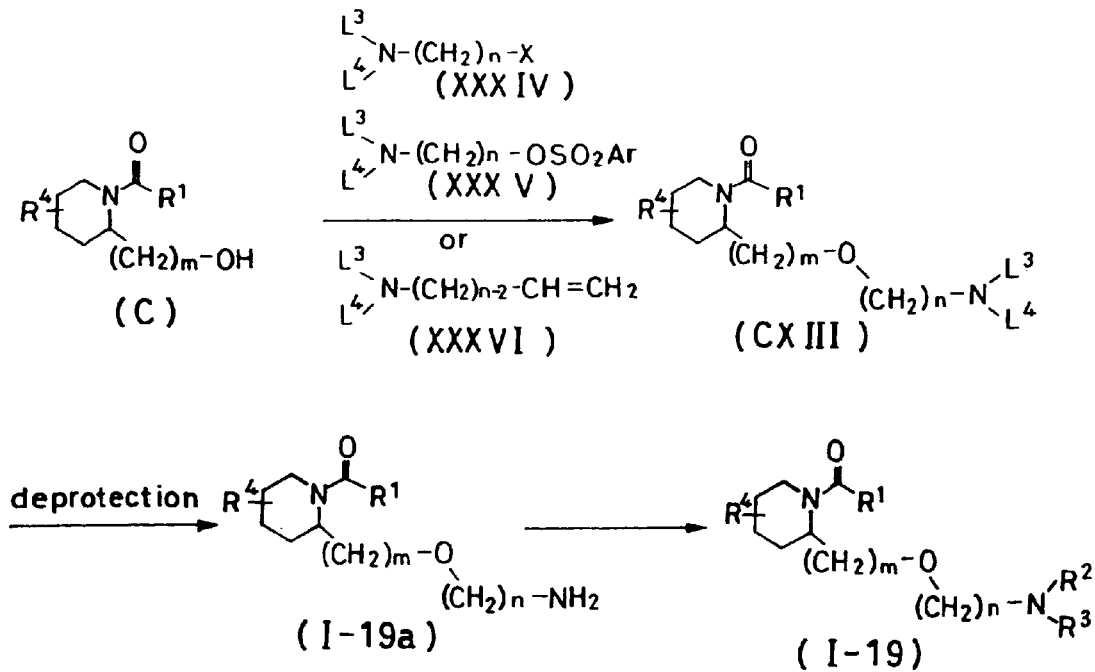

Compound (I-19), for example, can be synthesized as shown in Reaction Formulae JA to JB of FIGS. 56 to 57.

In Reaction Formulae JA to JB, Compound (I-19) can be obtained by reacting with the use of Compound (C) obtained in said Reaction Formula IA in the place of the starting material (IV) in said Reaction Formulae BA to BB.

Figure 58:
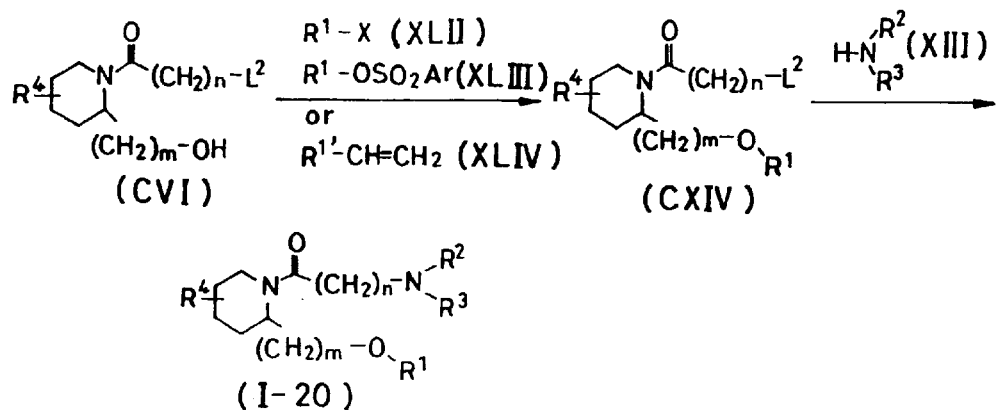
Figure 59:
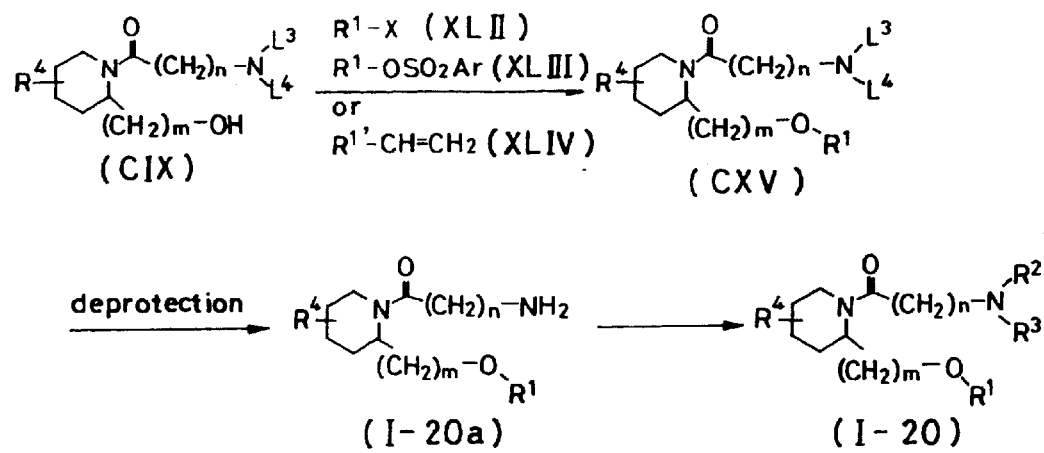
Figure 60:
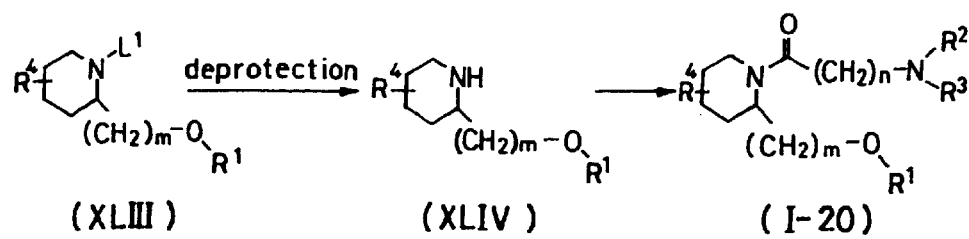
Figure 66:
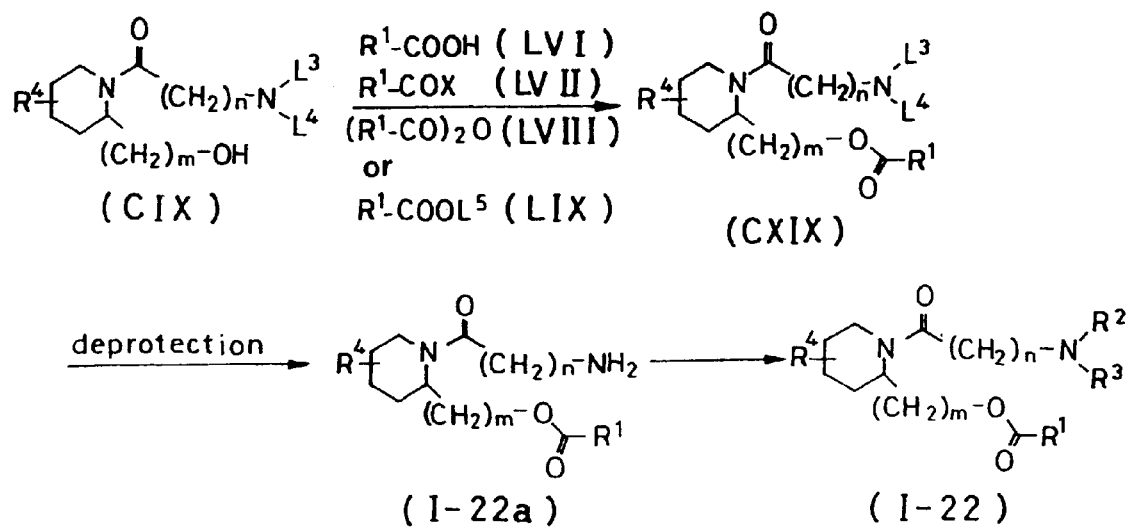
Figure 67:
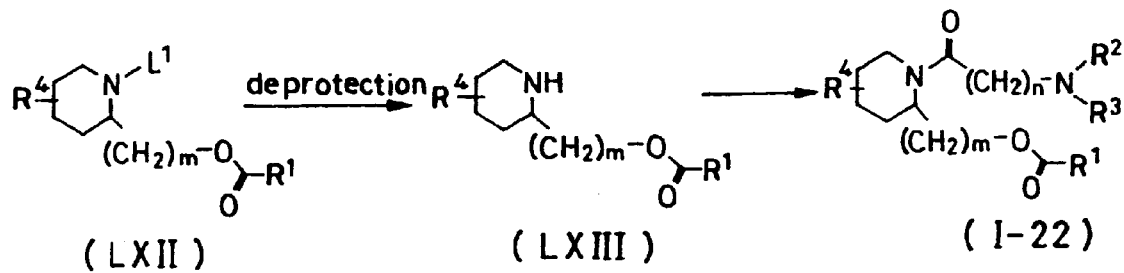

On the other hand, Compound (I-20) can be synthesized as shown in Reaction Formulae JC to JE of FIGS. 58 to 60.

In Reaction Formulae JC to JD, Compound (I-20) can be obtained by reacting with the uses of Compounds (CVI) and (CIX) in the places of the starting materials (XXI) and (XXV) in said Reaction Formulae BC to BD, respectively.

In Reaction Formula JE of FIG. 60, Compound (I-20) can be obtained from Compound (XLIII) by way of Compound (XLIV) in the similar manner to said Reaction Formula IG.

Compounds (I-21) and (I-22) (l=1, Y=—CO—, Z=—OCO—)

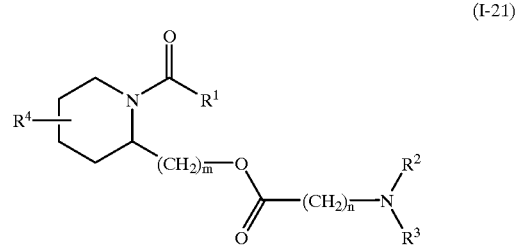
(I-21)

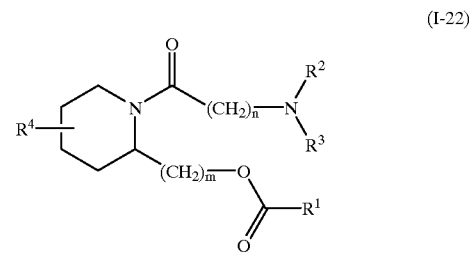
(I-22)

Compound (I-21), for example, can be synthesized as shown in Reaction Formulae KA to KC of FIGS. 61 to 63.

In Reaction Formulae KA to KC, Compound (I-21) can be obtained by reacting with the use of Compound (C) obtained in said Reaction Formula IA in the place of the starting material (IV) in said Reaction Formulae CA to CC.

On the other hand, Compound (I-22) can be synthesized as shown in Reaction Formulae KD to KG of FIGS. 64 to 67.

In Reaction Formulae KD to KF, Compound (I-22) can be obtained by reacting with the uses of Compounds (CIV), (CVI) and (CIX) in the places of the starting materials (VII), (XXI) and (XXV) in said Reaction Formulae CD to CF, respectively.

In Reaction Formula KG, Compound (I-22) can be obtained from Compound (LXII) by way of Compound (LXIII) in the similar manner to Reaction Formula IG.

Compounds (I-23) and (I-24) (l=0, Y=—CO—, Z=—$NR^6$—)

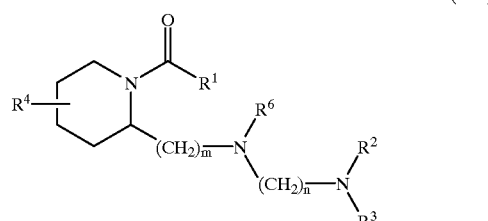
(I-23)

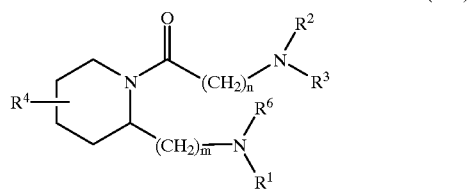

(I-24)

Figure 68:
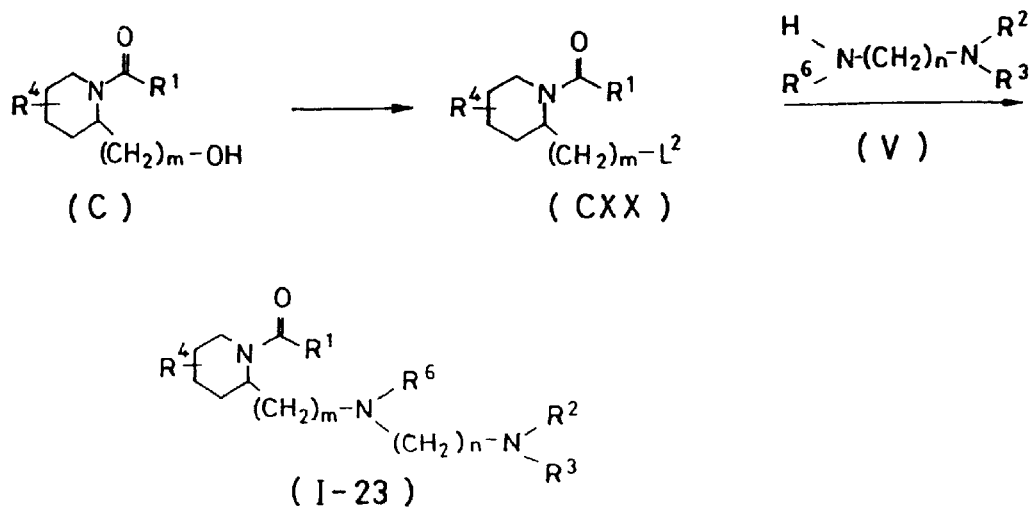
Figure 69:
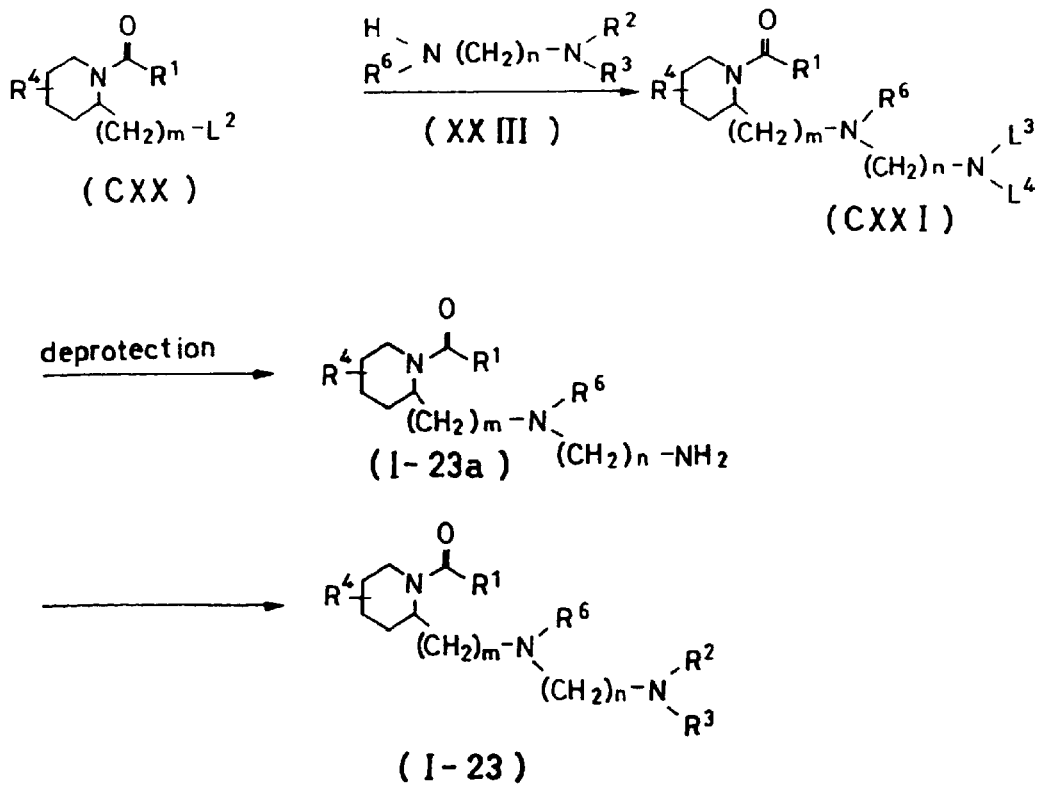

Compound (I-23), for example can be synthesized as shown in Reaction Formulae LA to LB of FIGS. 68 to 69.

In Reaction Formulae LA to LB, Compound (I-23) can be obtained by reacting with the uses of Compounds (C) and (CXX) in the places of the starting materials (IV) and (LXV) in said Reaction Formulae DA to DB, respectively.

On the other hand, Compound (I-24) can be synthesized as shown in Reaction Formulae LC to LE of FIGS. 70 to 72.

In Reaction Formulae LC to LD, Compound (I-24) can be obtained by reacting with the uses of Compounds (CIV) and (CIX) in the places of the starting materials (VII) and (XXV) in said Reaction Formulae DC to DD, respectively.

In Reaction Formula LE, Compound (I-24) can be obtained from Compound (LXXI) by way of Compound (LXXII) in the similar manner to Reaction Formula IG.

Compounds (I-25) and (I-26) (l=1, Y=—COO—, Z=—OCONR$^6$—)

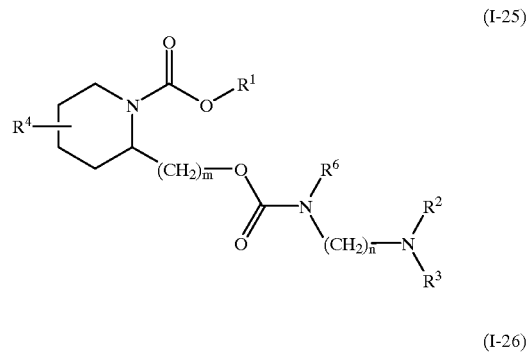

(I-25)

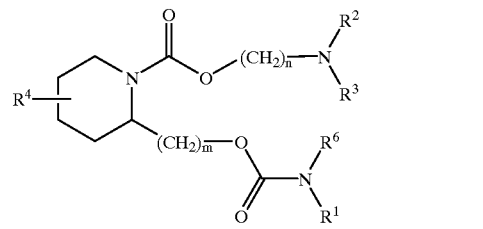

(I-26)

Figure 74:
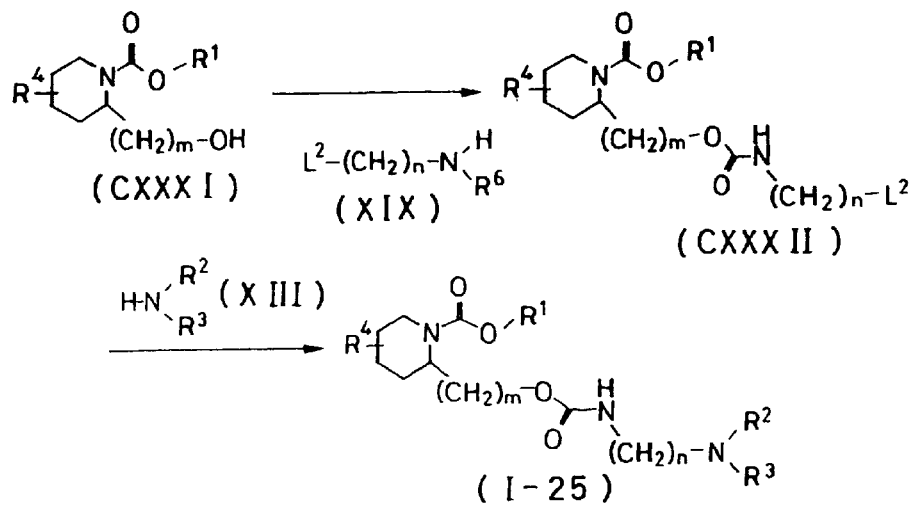
Figure 75:
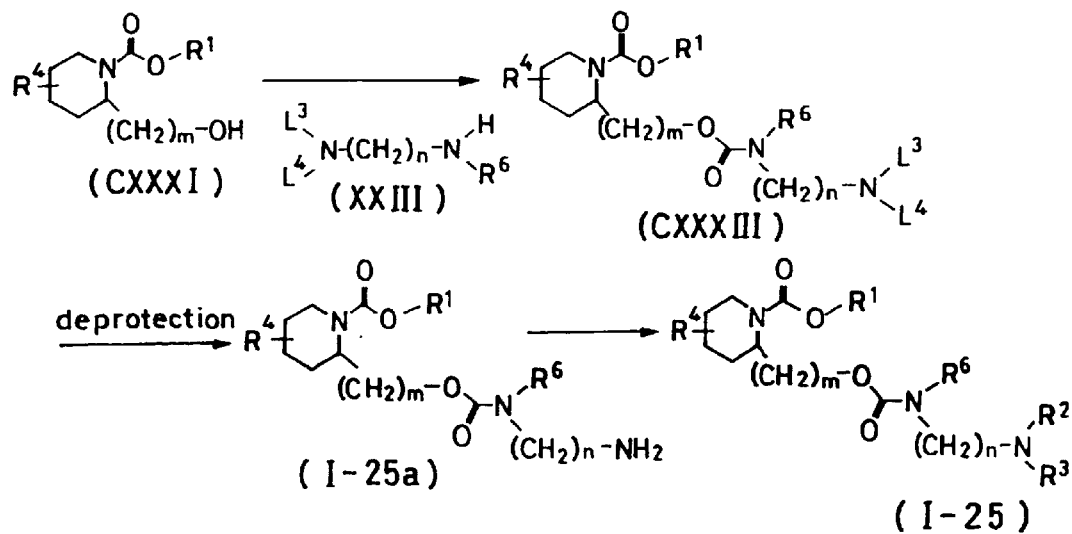

Compound (I-25), for example, can be synthesized as shown in Reaction Formulae MA to MC of FIGS. 73 to 75.

In Reaction Formula MA of FIG. 73, Compound (CXXXI) is synthesized from Compound (II) and alcohol (CXXX) and then reacted with amine (V), thereby obtaining Compound (I-25).

In the reaction at the first step in Reaction Formula MA, by using phenyl chlorocarbonate, phosgene, diphosgene, triphosgene, di-2-pyridylketone or the like, alcohol (CXXX) is converted into its corresponding carbonate in the presence of an additive and then the carbonate is reacted with Compound (II), thereby attaining the aimed object. As an additive, for example, a base such as triethylamine, N,N-diisopropylethylamine, pyridine or sodium carbonate can be used. As a solvent, for example, a halogenated hydrocarbon such as dichloromethane or chloroform; an aromatic hydrocarbon such as benzene, toluene or xylene; or an ether such as tetrahydrofuran or 1,4-dioxane can be used. While the reaction temperature and reaction time may be changed according to the starting materials and the reagents used, the reaction is usually effected at a temperature within the range of −15° C. to 200° C. Specifically, for example, by using pyridine or N,N-diisopropylethylamine as an additive, alcohol (CXXX) is reacted with phenyl chlorocarbonate, triphosgene or the like in a solvent such as chloroform or dichloromethane at a temperature within the range of −15° C. to room temperature. The resulting carbonate corresponding to alcohol (CXXX) is reacted with Compound (II) in or without a solvent such as chloroform or dichloromethane at a temperature within the range of room temperature to 100° C., thereby obtaining Compound (CXXXI).

The reaction at the second step in Reaction Formula MA can be effected according to the second step of said Reaction Formula AA.

In Reaction Formula MB of FIG. 74, Compound (I-25) can be obtained by reacting Compound (CXXXI) obtained in said Reaction Formula MA with amine (XIX) and (XIII) successively. The reaction at the first step can be effected according to the second step of said Reaction Formula AF, while the reaction at the second step can be effected according to said Reaction Formula AC.

In Reaction Formula MC of FIG. 75, Compound (CXXXIII) is synthesized from Compound (CXXXI) and amine (XXIII), and then deprotected, thereby obtaining Compound (I-25a) wherein both R$^2$ and R$^3$ are hydrogen atoms. The reaction at the first step can be effected according to the second step of said Reaction Formula AH, while the deprotection reaction of the second step can be effected according to said Reaction Formula AD.

Further, Compound (I-25a) can be leaded to Compound (I-25) in the similar manner to said Reaction Formula AE.

On the other hand, Compound (I-26) can be synthesized as shown in Reaction Formulae MD to MG of FIGS. 76 to 79.

In Reaction Formula MD of FIG. 76, Compound (CXXXV) is synthesized from Compound (II) and alcohol (CXXXIV) and then reacted with amine (VIII) to obtain Compound (I-26). The reaction at the first step can be effected according to said Reaction Formula MA, while the reaction of the second step can be effected according to the second step of said Reaction Formula AA.

In Reaction Formula ME of FIG. 77, Compound (CXXXVIII) is synthesized from Compound (II) in the similar manner to said Reaction Formula MD and then reacted with amine (XIII) according to Reaction Formula AC, thereby obtaining Compound (I-26).

Figure 78:
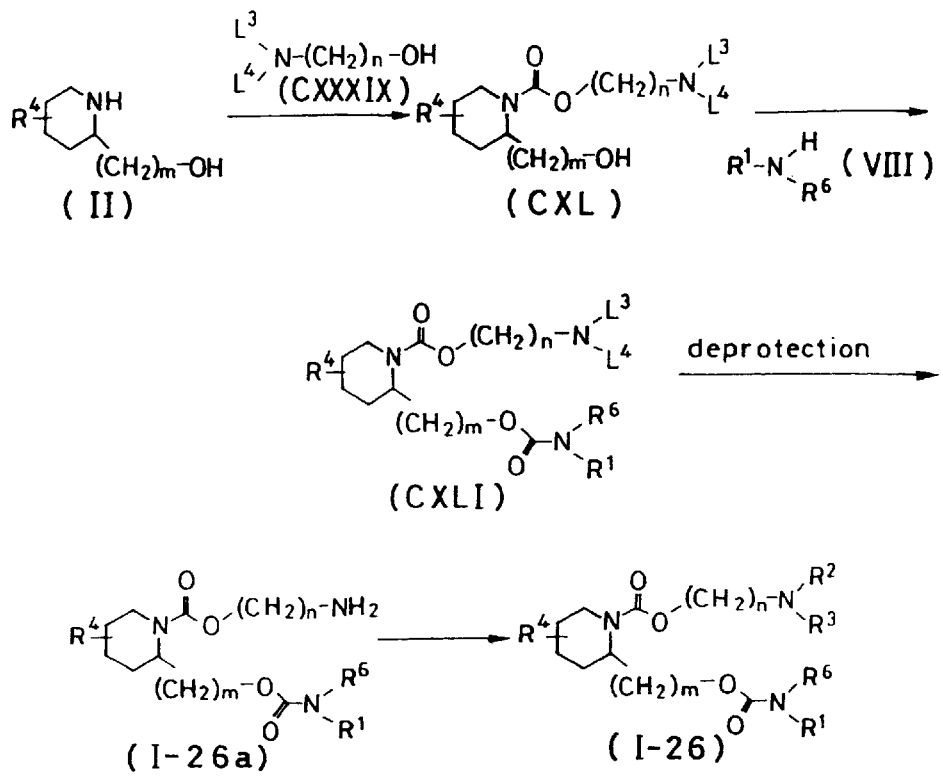

In Reaction Formula MF of FIG. 78, amine (CXLI) is synthesized from Compound (II) in the similar manner to said Reaction Formula MD and then deprotected, thereby obtaining Compound (I-26a) wherein both R$^2$ and R$^3$ are hydrogen atoms. This deprotection reaction can be effected according to said Reaction Formula AD.

Further, Compound (I-26a) can be leaded to Compound (I-26) in the similar manner to said Reaction Formula AE.

Figure 79:
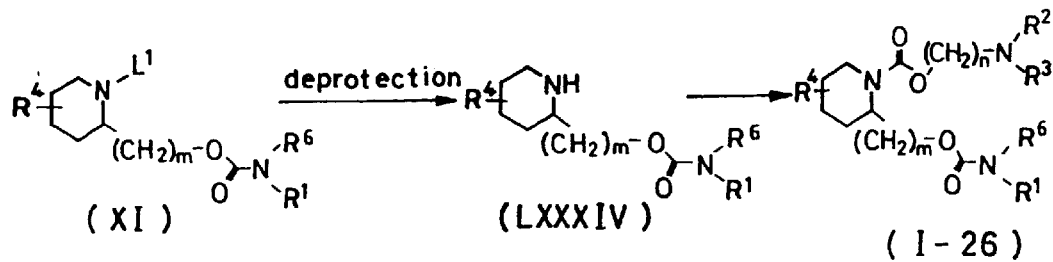

As shown in Reaction Formula MG of FIG. 79, Compound (I-26) also can be synthesized by using Compound (XI) obtained in said Reaction Formula AB as a starting material. Namely, Compound (LXXXIV) is synthesized from Compound (XI) according to the deprotection reaction at the second step in said Reaction Formula AB. Then, Compound (LXXXIV) can be leaded to Compound (I-26) by reactions according to: the first step of Reaction Formula MD; the first and third steps of Reaction Formula ME; or the first, third and forth steps of Reaction Formula MF.

Compounds (I-27) and (I-28) (l=1, Y=—COO—, Z=—O—)

(I-27)

(I-28)

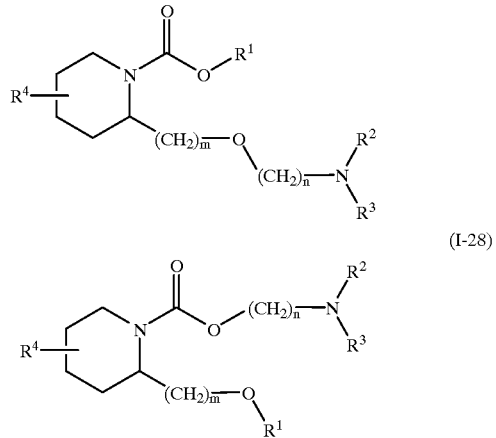

Figure 80:
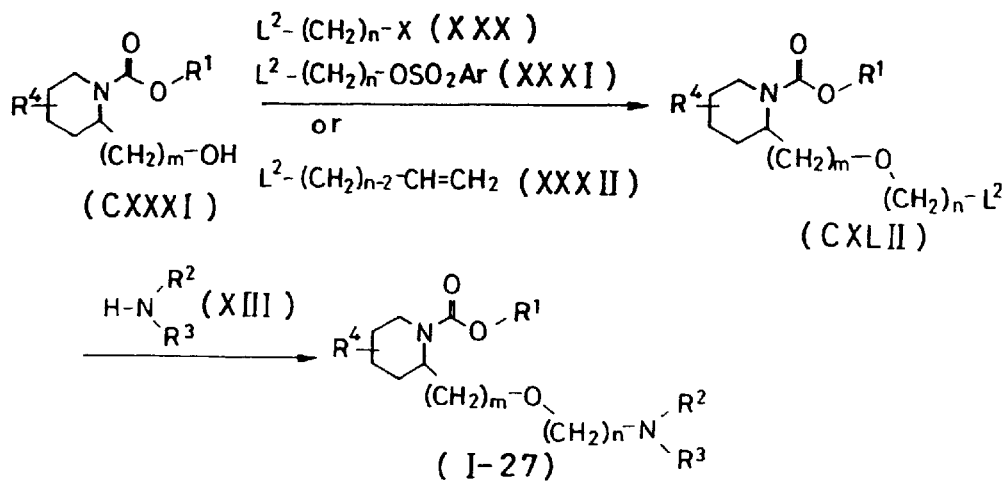
Figure 81:
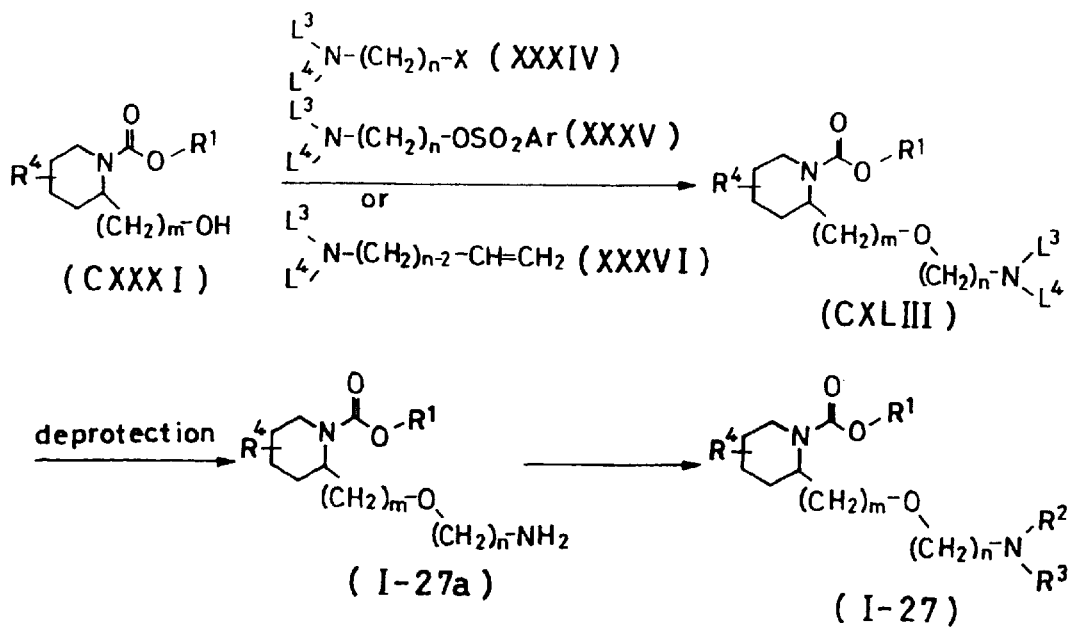

Compound (I-27), for example, can be synthesized as shown in Reaction Formulae NA to NB of FIGS. 80 to 81.

In Reaction Formulae NA to NB, Compound (I-27) can be obtained by reacting with use of Compound (CXXXI) obtained in said Reaction Formula MA in the place of the starting material (IV) in said Reaction Formulae BA to BB.

Figure 82:
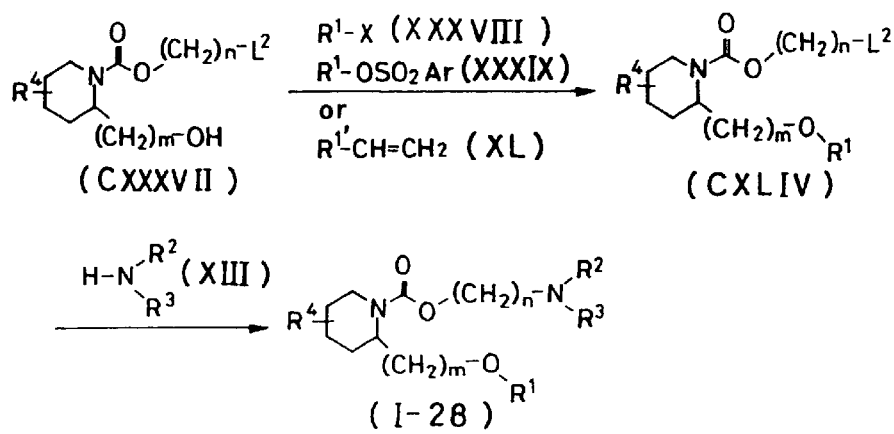
Figure 83:
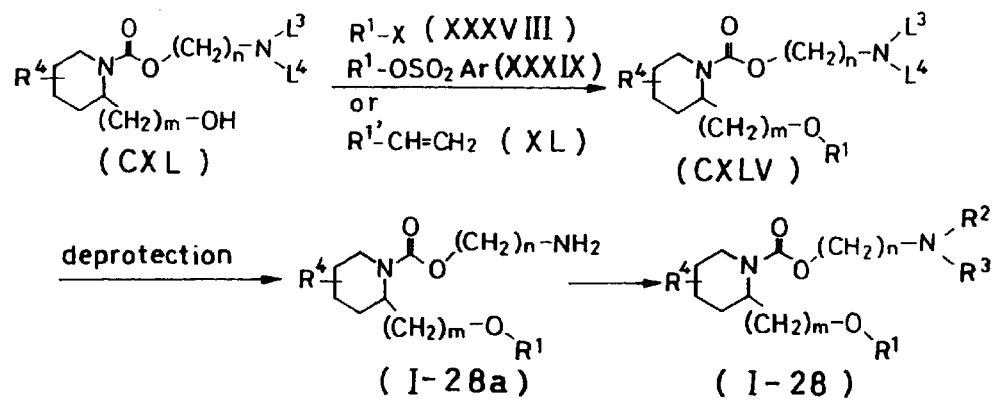
Figure 84:
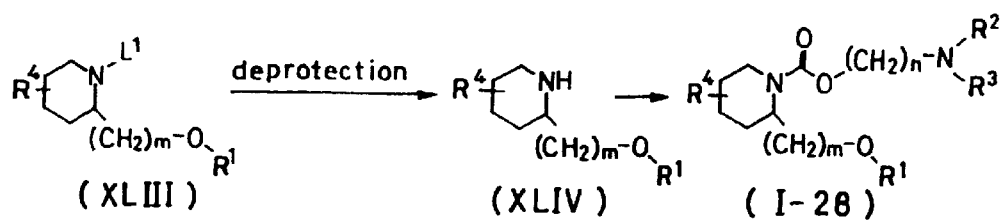

On the other hand, Compound (I-28) can be synthesized as shown in Reaction Formulae NC to NE of FIGS. 82 to 84.

In Reaction Formulae NC to ND, Compound (I-28) can be obtained by reacting with the uses of Compounds (CXXXVII) and (CXL) in the places of the starting materials (XXI) and (XXV) in said Reaction Formulae BC to BD, respectively.

In Reaction Formula NE of FIG. 84, Compound (I-28) can be obtained from Compound (XLIII) by way of Compound (XLIV) in the similar manner to Reaction Formula MG.

Compounds (I-29) and (I-30) (l=1, Y=—COO—, Z=—OCO—)

(I-29)

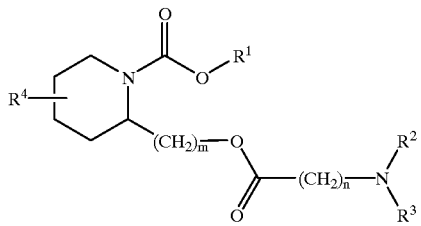

(I-30)

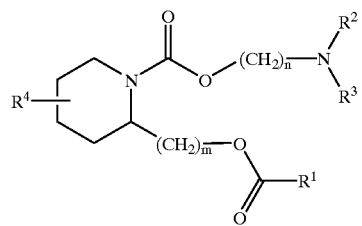

Figure 85:
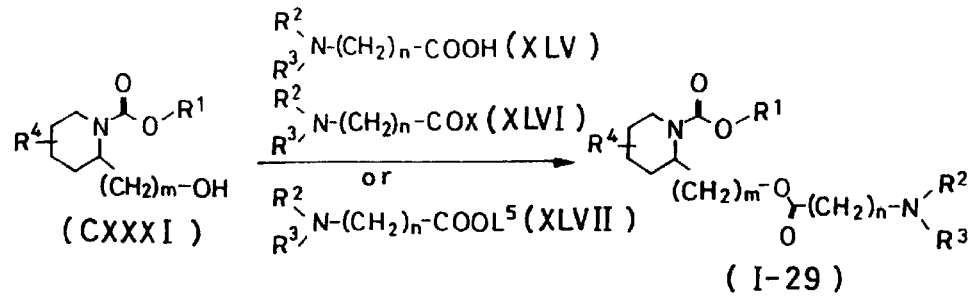
Figure 86:
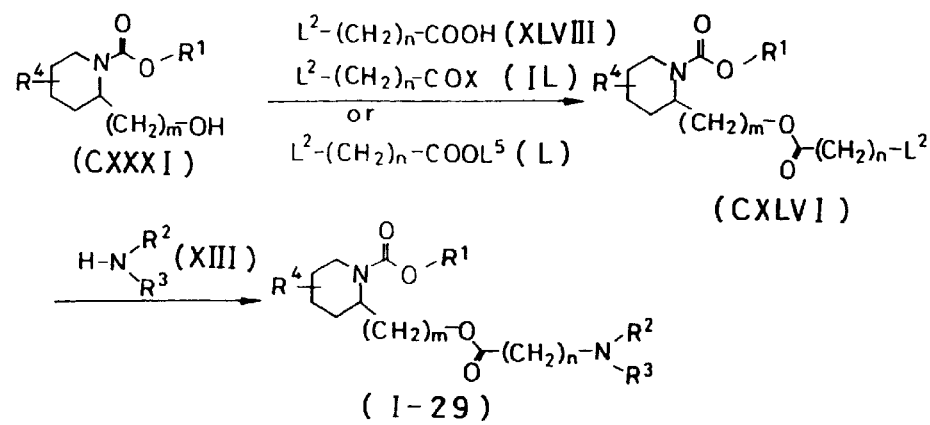
Figure 87:
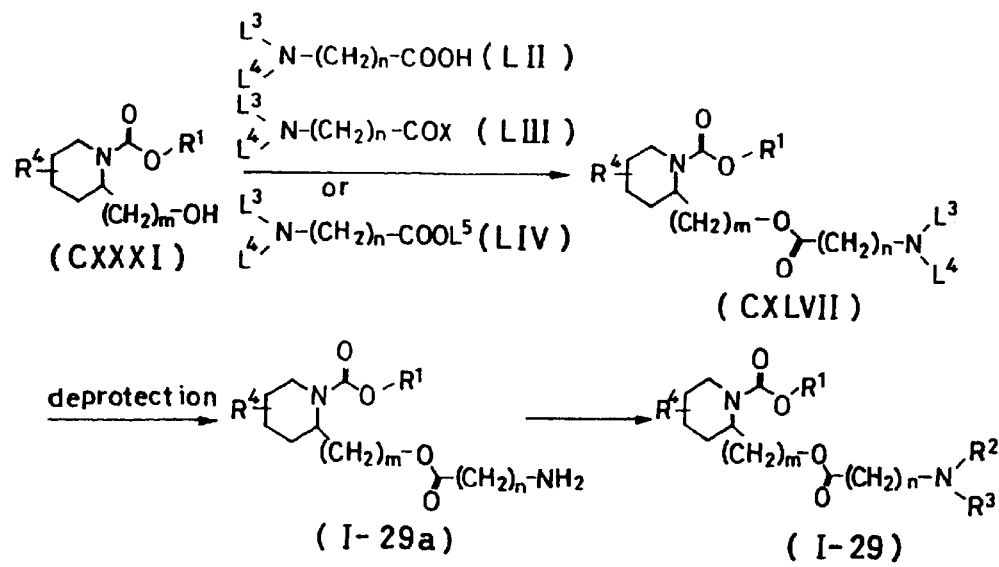
Figure 88:
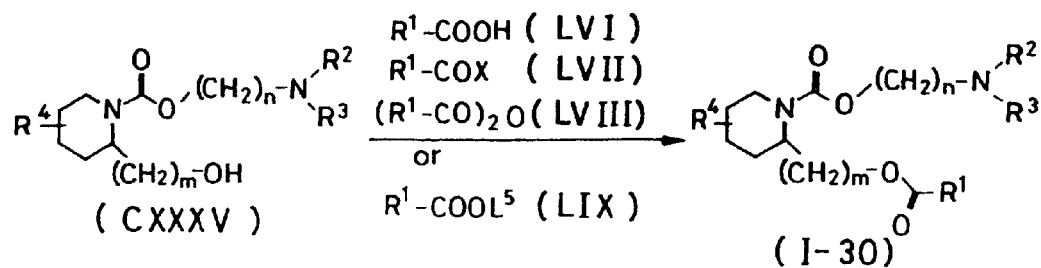
Figure 89:
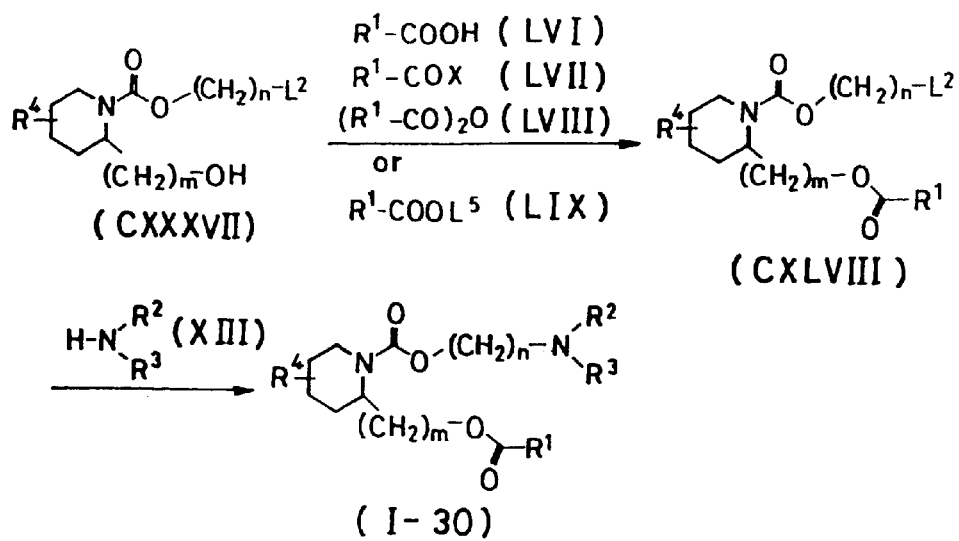
Figure 90:
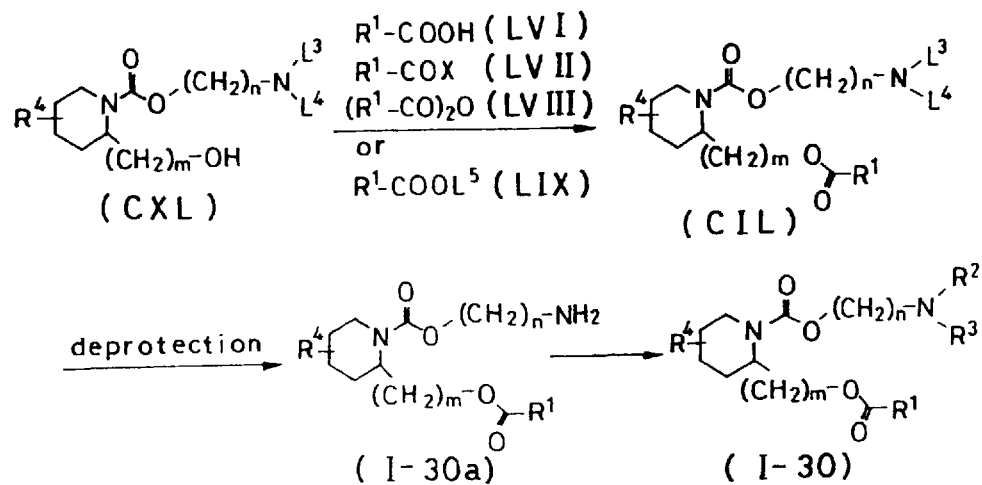
Figure 91:
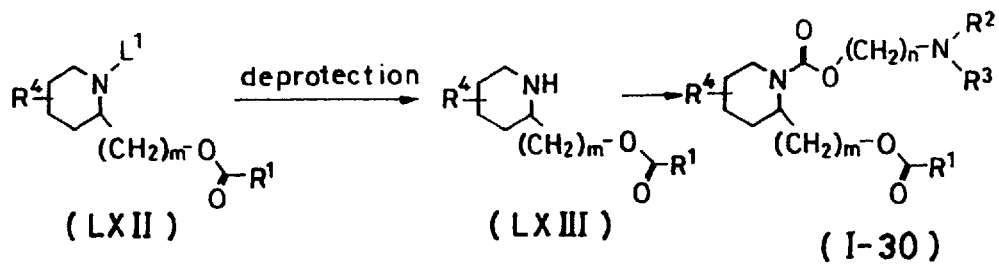

Compound (I-29), for example, can be synthesized as shown in Reaction Formulae OA to OC of FIGS. 85 to 87.

In Reaction Formulae OA to OC, Compound (I-29) can be obtained by reacting with the use of Compound (CXXXI) obtained in said Reaction Formula MA in the place of the starting material (IV) in said Reaction Formulae CA to CC.

On the other hand, Compound (I-30) can be synthesized as shown in Reaction Formulae OD to OG of FIGS. 88 to 91.

In Reaction Formulae OD to OF, Compound (I-30) can be obtained by reacting with the uses of Compounds (CXXXV), (CXXXVII) and (CXL) in the places of the starting materials (VII), (XXI) and (XXV) in said Reaction Formulae CD to CF, respectively.

In Reaction Formula OG, Compound (I-30) can be obtained from Compound (LXII) by way of Compound (LXIII) in the similar manner to Reaction Formula MG.

Compounds (I-31) and (I-32) (l=1, Y=—COO—, Z=—NR$^6$—)

(I-31)

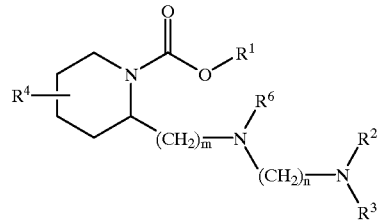

(I-32)

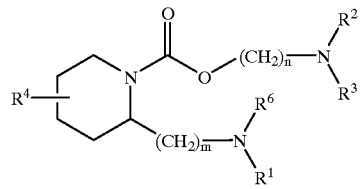

Compound (I-31), for example, can be synthesized as shown in Reaction Formulae PA to PB of FIGS. 92 to 93.

In Reaction Formulae PA to PB, Compound (I-31) can be obtained by reacting with the uses of Compounds (CXXXI) and (CL) in the places of the starting materials (IV) and (LXV) in said Reaction Formulae DA to DB, respectively.

Figure 94:
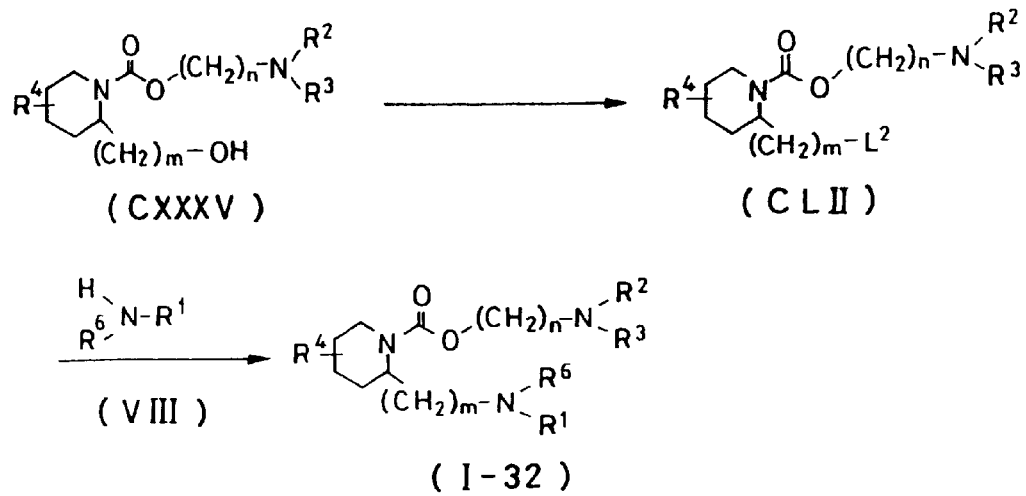
Figure 95:
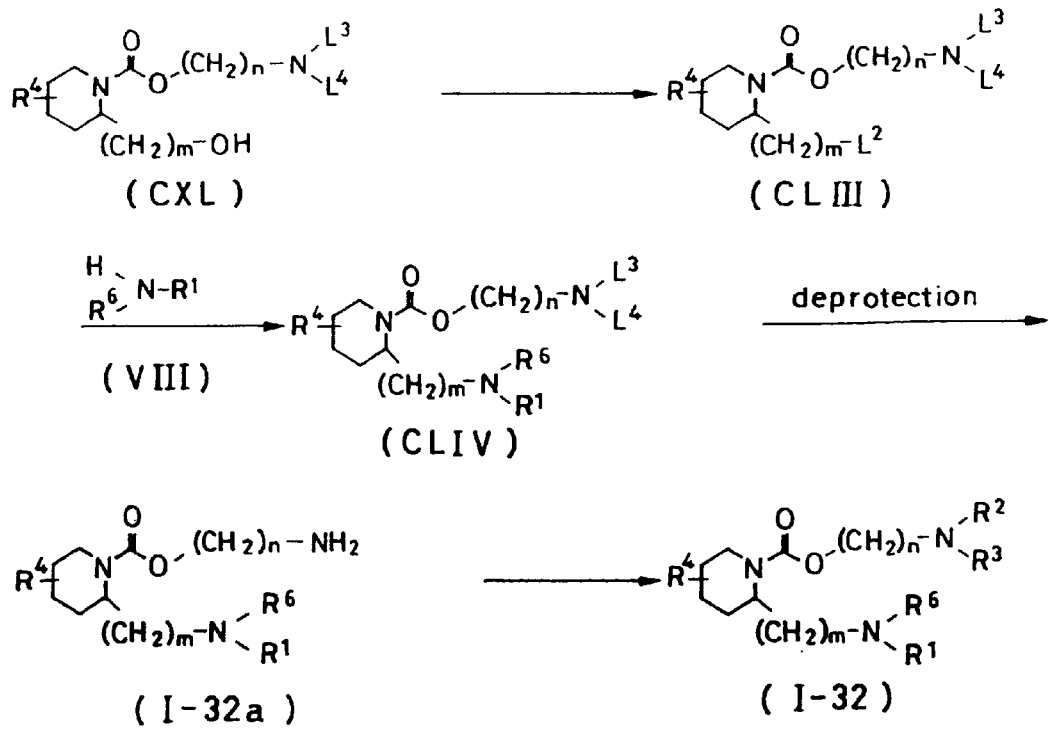
Figure 96:
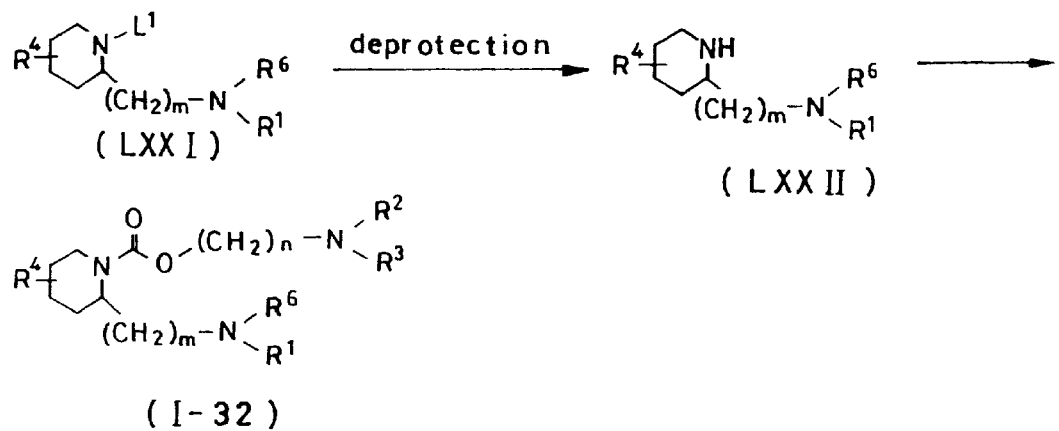

On the other hand, Compound (I-32) can be synthesized as shown in Reaction Formulae PC to PE of FIGS. 94 to 96.

In Reaction Formulae PC to PD, Compound (I-32) can be obtained by reacting with the uses of Compounds (CXXXV) and (CXL) in the places of the starting materials (VII) and (XXV) in said Reaction Formulae DC to DD, respectively.

In Reaction Formula PE, Compound (I-32) can be obtained from Compound (LXXI) by way of Compound (LXXII) in the similar manner to Reaction Formula MG.

Among the starting materials used in the foregoing Reaction Formulae, materials which are not described above are commercially available or can be easily synthesized from a suitable starting material by using known methods.

The 1,2-di-substituted piperidine derivative (I) provided in the present invention can be changed to an acid-added salt if necessary. Examples of the acid-added salt include salt with an inorganic acid such as hydrochloric acid, hydrobromic acid, sulfuric acid or phosphoric acid and salts with an organic acid such as acetic acid, propionic acid, citric acid, lactic acid, oxalic acid, maleic acid, fumaric acid, succinic acid, tartaric acid or methanesulfonic acid. These salts can be easily manufactured by common methods.

The 1,2-di-substituted piperidine derivatives in accordance with the present invention, which mechanism of action has not been made clear, have an excellent hair growth and regrowth promoting effect. Accordingly, by applying the compound on skin of mammals such as human scalp, care, improvement, or prevention of hair loss can be expected.

The 1,2-di-substituted piperidine derivative of the present invention can apply to pathological alopecia such as alopecia areata, alopecia pityrodes or alopecia seborrheica in addition to thin hair or hair loss what is called male pattern baldness or androgenic alopecia. The dosage of the 1,2-di-substituted piperidine derivative in accordance with the present invention must be determined suitably according to sex, age and degree of symptom in hair loss or thin hair. Usually 0.01–20 mg/cm$^2$ is applied on scalp per day for an adult in a single dose or several doses.

When the 1,2-di-substituted piperidine derivative of the present invention is used as a drug, quasi-drug or cosmetic for hair growth and regrowth promoting and prevention of hair loss, its pharmaceutical form can be selected voluntarily as long as the effects of the present invention can be exhibited. Examples of the pharmaceutical forms include tonic, lotion, milky lotion, cream, ointment, gel, spray and mousse.

In addition to the 1,2-di-substituted piperidine derivative in accordance with the present invention, various pharmaceutically acceptable ingredients, which are generally compounded to hair growth promoting composition in the field of drug, quasi-drug and cosmetic, can be compounded to these preparations.

For example, as a drug having a blood flow promoting action, swertia herb extract, vitamin E and derivatives thereof, nicotinates such as benzyl nicotinate, and the like can be used. Examples of drugs which promote blood circulation by topical stimulation include capsicum tincture, cantharides tincture, camphor and vanillic acid nonylamide. Examples of drugs having hair follicle activating action include hinokitiol, placental extract, photosensitizing dye, pantothenic acid and derivatives thereof. Examples of drugs having antiandrogen action include a hormone such as estradiol or estrone. Examples of drugs having antiseborrheic action include sulfur, thioxolone and vitamin $B_6$.

In addition, salicylic acid, resorcine and the like which has corneocycle desquamating and antibacterial action can be compounded therein so as to prevent the generation of dandruff. Also, glycyrrhizic acid and derivatives thereof, menthol, and the like can be compounded therein so as to prevent inflammation of scalp. Further, an amino acid such as serine, methionine or arginine, a vitamin such as biotin, extracts of crude drugs and the like can be compounded therein in order to supplement nutrition for hair follicle and activate enzyme activity.

Also, extracts from plants such as althea, coix, peppermint, leaf base, capsicum, aloe, lycium, mugwort, oryza, seashore vitex, rosmarinus officinalis, drynaria, cytisus scoparius, gentiana, salviae miltiorrhizeae radix, sponge gourd, platycodon, pinus, sophora root, Japanese angelica root, safflower, Japanese barberry, areca, eucalyptus, prunella spike, akebia stem, achyranthes root, bupleurum root, tea, licorice, hop, Chrysanthemum, senega, sesame, cnidium rhizome, cashew, pueraria root, rosae rugosae flos, saffron, rosemary, rehmannia root, or mallow can be compounded.

Also, a vasodilator such as alkoxycarbonylpyridine N-oxide, carpronium chloride or acetylcholine derivative; a cutaneous hyperfunctioning agent such as cephalanthin; an antibacterial agent such as hexachlorophene, benzalkonium chloride, cetylpyridinium chloride, undecylenic acid, trichlorocarbanilide or bithionol; zinc and its derivatives; lactic acid and its alkyl ester; an organic acid such as citric acid; a protease inhibitor such as tranexamic acid; and the like can be compounded.

Further, an alcohol such as ethanol or isopropyl alcohol; a polyvalent alcohol such as glycerine, propylene glycol or polyethylene glycol; an oily ingredient such as higher fatty acids, higher alcohols, hydrogenated castor oils, natural oils and fats, ester oils or silicone oils; surfactants; perfumes; chelating agents; humectants such as 1,3-butyleneglycol, hyaluronic acid and its derivatives, maltitol, soluble collagen or sodium lactate; thickening agents such as quince mucilage, carboxyvinylpolymer or xanthan gum; antioxidants; ultraviolet absorbers: coloring agents; water; stabilizers; and the like, which are generally compounded in hair growth composition, can be compounded within the range provided that the effects of the present invention are not spoiled.

EXAMPLES

In the following, the present invention will be explained by using specific examples. However, the present invention should not be restricted thereto.

Hair Regrowth Test (1) Test Method

By using C3H/HeNCrj mice, whose hair cycle was in resting stage, the experiment was performed according to the method of Ogawa et. al. (Normal and Abnormal Epidermal Differentiation, Edited by M. Seiji and I. A. Bernstein, Pages 159–170, 1982, Todai Shuppan). 10 mice were used in a group and the mice's hair within the area of 3×4 cm of the regions of back was shaved by a clipper and a shaver. 0.1 ml of ethanol (negative contrast) or ethanol solution of the tested compound was applied on the shaved portion once a day. For hair regrowth effect of the tested compound, the hair regrowth area of mice's region of back was measured and ratio of the hair regrowth area with respect to the shaved area was evaluated as hair regrowth area rate.

(2) Result

Hair regrowth area rates (%) after the following tested compounds were applied for 17 or 18 days are shown in TABLE 1.

31

Compound 1: N-[3-(Dimethylamino)propyl]-{2-[1-(N-octadecylcarbamoyl)-2-piperidyl]ethoxy}formamide

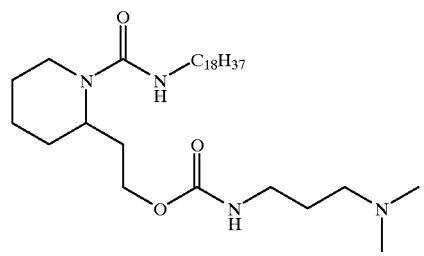

Compound 2: N-[3-(Dimethylamino)propyl]-{2-[1-(N-octadecylcarbamoyl)-2-piperidyl]ethoxy}formamide hydrochloride

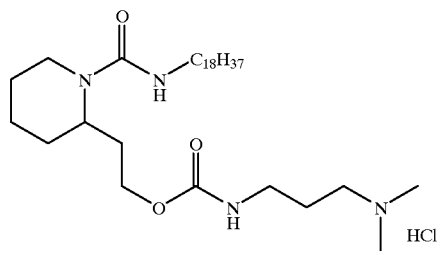

Compound 3: N-(3-Morpholinopropyl)-{2-[1-(N-octadecylcarbamoyl)-2-piperdyl]ethoxy}formamide

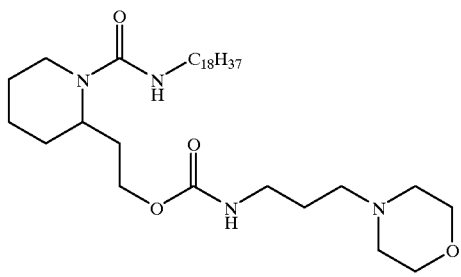

Compound 5: N-[3-(Dimethylamino)propyl]-[2-(1-octadecanoyl-2piperidyl)ethoxy]formamide

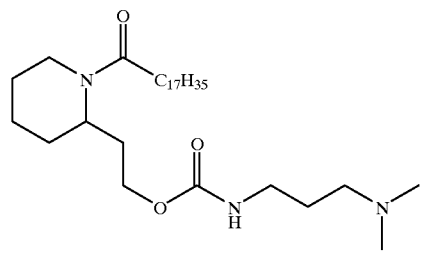

32

Compound 6: N-[3-(Dimethylamino)propyl]-[2-(1-octadecanoyl-2-piperidyl)ethoxy]formamide hydrochloride

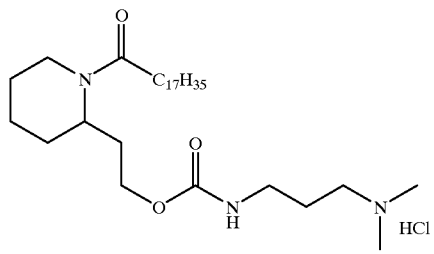

Compound 7: N-[3-(Dimethylamino)propyl]-[2-(1-tetradecanoyl-2-piperidyl)ethoxy]formamide

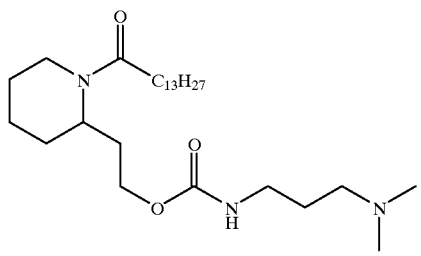

Compound 10: N-(3-Morpholinopropyl)-[2-(1-octadecanoyl-2-piperidyl)ethoxy]formamide

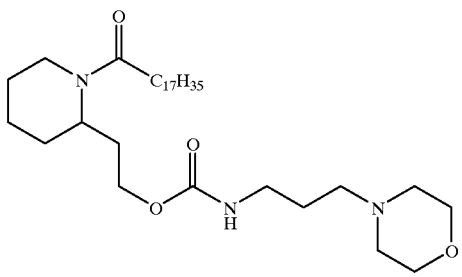

Compound 11: N-(3-Morpholinopropyl)-[2-(1-octadecanoyl-2-piperidyl)ethoxy]formamide hydrochloride

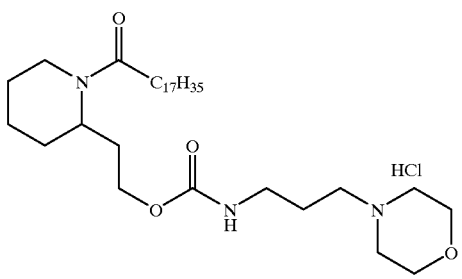

Compound 12: Octadecyl 2-[2-[N-[3-(dimethylamino)propyl]carbamoyloxy]ethyl]piperidinecarboxylate

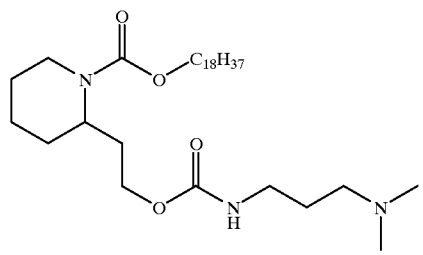

Compound 14: N-[3-(Dimethylamino)propyl]-[2-(1-octadecyl-2-piperidyl)ethoxy]formamide

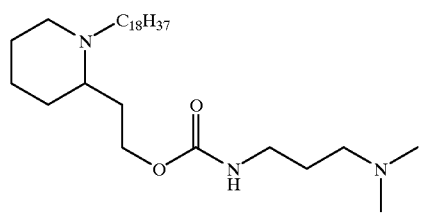

Compound 17: N-[3-(Dimethylamino)propyl]-[2-(1-docosanoyl-2-piperidyl)ethoxy]formamide hydrochloride

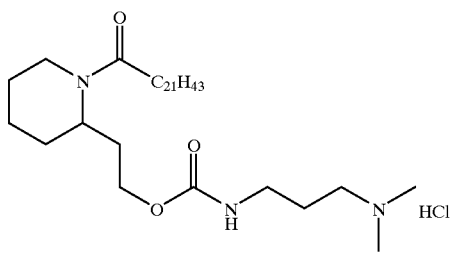

Compound 19: 2-(1-Docosanoyl-2-piperidyl)ethyl N-[2-(dimethylamino)ethyl]carbamate hydrochloride

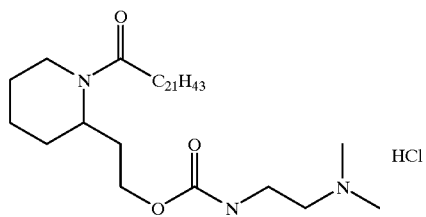

Compound 21: 2-(1-Docosanoyl-2-piperidyl)ethyl N-(3-morpholinopropyl)carbamate hydrochloride

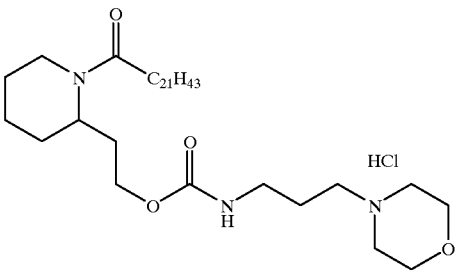

Compound 22: 2-(1-Octadecanoyl-2-piperidyl)ethyl 4-methytetrahydro-1(2H)-pyrazine-carboxylate

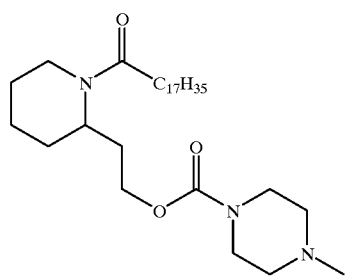

Compound 27: 2-(1-Docosanoyl-2-piperidyl)ethyl 4-methyltetrahydro-1(2H)-pyrazine-carboxylate hydrochloride

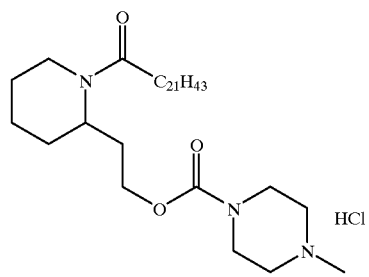

TABLE 1

| Compound | Conc. of Compd. (w/v %) | Days of Application (days) | Hair Regrowth Area Rate (%) |
|---|---|---|---|
| Ethanol (negative contrast) | — | 18 | 0 |
| Compound 1 | 0.1 | 18 | 100 |
| Compound 2 | 0.1 | 18 | 73 |
| Compound 3 | 0.1 | 18 | 100 |
| Compound 5 | 0.1 | 18 | 100 |
| Compound 6 | 0.1 | 17 | 100 |
| Compound 7 | 0.2 | 18 | 97 |
| Compound 10 | 0.1 | 17 | 100 |
| Compound 11 | 0.1 | 18 | 100 |
| Compound 12 | 0.1 | 17 | 100 |
| Compound 14 | 0.1 | 18 | 100 |
| Compound 17 | 0.2 | 18 | 75 |
| Compound 19 | 0.2 | 18 | 36 |
| Compound 21 | 0.1 | 18 | 67 |

TABLE 1-continued

| Compound | Conc. of Compd. (w/v %) | Days of Application (days) | Hair Regrowth Area Rate (%) |
|---|---|---|---|
| Compound 22 | 0.1 | 17 | 100 |
| Compound 27 | 0.1 | 18 | 66 |

As is clear from the TABLE 1, 1,2-di-substituted piperidine derivatives and their pharmacologically acceptable salts in accordance with the present invention show excellent hair regrowth and growth promoting effects.

In the following, examples of compounds and compositions in accordance with the present invention will be explained. However, the present invention should not be restricted thereto.

EXAMPLE 1

N-[3-(Dimethylamino)propyl]-{2-[1-(N-octadecylcarbamoyl)-2-piperidyl]ethoxy}formamide (Compound 1)

(1) [2-(2-Hydroxyethyl)piperidino]-N-octadecylformamide

Triethylamine (6.0 ml) and octadecyl isocyanate (11.500 g) were added to a solution of 2-(2-hydroxyethyl)piperidine (5.009 g) in methylene chloride (50 ml). After being stirred for 4 hours at room temperature, the reaction mixture was diluted with chloroform, washed with 1N hydrochloric acid, saturated sodium hydrogencarbonate aqueous solution and saturated brine successively, dried over sodium sulfate anhydride, and concentrated. The residue was purified by silica gel column chromatography (silica gel 200 g, chloroform:methanol=100:1~80:1), thereby yielding the entitled compound (15.662 g) as white solid.

$^1$H-NMR (CDCl$_3$) δ: 0.88 (3H, t, J=6.8 Hz), 1.2–1.35 (30H, m), 1.40–1.85 (9H, m), 1.94 (1H, m), 2.81 (1H, td, J=12.7, 2.4 Hz), 3.20 (2H, m), 3.40 (1H, t, J=10.7 Hz), 3.59 (2H, m), 3.87 (1H, brs), 4.49 (1H, m), 4.76 (1H, brt).

(2) N-[3-(Dimethylamino)propyl]-{2-[1-(N-octadecylcarbamoyl)-2-piperidyl]ethoxy}formamide Pyridine (4.5 ml) and phenyl chlorocarbonate (5.1 ml) were added to a solution of [2-(2-hydroxyethyl)piperidino]-N-octadecylformamide (15.66 g) in methylene chloride (158 ml) under argon gas atmosphere, while being cooled with ice. After being stirred for 2 hours at room temperature, the reaction mixture was diluted with chloroform, washed with dilute hydrochloric acid, saturated sodium hydrogencarbonate aqueous solution and water successively, dried over sodium sulfate anhydride, and concentrated. N,N-dimethyl-1,3-propanediamine (5.1 ml) was added to the residue under argon gas atmosphere. After being stirred for 2 hours at 70° C., the reaction mixture was purified by silica gel column chromatography (silica gel 350 g, chloroform:methanol=30:1~10:1), thereby yielding the entitled compound (17.89 g) as white solid.

$^1$H-NMR (CDCl$_3$) δ: 0.88 (3H, t, J=6.8 Hz), 1.2–1.35 (30H, m), 1.4–1.79 (1H, m), 2.02 (1H, m), 2.22 (6H, s), 2.34 (2H, t, J=6.6 Hz), 2.79 (1H, t, J=12.7 Hz), 3.19 (2H, m), 3.24 (2H, m), 3.89 (1H, brd), 4.01 (1H, m), 4.12 (2H, m), 4.57 (1H, t, J=5.4 Hz), 5.63 (1H, brt).

EXAMPLE 2

N-[3-(Dimethylamino)propyl]-{2-[1-(N-octadecylcarbamoyl)-2-piperidyl]ethoxy}formamide hydrochloride (Compound 2)

4N Hydrochloric acid/ethyl acetate solution (5.5 ml) was added to a solution of N-[3-(dimethylamino)propyl]-{2-[1-(N-octadecylcarbamoyl)-2-piperidyl]ethoxy}formamide (8.37 g) in ethyl acetate (252 ml) under argon gas atmosphere while being cooled with ice. The solution was stirred for 1.5 hours at room temperature. The deposited crystals were collected by filtration under a vacuum and was recrystallized with ethyl acetate, thereby yielding the entitled compound (8.12 g) as white crystal.

$^1$H-NMR (CDCl$_3$) δ: 0.88 (3H, t, J=6.8 Hz), 1.2–1.35 (30H, m), 1.4–2.1 (12H, m), 2.82 (3H, s), 2.83 (3H, s), 2.88 (1H, m), 3.13 (2H, m), 3.19 (2H, m), 3.35 (2H, m), 3.74 (1H, m), 4.07 (2H, m), 4.25 (1H, m), 4.68 (1H, brs), 6.08 (1H, brs), 12.09 (1H, brs).

EXAMPLE 3

N-(3-Morpholinopropyl)-{2-[1-(N-octadecylcarbamoyl)-2-piperidyl]ethoxy}formamide (Compound 3)

Pyridine (0.33 ml) and phenyl chlorocarbonate (0.38 ml) were added to a solution of [2-(2-hydroxyethyl)piperidino]-N-octadecylformamide (1.130 g), that was prepared in Example 1(1), in methylene chloride (12 ml) under argon gas atmosphere while being cooled with ice. After being stirred for 2.5 hours at room temperature, the reaction solution was diluted with chloroform, washed with dilute hydrochloric acid, saturated sodium hydrogencarbonate aqueous solution and water successively, dried over sodium sulfate anhydride, and concentrated. N-3-(Aminopropyl) morpholine (0.43 ml) was added to the residue under argon gas atmosphere. After being stirred for 3 hours at 70° C., the reaction mixture was purified by silica gel column chromatography (silica gel 50 g, chloroform:methanol=60:1~30:1), thereby yielding the entitled compound (1.417 g) as white solid.

$^1$H-NMR (CDCl$_3$) δ: 0.88 (3H, t, J=6.8 Hz), 1.2–1.35 (30H, m), 1.4–1.8 (11H, m), 2.03 (1H, m), 2.42 (6H, m), 2.82 (1H, t, J=12.2 Hz), 3.19 (2H, m), 3.25 (2H, m), 3.71 (4H, t, J=4.6 Hz), 3.83 (1H, brd), 4.03 (1H, m), 4.09 (1H, m), 4.17 (1H, m), 4.53 (1H, t, J=5.4 Hz), 5.59 (1H, brt).

EXAMPLE 4

N-(3-Morpholinopropyl)-{2-[1-(N-octadecylcarbamoyl)-2-piperidyl]ethoxy}formamide hydrochloride (Compound 4)

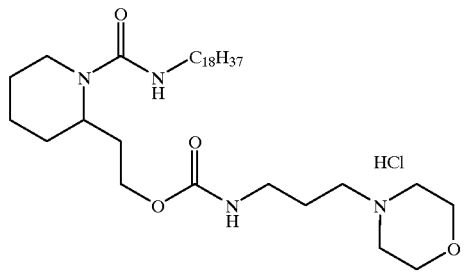

4N Hydrochloric acid/ethyl acetate solution (0.13 ml) was added to a solution of N-(3-morpholinopropyl)-{2-[1-(N-octadecylcarbamoyl)-2-piperidyl]ethoxy}formamide (0.200 g) in ethyl acetate (2 ml). After being stirred for 15 minutes at room temperature, the reaction mixture was concentrated. The residue was recrystallized with ethyl acetate, thereby yielding the entitled compound (0.170 g) as white crystals.

$^1$H-NMR (CDCl$_3$) δ: 0.88 (3H, t, J=6.6 Hz), 1.2–1.35 (30H, m), 1.4–2.2 (12H, m), 2.89 (3H, m), 3.11 (2H, m), 3.19 (2H, m), 3.33 (2H, m), 3.45 (2H, m), 3.70 (1H, m), 3.97 (2H, m), 4.06 (2H, m), 4.29 (3H, m), 6.03 (1H, brs), 12.60 (1H, brs).

EXAMPLE 5

N-[3-(Dimethylamino)propyl]-[2-(1-octadecanoyl-2-piperidyl)ethoxy]formamide (Compound 5)

(1) 1-[2-(2-Hydroxyethyl)piperidino]octadecan-1-one

Triethylamine (1.58 ml) and stearoyl chloride (3.150 g) were added to a solution of 2-(2-hydroxyethyl)piperidine (1.322 g) in methylene chloride (14 ml) under argon gas atmosphere while being cooled with ice. After being stirred for 3 hours, the reaction mixture was diluted with chloroform, washed with 1N hydrochloric acid, saturated sodium hydrogen hydrogencarbonate aqueous solution and saturated brine successively, dried over sodium sulfate anhydride, and concentrated. The residue was purified by silica gel column chromatography (silica gel 82 g, chloroform:methanol=80:1), thereby yielding the entitled compound (3.720 g) as white solid.

$^1$H-NMR (CDCl$_3$) δ: 0.88 (3H, t, J=7.1 Hz), 1.2–1.35 (30H, m), 1.41–1.74 (7H, m), 1.91 (1H, m), 2.36 (2H, t, J=7.8 Hz), 2.94 (1H, td, J=13.2, 2.4 Hz), 3.25 (1H, tt, J=11.7, 2.9 Hz), 3.59 (1H, m), 3.69 (1H, d, J=13.2 Hz), 3.92 (1H, m), 4.86 (1H, m).

(2) N-[3-(Dimethylamino)propyl]-[2-(1-octadecanoyl-2-piperidyl)ethoxy]formamide

Pyridine (0.85 ml) and phenyl chlorocarbonate (0.96 ml) were added to a solution of 1-[2-(2-hydroxyethyl) piperidino]octadecan-1-one (2.758 g) in methylene chloride (28 ml) under argon gas atmosphere, while being cooled with ice. After being stirred for 1.5 hours at room temperature, the reaction mixture was diluted with chloroform, washed with dilute hydrochloric acid, saturated sodium hydrogencarbonate aqueous solution and water successively, dried over sodium sulfate anhydride, and concentrated. N,N-Dimethyl-1,3-propanediamine (0.96 ml) was added to the residue under argon gas atmosphere. After being stirred for 1.5 hours at 70° C., the reaction mixture was purified by silica gel column chromatography (silica gel 100 g, chloroform:methanol=30:1~10:1), thereby yielding the entitled compound (3.063 g) as white solid.

$^1$H-NMR (CDCl$_3$) δ: 0.88 (3H, t, J=6.8 Hz), 1.2–1.45 (28H, m), 1.55–2.1 (12H, m), 2.22 (6H, s), 2.28 (2H, m), 2.34 (2H, m), 2.56 & 3.11 (total 1H, t, J=12.7 Hz), 3.23 (2H, m), 3.65 & 4.56 (total 1H, d, J=12.7 Hz), 4.02 (2H, m), 4.08 & 4.92 (total 1H, m), 5.48 & 5.64 (total 1H, brs).

EXAMPLE 6

N-[3-(Dimethylamino)propyl]-[2-(1-octadecanoyl-2-piperidyl)ethoxy]formamide hydrochloride (Compound 6)

4N Hydrochloric acid/ethyl acetate solution (0.20 ml) was added to a solution of N-[3-(dimethylamino)propyl]-[2-(1-octadecanoyl-2-piperidyl)ethoxy]formamide (0.200 g) in ethyl acetate (2 ml). After being stirred for 15 minutes at room temperature, the reaction mixture was concentrated. The residue was recrystallized with ethyl acetate, thereby yielding the entitled compound (0.183 g) as white crystals.

$^1$H-NMR (CDCl$_3$) δ: 0.88 (3H, t, J=6.8 Hz), 1.2–1.45 (28H, m), 1.5–2.45 (14H, m), 2.58 & 3.08 (total 1H, t, J=13.2 Hz), 2.83 (6H, s), 3.15 (2H, m), 3.35 (2H, m), 3.65 & 4.55 (total 1H, d, J=13.2 Hz), 3.99 (2H, Hz), 4.08 & 4.89 (total 1H, m), 5.71 & 5.88 (total 1H, brs), 12.11 (1H, brs).

EXAMPLE 7

N-[3-(Dimethylamino)propyl]-[2-(1-tetradecanoyl-2-piperidyl)ethoxy]formamide (Compound 7)

(1) 1-[2-(2-Hydroxyethyl)piperidino]tetradecan-1-one

Triethylamine (0.79 ml) and myristoyl chloride (1.270 g) were added to a solution of 2-(2-hydroxyethyl)piperidine (0.660 g) in methylene chloride (7 ml) under argon gas atmosphere while being cooled with ice. After being stirred for 2 hours, the reaction mixture was diluted with chloroform, washed with 1N hydrochloric acid, saturated sodium hydrogencarbonate aqueous solution and saturated brine successively, dried over sodium sulfate anhydride, and concentrated. The residue was purified by silica gel column chromatography (silica gel 50 g, chloroform:methanol= 60:1), thereby yielding the entitled compound (1.664 g) as white solid.

$^1$H-NMR (CDCl$_3$) δ: 0.88 (3H, t, J=6.8 Hz), 1.2–1.4 (20H, m), 1.4–1.75 (9H, m), 1.91 (1H, t, J=13.4 Hz), 2.36 (2H, t, J=7.6 Hz), 2.93 (1H, td, J=13.2, 2.9 Hz), 3.25 (1H, m), 3.58 (1H, m), 3.69 (1H, d, J=13.2 Hz), 3.92 (1H, d, J=10.3 Hz), 4.86 (1H, m).

(2) N-[3-(Dimethylamino)propyl]-[2-(1-tetradecanoyl-2-piperidyl)ethoxy]formamide Pyridine (0.52 ml) and phenyl chlorocarbonate (0.59 ml) were added to a solution of 1-[2-(2-hydroxyethyl) piperidino]tetradecan-1-one (1.457 g) in methylene chloride (15 ml) under argon gas atmosphere, while being cooled with ice. After being stirred for 3.5 hours at room temperature, the reaction mixture was diluted with chloroform, washed with dilute hydrochloric acid, saturated hydrogencarbonate aqueous solution and water successively, dried over sodium sulfate anhydride, and concentrated. N,N-Dimethyl-1,3-propanediamine (0.59 ml) was added to the residue under argon gas atmosphere. After being stirred for 2 hours at 70° C., the reaction mixture was purified by silica gel column chromatography (silica gel 55 g, chloroform:methanol=30:1~10:1), thereby yielding the entitled compound (1.737 g) as colorless syrup.

$^1$H-NMR (CDCl$_3$) δ: 0.88 (3H, t, J=6.8 Hz), 1.2–1.45 (20H, m), 1.55–2.1 (12H, m), 2.22 (6H, s), 2.28 (2H, m), 2.34 (2H, m), 2.56 & 3.11 (total 1H, t, J=12.5 Hz), 3.23 (2H, m), 3.65 & 4.56 (total 1H, d, J=11.7 Hz), 4.02 (2H, m), 4.08 & 4.92 (total 1H, brt), 5.49 & 5.64 (total 1H, brt).

EXAMPLE 8

[2-(1-Decanoyl-2-piperidyl)ethoxy]-N-[3-(dimethylamino)propyl]formamide (Compound 8)

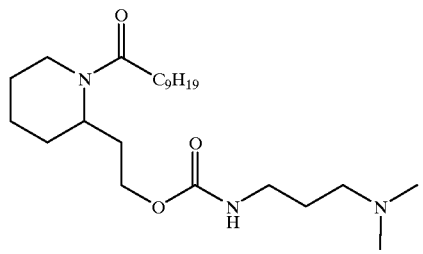

(1) 1-[2-(2-Hydroxyethyl)piperidino]decan-1-one

Triethylamine (1.04 ml) and decanoyl chloride (1.320 g) were added to a solution of 2-(2-hydroxyethyl)piperidine (0.874 g) in methylene chloride (9 ml) under argon gas atmosphere, while being cooled with ice. After being stirred for 2.5 hours, the reaction mixture was diluted with chloroform, washed with 1N hydrochloric acid, saturated sodium hydrogencarbonate aqueous solution and saturated brine successively, dried over sodium sulfate anhydride, and concentrated. The residue was purified by silica gel column chromatography (silica gel 50 g, chloroform:methanol= 80:1), thereby yielding the entitled compound (1.775 g) as colorless syrup.

$^1$H-NMR (CDCl$_3$) δ: 0.88 (3H, t, J=7.1 Hz), 1.2–1.35 (12H, m), 1.41–1.76 (9H, m), 1.91 (1H, tt, J=12.2, 2.4 Hz), 2.36 (2H, t, J=7.8 Hz), 2.94 (1H, td, J=13.7, 2.9 Hz), 3.25 (1H, m), 3.59 (1H, m), 3.69 (1H, d, J=12.7 Hz), 3.94 (1H, dd, J=10.7, 3.9 Hz), 4.86 (1H, m).

(2) [2-(1-Decanoyl-2-piperidyl)ethoxy]-N-[3-(dimethylamino)propyl]formamide

Pyridine (0.72 ml) and phenyl chlorocarbonate (0.82 ml) were added to a solution of 1-[2-(2-hydroxyethyl) piperidino]decan-1-one (1.675 g) in methylene chloride (17 ml) under argon gas atmosphere, while being cooled with ice. After being stirred for 1.5 hours at room temperature, the reaction mixture was diluted with chloroform, washed with dilute hydrochloric acid, saturated sodium hydrogencarbonate aqueous solution and saturated brine successively, dried over sodium sulfate anhydride, and concentrated. N,N-Dimethyl-1,3-propanediamine (0.82 ml) was added to the residue under argon gas atmosphere. After being stirred for 2 hours at 70° C., the reaction mixture was purified by silica gel column chromatography (silica gel 65 g, chloroform:methanol=30:1~10:1), thereby yielding the entitled compound (2.102 g) as colorless syrup.

$^1$H-NMR (CDCl$_3$) δ: 0.88 (3H, t, J=6.8 Hz), 1.2–1.45 (12H, m), 1.55–2.1 (12H, m), 2.22 (6H, s), 2.28 (2H, m), 2.34 (2H, m), 2.56 & 3.11 (total 1H, t, J=12.2 Hz), 3.23 (2H, m), 3.65 & 4.57 (total 1H, d, J=12.2 Hz), 4.02 (2H, m), 4.08 & 4.92 (total 1H, brt), 5.50 & 5.66 (total 1H, brt).

EXAMPLE 9

N-[3-(Dimethylamino)propyl]-[2-(1-heptanoyl-2-piperidyl)ethoxy]formamide (Compound 9)

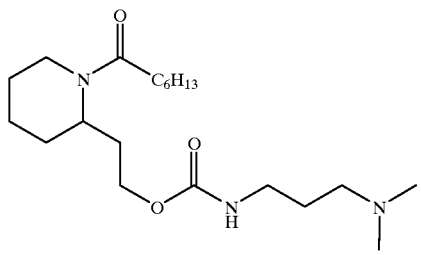

(1) 1-[2-(2-Hydroxyethyl)piperidino]heptan-1-one

Triethylamine (1.20 ml) and enanthyl chloride (1.170 g) were added to a solution of 2-(2-hydroxyethyl)piperidine (1.008 g) in methylene chloride (10 ml) under argon gas atmosphere, while being cooled with ice. After being stirred for 3 hours, the reaction mixture was diluted with chloroform, washed with 1N hydrochloric acid, saturated sodium hydrogencarbonate aqueous solution and saturated brine successively, dried over sodium sulfate anhydride, and concentrated. The residue was purified by silica gel column chromatography (silica gel 50 g, chloroform:methanol= 80:1), thereby yielding the entitled compound (1.731 g) as colorless syrup.

$^1$H-NMR (CDCl$_3$) δ: 0.89 (3H, t, J=6.8 Hz), 1.25–1.77 (15H, m), 1.92 (1H, tdd, J=12.7, 4.4, 2.5 Hz), 2.36 (2H, t, J=7.8 Hz), 2.94 (1H, td, J=13.2, 2.5 Hz), 3.25 (1H, tdd, J=11.7, 3.4, 2.5 Hz), 3.59 (1H, m), 3.69 (1H, d, J=13.7 Hz), 3.93 (1H, dd, J=10.7, 3.9 Hz), 4.86 (1H, m).

(2) N-[3-(Dimethylamino)propyl]-[2-(1-heptanoyl-2-piperidyl)ethoxy]formamide

Pyridine (0.81 ml) and phenyl chlorocarbonate (0.92 ml) were added to a solution of 1-[2-(2-hydroxyethyl) piperidino]heptan-1-one (1.598 g) in methylene chloride (16 ml) under argon gas atmosphere, while being cooled with ice. After being stirred for 1.5 hours at room temperature, the reaction mixture was diluted with chloroform, washed with dilute hydrochloric acid, saturated sodium hydrogencarbonate aqueous solution and saturated brine successively, dried over sodium sulfate anhydride, and concentrated. N,N-Dimethyl-1,3-propanediamine (0.92 ml) was added to the residue under argon gas atmosphere. After being stirred for 1.5 hours at 70° C., the reaction mixture was purified by silica gel column chromatography (silica gel 75 g, chloroform:methanol=30:1~10:1), thereby yielding the entitled compound (1.957 g) as colorless syrup.

$^1$H-NMR (CDCl$_3$) δ: 0.88 (3H, t, J=6.8 Hz), 1.25–1.45 (6H, m), 1.55–2.1 (12H, m), 2.22 (6H, s), 2.28 (2H, m), 2.33 (2H, m), 2.56 & 3.11 (total 1H, t, J=13.2 Hz), 3.23 (2H, m), 3.65 & 4.57 (total 1H, d, J=13.2 Hz), 4.02 (2H, m), 4.08 & 4.92 (total 1H, brt), 5.50 & 5.65 (total 1H, brt).

EXAMPLE 10

N-(3-Morpholinopropyl)-[2-(1-octadecanoyl-2-piperidyl)ethoxy]formamide (Compound 10)

Pyridine (0.39 ml) and phenyl chlorocarbonate (0.42 ml) were added to a solution of 1-[2-(2-hydroxyethyl) piperidino]octadecan-1-one (1.160 g), that was prepared in Example 5 (1), in methylene chloride (12 ml) under argon gas atmosphere, while being cooled with ice. After being stirred for 2.5 hours at room temperature, the reaction mixture was diluted with chloroform, washed with dilute hydrochloric acid, saturated sodium hydrogencarbonate aqueous solution and water successively, dried over sodium sulfate anhydride, and concentrated. N-(3-Aminopropyl) morpholine (0.48 ml) was added to the residue under argon gas atmosphere. After being stirred for 3.5 hours at 70° C., the reaction mixture was purified by silica gel column chromatography (silica gel 50 g, chloroform:methanol= 30:1), thereby yielding the entitled compound (1.506 g) as white solid.

$^1$H-NMR (CDCl$_3$) δ: 0.88 (3H, t, J=6.8 Hz), 1.2–1.45 (28H, m), 1.55–2.1 (12H, m), 2.29 (2H, m), 2.43 (6H, m), 2.56 & 3.10 (total 1H, t, J=12.2 Hz), 3.24 (2H, m), 3.66 & 4.57 (total 1H, d, J=10.3 Hz), 3.71 (4H, m), 3.97 & 4.92 (total 1H, brt), 4.05 (2H, m), 5.57 & 6.03 (total 1H, brt).

EXAMPLE 11

N-(3-Morpholinopropyl)-[2-(1-octadecanoyl-2-piperidyl)ethoxy]formamide hydrochloride (Compound 11)

4N Hydrochloric acid/ethyl acetate solution (0.26 ml) was added to a solution of N-(3-morpholinopropyl)-[2-(1-octadecanoyl-2-piperidyl)ethoxy]formamide (0.500 g) in ethyl acetate (5 ml). After being stirred for 15 minutes at room temperature, the reaction mixture was concentrated, thereby yielding the entitled compound (0.532 g) as white solid.

$^1$H-NMR (CDCl$_3$) δ: 0.88 (3H, t, J=6.6 Hz), 1.2–1.45 (28H, m), 1.55–2.5 (14H, m), 2.59 & 3.07 (total 1H, t, J=12.7 Hz), 2.9–3.55 (8H, m), 3.66 & 4.54 (total 1H, d, J=13.2 Hz), 3.99 (4H, m), 4.08 & 4.88 (total 1H, brt), 4.27 (2H, m), 5.90 & 6.01 (total 1H, brt), 12.40 (1H, brs).

EXAMPLE 12

Octadecyl 2-[2-[N-[3-(dimethylamino)propyl] carbamoyloxy]ethyl]piperidinecarboxylate (Compound 12)

(1) Octadecyl 2-(2-hydroxyethyl)piperidinecarboxylate

Pyridine (0.77 ml) and phenyl chlorocarbonate (0.88 ml) were added to a suspension of stearyl alcohol (1.708 g) in methylene chloride (18 ml) under argon gas atmosphere, while being cooled with ice. After being stirred for 2 hours at room temperature, the reaction mixture was diluted with chloroform, washed with dilute hydrochloric acid, saturated sodium hydrogencarbonate aqueous solution and water successively, dried over sodium sulfate anhydride, and concentrated. 2-(2-Hydroxyethyl)piperidine (0.911 g) was added to the residue under argon gas atmosphere. After being stirred for 19 hours at 70° C., the reaction mixture was purified by silica gel column chromatography (silica gel 100 g, chloroform:methanol=100:1; and silica gel 75 g, hexane-:ethyl acetate=10:1~5:1, successively), thereby yielding the entitled compound (1.117 g) as white solid.

$^1$H-NMR (CDCl$_3$) δ: 0.88 (3H, t, J=6.8 Hz), 1.2–1.8 (39H, m), 1.96 (1H, t, J=12.7 Hz), 2.73 (1H, td, J=13.2, 2.4 Hz), 3.40 (1H, m), 3.60 (2H, m), 4.00 (1H, m), 4.08 (2H, m), 4.46 (1H, m).

(2) Octadecyl 2-{2-[N-[3-(dimethylamino)propyl] carbamoyloxy]ethyl}piperidinecarboxylate Pyridine (0.31 ml) and phenyl chlorocarbonate (0.35 ml) were added to a solution of octadecyl 2-(2-hydroxyethyl) piperidinecarboxylate (1.09 g) in methylene chloride (10 ml) under argon gas atmosphere, while being cooled with ice. After being stirred for 1.5 hours at room temperature, the reaction mixture was diluted with chloroform, washed with dilute hydrochloric acid, saturated sodium hydrogencarbonate aqueous solution and water successively, dried over sodium sulfate anhydride, and concentrated. N,N-Dimethyl-1,3-propanediamine (0.35 ml) was added to the residue under argon gas atmosphere. After being stirred for 5 hours at 70° C., the reaction mixture was purified by silica gel column chromatography (silica gel 30 g, chloroform:methanol=20:1), thereby yielding the entitled compound (1.58 g) as colorless oil.

$^1$H-NMR (CDCl$_3$) δ: 0.88 (3H, t, J=6.8 Hz), 1.2–1.45 (30H, m), 1.55–1.8 (11H, m), 2.05 (1H, m), 2.21 (6H, s), 2.32 (2H, t, J=6.8 Hz), 2.83 (1H, t, J=12.7 Hz), 3.23 (2H, q, J=6.4 Hz), 4.02 (1H, m), 4.04 (4H, t, J=6.8 Hz), 4.39 (1H, m), 5.45 (1H, brt).

EXAMPLE 13

Octadecyl 2-{2-[N-[3-(dimethylamino)propyl] carbamoyloxy]ethyl}piperidinecarboxylate hydrochloride (Compound 13)

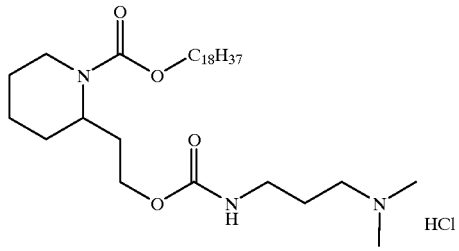

4N Hydrochloric acid/ethyl acetate solution (1.28 ml) was added to a solution of octadecyl 2-{2-[N-[3-(dimethylamino)propyl]carbamoyloxy] ethyl}piperidinecarboxylate (1.55 g) in ethyl acetate (5 ml). After being stirred for 15 minutes at room temperature, the reaction mixture was concentrated, thereby yielding the entitled compound (1.38 g) as white wax.

$^1$H-NMR (CDCl$_3$) δ: 0.88 (3H, t, J=6.6 Hz), 1.2–1.45 (30H, m), 1.5–1.8 (9H, m), 2.09 (3H, m), 2.81 (3H, s), 2.82 (3H, s), 2.83 (1H, t, J=12.7 Hz), 3.10 (2H, m), 3.35 (2H, m), 4.02 (5H, m), 4.39 (1H, m), 5.63 (1H, brt).

EXAMPLE 14

N-[3-(Dimethylamino)propyl]-[2-(1-octadecyl-2-piperidyl)ethoxy]formamide (Compound 14)

(1) 2-(1-Octadecyl-2-piperidyl)ethan-1-ol

Potassium carbonate (2.312 g) and 1-bromooctadecane (2.80 ml) were added to a solution of 2-(2-hydroxyethyl) piperidine (1.057 g) in acetone. The solution was stirred for 18 hours at 40° C. and was further stirred for 23 hours at 60° C. After the insoluble matter was filtrated out under a vacuum, the filtrate was concentrated. The residue was diluted with chloroform, washed with saturated sodium hydrogencarbonate aqueous solution and saturated brine successively, dried over sodium sulfate anhydride, and concentrated. The residue was purified by silica gel column chromatography (silica gel 60 g, chloroform:methanol= 30:1~10:1), thereby yielding the entitled compound (1.935 g) as white solid.

$^1$H-NMR (CDCl$_3$) δ: 0.88 (3H, t, J=6.8 Hz), 1.2–1.35 (30H, m), 1.4–1.75 (9H, m), 1.86 (1H, m), 2.33 (1H, m), 2.51 (1H, m), 2.73 (1H, m), 2.82 (1H, m), 3.08 (1H, m), 3.76 (1H, m), 3.91 (1H, m).

(2) N-[3-(Dimethylamino)propyl]-[2-(1-octadecyl-2-piperidyl)ethoxy]formamide

Pyridine (0.79 ml) and phenyl chlorocarbonate (0.92 ml) were added to a solution of 2-(1-octadecyl-2-piperidyl) ethan-1-ol (1.860 g) in methylene chloride (20 ml) under argon gas atmosphere, while being cooled with ice. After being stirred for 2 hours at room temperature, the reaction mixture was diluted with chloroform, washed with dilute hydrochloric acid, saturated sodium hydrogencarbonate aqueous solution and water successively, dried over sodium sulfate anhydride, and concentrated. N,N-Dimethyl-1,3-propanediamine (0.67 ml) was added to the residue under argon gas atmosphere. After being stirred for 5 hours at 70° C., the reaction mixture was purified by silica gel column chromatography (silica gel 85 g, chloroform:methanol= 20:1~10:1), thereby yielding the entitled compound (0.843 g) as colorless syrup.

$^1$H-NMR (CDCl$_3$) δ: 0.88 (3H, t, J=6.8 Hz), 1.2–1.35 (30H, m), 1.4–2.0 (12H, m), 2.2–2.5 (3H, m), 2.21 (6H, s), 2.33 (2H, t, J=6.6 Hz), 2.62 (1H, m), 2.83 (1H, m), 3.24 (2H, m), 4.10 (2H, m), 5.51 (1H, brt).

EXAMPLE 15

N-[3-(Dimethylamino)propyl]-[2-(1-octadecyl-2-piperidyl)ethoxy]formamide dihydrochloride (Compound 15)

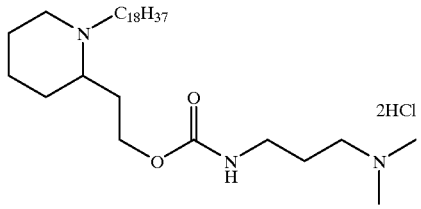

4N Hydrochloric acid/ethyl acetate solution (0.21 ml) was added to a solution of N-[3-(dimethylamino)propyl]-[2-(1-octadecyl-2-piperidyl)ethoxy]formamide (0.200 g) in ethyl acetate (4 ml) under argon gas atmosphere, while being cooled with ice. After being stirred for 15 minutes, the reaction mixture was concentrated. The residue was recrystallized with the mixed solution of ethyl acetate-hexane, thereby yielding the entitled compound (0.199 g) as white crystals.

$^1$H-NMR (CDCl$_3$) δ: 0.88 (3H, t, J=6.8 Hz), 1.2–2.4 (42H, m), 2.8–3.6 (9H, m), 2.85 (6H, s), 4.16 (2H, m).

EXAMPLE 16

N-[3-(Dimethylamino)propyl]-[2-(1-docosanoyl-2-piperidyl)ethoxy]formamide (Compound 16)

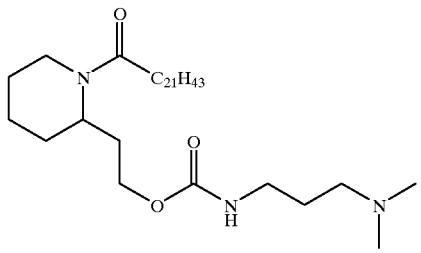

(1) 1-[2-(2-Hydroxyethyl)piperidino]docosan-1-one

Triethylamine (1.74 ml) was added to a suspension of behenic acid (3.80 g) in chloroform (40 ml) under argon gas atmosphere. Then, ethyl chlorocarbonate (1.18 ml) was dropwise added to the mixture while being cooled with ice. After being stirred for 2.5 hours at 0° C., a solution of 2-(2-hydroxyethyl)piperidine (1.46 g) in chloroform (7 ml) was dropwise added to the mixture. After being stirred for 2.5 hours at 0° C., the reaction mixture was diluted with chloroform, washed with 1N hydrochloric acid, saturated sodium hydrogencarbonate aqueous solution and saturated brine successively, dried over sodium sulfate anhydride, and concentrated. The residue was purified by silica gel column chromatography (silica gel 100 g, chloroform:ethyl acetate= 10:1), thereby yielding the entitled compound (3.73 g) as white solid.

$^1$H-NMR (CDCl$_3$) δ: 0.88 (3H, t, J=6.8 Hz), 1.2–1.4 (36H, m), 1.4–1.8 (9H, m), 1.91 (1H, t, J=13.2 Hz), 2.36 (2H, t, J=7.6 Hz), 2.93 (1H, td, J=13.2, 2.4 Hz), 3.24 (1H, td, J=11.5, 3.4 Hz), 3.59 (1H, m), 3.69 (1H, d, J=13.2 Hz), 3.94 (1H, dd, J=11.5, 3.4 Hz), 4.86 (1H, m).

(2) N-[3-(Dimethylamino)propyl]-[2-(1-docosanoyl-2-piperidyl)ethoxy]formamide

Pyridine (0.32 ml) and phenyl chlorocarbonate (0.36 ml) were added to a solution of 1-[2-(2-hydroxyethyl)piperidino]docosan-1-one (1.18 g) in methylene chloride (12 ml), while being cooled with ice. After being stirred for 3.5 hours at room temperature, the reaction mixture was diluted with chloroform, washed with 1N hydrochloric acid, saturated sodium hydrogencarbonate aqueous solution and saturated brine successively, dried over sodium sulfate anhydride, and concentrated. N,N-Dimethyl-1,3-propanediamine (0.36 ml) was added to the residue. After being stirred for 2 hours at 70° C., the reaction mixture was purified by silica gel column chromatography (silica gel 50 g, chloroform:methanol=30:1~10:1), thereby yielding the entitled compound (1.25 g) as white solid.

$^1$H-NMR (CDCl$_3$) δ: 0.88 (3H, t, J=6.8 Hz), 1.1–1.5 (36H, m), 1.55–2.1 (12H, m), 2.22 (6H, s), 2.25–2.4 (4H, m), 2.56 & 3.11 (total 1H, t, J=12.6 Hz), 3.23 (2H, m), 3.65 & 4.56 (total 1H, d, J=12.6 Hz), 4.02 (2H, m), 4.08 & 4.92 (total 1H, m), 5.49 & 5.66 (total 1H, brs).

EXAMPLE 17

N-[3-(Dimethylamino)propyl]-[2-(1-docosanoyl-2-piperidyl)ethoxy]formamide hydrochloride (Compound 17)

4N Hydrochloric acid/ethyl acetate solution (0.58 ml) was added to a solution of N-[3-(dimethylamino)propyl]-[2-(1-docosanoyl-2-piperidyl)ethoxy]formamide (1.04 g) in ethyl acetate (11 ml) at room temperature. After being stirred for 20 minutes, the reaction mixture was concentrated. The residue was recrystallized with ethyl acetate, thereby yielding the entitled compound (1.12 g) as white crystals.

$^1$H-NMR (CDCl$_3$) δ: 0.88 (3H, t, J=6.8 Hz), 1.1–1.5 (36H, m), 1.5–2.5 (14H, m), 2.58 (0.4H, t, 11.8 Hz), 2.82 (6H, s), 3.07 (2.6H, m), 3.35 (2H, m), 3.65 & 4.55 (total 1H, d, J=11.8 Hz), 4.00 (2H, m), 4.08 & 4.90 (total 1H, m), 5.66 & 5.84 (total, 1H, brs), 12.19 (1H, brs).

EXAMPLE 18

2-(1-Docosanoyl-2-piperidyl)ethyl N-[2-(dimethylamino)ethyl]carbamate (Compound 18)

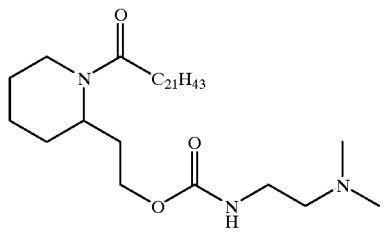

Pyridine (0.68 ml) and phenyl chlorocarbonate (0.78 ml) were added to a solution of 1-[2-(2-hydroxyethyl)piperidino]docosan-1-one (2.500 g), that was prepared in Example 16 (1), in methylene chloride (25 ml), while being cooled with ice. After being stirred for 2.5 hours at room temperature, the reaction mixture was diluted with chloroform, washed with 1N hydrochloric acid, saturated sodium hydrogencarbonate aqueous solution and saturated brine successively, dried over sodium sulfate anhydride, and concentrated. N,N-Dimethylethylenediamine (0.67 ml) was added to the residue. After being stirred for 2 hours at 70°

C., the reaction mixture was purified by silica gel column chromatography (silica gel 100 g, chloroform:methanol=30:1~10:1), thereby yielding the entitled compound (2.629 g) as white solid.

$^1$H-NMR (CDCl$_3$) δ: 0.88 (3H, t, J=6.8 Hz), 1.2–1.45 (36H, m), 1.62 (6H, m), 1.69–1.87 (3H, m), 2.02 (1H, m), 2.22 (6H, s), 2.29 (2H, m), 2.39 (2H, m), 2.55 & 3.10 (total 1H, each t, J=13.2 Hz), 3.24 (2H, m), 3.65 & 4.57 (total 1H, each d, J=13.2 Hz), 3.95–4.15 (2H, m), 4.09 & 4.93 (total 1H, each brt), 5.21 (1H, brt).

EXAMPLE 19

2-(1-Docosanoyl-2-piperidyl)ethyl N-[2-(dimethylamino)ethyl]carbamate hydrochloride (Compound 19)

4N Hydrochloric acid/ethyl acetate solution (1.34 ml) was added to a solution of 2-(1-docosanoyl-2-piperidyl)ethyl N-[2-(dimethylamino)ethyl]carbamate (2.500 g) in ethyl acetate (25 ml) and the mixture was stirred for 0.5 hour. After the reaction mixture was concentrated, the residue was recrystallized with a mixed solution of ethyl acetate-ethanol, thereby yielding the entitled compound (2.287 g) as white solid.

$^1$H-NMR (CDCl$_3$) δ: 0.88 (3H, t, J=6.8 Hz), 1.2–1.45 (36H, m), 1.62 (6H, m), 1.79 (2H, m), 2.01 (1H, m), 2.20 & 2.41 (total 1H, each m), 2.29 (2H, m), 2.60 & 3.07 (total 1H, each t, J=13.2 Hz), 2.89 (6H, s), 3.21 & 3.29 (total 2H, each m), 3.64 (2H, m), 3.65 & 4.55 (total 1H, each d, J=13.2 Hz), 3.96 & 4.16 (total 2H, each m), 4.10 & 4.90 (total 1H, each brt), 6.61 & 6.83 (total 1H, each brt), 12.04 & 12.23 (total 1H, each brs).

EXAMPLE 20

2-(1-Docosanoyl-2-piperidyl)ethyl N-(3-morpholinopropyl)carbamate (Compound 20)

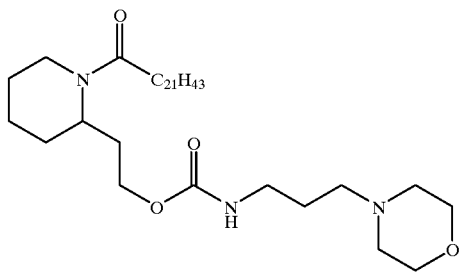

Pyridine (0.65 ml) and phenyl chlorocarbonate (0.74 ml) were added to a solution of 1-[2-(2-hydroxyethyl) piperidino]docosan-1-one (2.392 g), that was prepared in Example 16 (1), in methylene chloride (24 ml), while being cooled with ice. After being stirred for 3.5 hours at room temperature, the reaction mixture was diluted with chloroform, washed with 1N hydrochloric acid, saturated sodium hydrogencarbonate aqueous solution and saturated brine successively, dried over sodium sulfate anhydride, and concentrated. N-(3-Aminopropyl)morpholine (0.86 ml) was added to the residue. After being stirred for 2 hours at 70° C., the reaction mixture was purified by silica gel column chromatography (silica gel 100 g, chloroform: methanol=30:1–10:1), thereby yielding the entitled compound (3.072 g) as white solid.

$^1$H—NMR (CDCl$_3$) δ: 0.88 (3H, t, J=6.8 Hz), 1.2–1.45 (36H, m), 1.62 & 1.67 (total 10H, each m), 1.78, 1.84, 1.97 & 2.07 (total 2H, each m), 2.29 (2H, m), 2.43 (6H, m), 2.56 & 3.10 (total 1H, each t, J=13.2 Hz), 3.24 (2H, m), 3.66 & 4.57 (total 1H, each d, J=13.2 Hz), 3.71 (4H, m), 3.95–4.15 (2H, m), 4.03 & 4.92 (total 1H, each brt), 5.56 & 5.60 (total 1H, each brt).

EXAMPLE 21

2-(1-Docosanoyl-2-piperidyl)ethyl N-(3-morpholinopropyl)carbamate hydrochloride (Compound 21)

4N hydrochloric acid/ethyl acetate solution (1.35 ml) was added to a solution of 2-(1-docosanoyl-2-piperidyl)ethyl N-(3-morpholinopropyl)carbamate (2.800 g) in ethyl acetate (28 ml), while being cooled with ice. After being stirred for 0.5 hour, the reaction mixture was concentrated. The residue was recrystallized with ethyl acetate, thereby yielding the entitled compound (2.546 g) as white solid.

$^1$H-NMR (CDCl$_3$) δ: 0.88 (3H, t, J=6.8 Hz), 1.2–1.45 (36H, m), 1.61 (6H, m), 1.77, 1.96, 2.06, 2.28 & 2.37 (total 8H, each m), 2.58 & 3.07 (total 1H, each t, J=13.2 Hz), 3.06 & 3.34 (total 8H, each m), 3.66 & 4.55 (total 1H, each d, J=13.2 Hz), 3.9–4.3 & 4.89 (total 7H, each m), 5.68 & 5.83 (total 1H, each brt).

EXAMPLE 22

2-(1-Octadecanoyl-2-piperidyl)ethyl 4-methyltetrahydro-1(2H)-pyrazinecarboxylate (Compound 22)

Pyridine (0.37 ml) and phenyl chlorocarbonate (0.42 ml) were added to a solution of 1-[2-(2-hydroxyethyl) piperidino]octadecan-1-one (1.210 g), that was prepared in Example 5 (1), in methylene chloride (13 ml), while being cooled with ice. After being stirred for 3.5 hours at room temperature, the reaction mixture was diluted with chloroform, washed with 1N hydrochloric acid, saturated sodium hydrogencarbonate aqueous solution and saturated brine successively, dried over sodium sulfate anhydride, and concentrated. N-Methylpiperazine (0.38 ml) was added to the residue. After being stirred for 3 hours at 70° C., the reaction mixture was purified by silica gel column chromatography (silica gel 50 g, ethyl acetate (230 ml), and chloroform: methanol=60: 1, successively), thereby yielding the entitled compound (1.440 g) as white solid.

$^1$H-NMR (CDCl$_3$) δ: 0.88 (3H, t, J=6.8 Hz), 1.2–1.45 (28H, m), 1.62 (8H, m), 1.80 & 1.93 (total 1H, each m), 2.04 (1H, m), 2.2–2.4 (2H, m), 2.29 (3H, s), 2.35 (4H, m), 2.56 & 3.11 (total 1H, each t, J=12.5 Hz), 3.49 (4H, m), 3.66 & 4.58 (total 1H, each d, J=12.5 Hz), 4.02 & 4.14 (total 2H, each m), 4.08 & 4.94 (total 1H, each brt).

EXAMPLE 23

2-(1-Octadecanoyl-2-piperidyl)ethyl 4-methyltetrahydro-1(2H)-pyrazinecarboxylate hydrochloride (Compound 23)

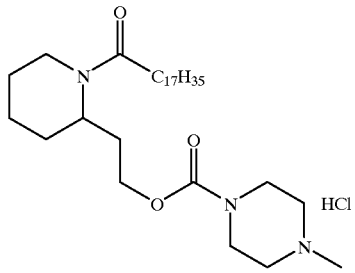

4N Hydrochloric acid/ethyl acetate solution (0.11 ml) was added to a solution of 2-(1-octadecanoyl-2-piperidyl)ethyl 4-methyltetrahydro-1(2H)-pyrazinecarboxylate (0.200 g) in ethyl acetate (2 ml). After being stirred for 15 minutes at room temperature, the reaction mixture was concentrated, thereby yielding the entitled compound (0.219 g) as white solid.

$^1$H-NMR (CDCl$_3$) δ: 0.88 (3H, t, J=6.6 Hz), 1.2–1.45 (28H, m), 1.5–1.9, 2.03 & 2.37 (total 10H, each m), 2.27 (2H, t, J=7.6 Hz), 2.82 (3H, s), 2.99, 3.11, 3.29, 3.65, 3.88, 4.21 & 4.87 (total 13H, each m), 12.74 (1H, brs).

EXAMPLE 24

2-(1-Octadecanoyl-2-piperidyl)ethyl 4-benzyltetrahydro-1(2H)-pyrazinecarboxylate (Compound 24)

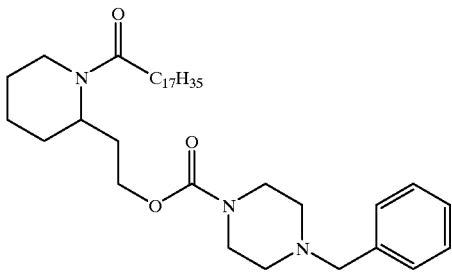

Pyridine (0.54 ml) and phenyl chlorocarbonate (0.62 ml) were added to a solution of 1-[2-(2-hydroxyethyl)piperidino]octadecan-1-one (1.732 g), that was prepared in Example 5 (1), in methylene chloride (18 ml), while being cooled with ice. After being stirred for 2 hours at room temperature, the reaction mixture was diluted with chloroform, washed with 1N hydrochloric acid, saturated sodium hydrogencarbonate aqueous solution and saturated brine successively, dried over sodium sulfate anhydride, and concentrated. 1-Benzylpiperazine (0.84 ml) was added to the residue. After being stirred for 2 hours at 70° C., the reaction mixture was purified by silica gel column chromatography (silica gel 100 g, chloroform: ethyl acetate=5:1–2:1), thereby yielding the entitled compound (2.465 g) as white solid.

$^1$H-NMR (CDCl$_3$) δ:0.88 (3H, t, J=6.8 Hz), 1.2–1.45 (28H, m), 1.61 (8H, m), 1.80, 1.92, 2.03 & 2.25 (total 2H, each m), 2.29 (2H, t, J=6.8 Hz), 2.40 (4H, m), 2.55 & 3.10 (total 1H, each t, J=13.2 Hz), 3.47 (4H, m), 3.51 (2H, s), 3.65 & 4.57 total 1H, each d, J=13.2 Hz), 4.02 & 4.13 (total 2H, each m), 4.07 & 4.92 (total 1 H, each brt), 7.24–7.34 (5H, m).

EXAMPLE 25

2-(1-Octadecanoyl-2-piperidyl)ethyl 4-benzyltetrahydro-1(2H)-pyrazinecarboxylate hydrochloride (Compound 25)

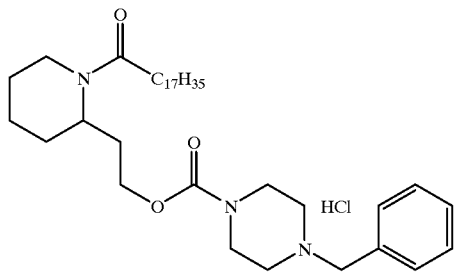

4N Hydrochloric acid/ethyl acetate solution (1.24 ml) was added to a solution of 2-(1-octadecanoyl-2-piperidyl)ethyl 4-benzyltetrahydro-1(2H)-pyrazinecarboxylate (2.465 g) in ethyl acetate (25 ml). After being stirred for 30 minutes, the reaction mixture was concentrated. The residue was recrystallized with ethyl acetate, thereby yielding the entitled compound (2.041 g) as white solid.

$^1$H-NMR (CDCl$_3$) δ: 0.88 (3H, t, J=6.8 Hz), 1.2–1.45 (28H, m), 1.64 (8H, m), 1.78, 2.05 & 2.2–2.4 (total 2H, each m), 2.30 (2H, t, J=6.8 Hz), 3.00, 3.19, 3.27, 3.58, 3.68, 3.81, 4.1–4.3 & 4.88 (total 15H, each m), 7.43 (3H, m), 7.70 (2H, m), 12.81 (1H, brs).

EXAMPLE 26

2-(1-Docosanoyl-2-piperidyl)ethyl 4-methyltetrahydro-1(2H)-pyrazinecarboxylate (Compound 26)

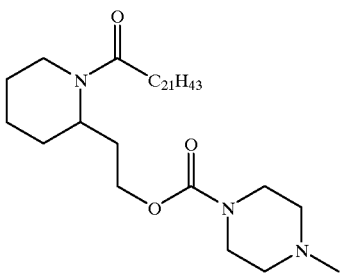

Pyridine (0.70 ml) and phenyl chlorocarbonate (0.80 ml) were added to a solution of 1-[2-(2-hydroxyethyl)piperidino]docosan-1-one (2.600 g), that was prepared in Example 16 (1), in methylene chloride (26 ml), while being cooled with ice. After being stirred for 2.5 hours at room temperature, the reaction mixture was diluted with chloroform, washed with 1N hydrochloric acid, saturated sodium hydrogencarbonate aqueous solution and saturated brine successively, dried over sodium sulfate anhydride, and concentrated. N-Methylpiperazine (0.71 ml) was added to the residue. After being stirred for 3 hours at 70° C., the reaction mixture was purified by silica gel column chromatography (silica gel 100 g, ethyl acetate (300 ml) and chloroform: methanol=50:1–30:1, succesively), thereby yielding the entitled compound (3.064 g) as white solid.

$^1$H-NMR (CDCl$_3$) δ: 0.88 (3H, t, J=6.8 Hz), 1.2–1.45 (36H, m), 1.62 (8H, m), 1.80 & 1.93 (total 1H, each m), 2.04 (1H, m), 2.2–2.4 (2H, m), 2.29 (3H, s), 2.36 (4H, m), 2.56 & 3.11 (total 1H, each t, J=13.7 Hz), 3.49 (4H, m), 3.66 & 4.58 (total 1H, each d, J=13.7 Hz), 3.97–4.19 (2H, m), 4.07 & 4.94 (total 1H, each brt).

EXAMPLE 27

2-(1-Docosanoyl-2-piperidyl)ethyl 4-methyltetrahydro- 1 (2H)-pyrazinecarboxylate hydrochloride (Compound 27)

4N Hydrochloric acid/ethyl acetate solution (1.46 ml) was added to a solution of 2-(1-docosanoyl-2-piperidyl)ethyl 4-methyltetrahydro-1(2H)-pyrazinecarboxylate (2.800 g) in ethyl acetate (28 ml), while being cooled with ice. The mixture was stirred for 30 minutes. After the reaction mixture was concentrated, the residue was recrystallized with ethyl acetate, thereby yielding the entitled compound (2.590 g) as white solid.

$^1$H-NMR (CDCl$_3$) δ: 0.88 (3H, t, J=6.8 Hz), 1.2–1.45 (36H, m), 1.5–1.9, 2.05 & 2.35 (total 10H, each m), 2.27 (2H, t, J=7.3 Hz), 2.81 (3H, s), 2.99, 3.09, 3.28, 3.67, 3.85, 4.21 & 4.87 (total 13H, each m), 12.79 (1H, brs).

EXAMPLE 28

2-[1-(4-Piperidinobutanoyl)-2-piperidyl]ethyl N-tetradecylcarbamate (Compound 28)

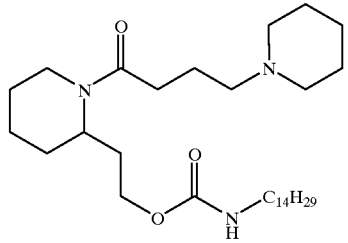

(1) 4-Chloro-1-[2-(2-hydroxyethyl)piperidino]-1-butanone

Triethylamine (3.60 ml) and 4-chlorobutyryl chloride (2.60 ml) were added to a solution of 2-(2-hydroxyethyl) piperidine (3.000 g) in methylene chloride solution (30 ml), while being cooled with ice. After being stirred for 2 hours at room temperature, the reaction mixture was diluted with chloroform, washed with 1N hydrochloric acid, saturated sodium hydrogencarbonate aqueous solution and saturated brine successively, dried over sodium sulfate anhydride, and concentrated. The residue was purified by silica gel column chromatography (silica gel 150 g, chloroform: methanol=60: 1~30:1), thereby yielding a crude (2.179 g) of the entitled compound as light yellow syrup.

(2) 1-(2-(2-Hydroxyethyl)piperidino]-4-piperidino-1-butanone

Piperidine (0.83 ml) was added to the crude (0.975 g) of 4-chloro-1-[2-(2-hydroxyethyl)piperidino]-1-butanone. After being stirred for 3.5 hours at 70~80° C., the reaction mixture was concentrated, thereby yielding a crude (1.097 g) of the entitled compound as light yellow syrup.

(3) 2-[1-(4-Piperidinobutanoyl)-2-piperidyl]ethyl N-tetradecylcarbamate

Triethylamine (1.14 ml) and tetradecyl isocyanate (1.864 g) were added to a solution of the crude (1.097 g) of 1-[2-(2-hydroxyethyl)piperidino]-4-piperidino-1-butanone in methylene chloride (11 ml). The mixture was stirred for 16 hours at room temperature. The insoluble matter was filtrated out under a vacuum and was washed with chloroform. The filtrate and the washings were mixed and the mixture was washed with saturated sodium hydrogencarbonate aqueous solution and saturated brine successively, dried over sodium sulfate anhydride, and concentrated. The residue was purified by silica gel column chromatography (silica gel 50 g, chloroform: methanol=30:1–10:1), thereby yielding the entitled compound (0.419 g) as light yellow solid.

$^1$H-NMR (CDCl$_3$) δ: 0.88 (3H, t, J=6.8 Hz), 1.2–1.35 (22H, m), 1.45 (4H, m), 1.60, 1.84 & 2.03 (total 14H, each m), 2.33 (2H, t, J=7.3 Hz), 2.40 (6H, m), 2.56 & 3.11 (total 1H, each t, J=13.2 Hz), 3.14 (2H, m), 3.68 & 4.54 (total 1H, each d, J=13.2 Hz), 4.00 & 4.11 (total 2H, each m), 4.02 & 4.93 (total 1H, each brt), 5.01 & 5.20 (total 1H, each brt).

| Compounding Example 1 Hair growth tonic | |
|---|---|
| Compound 5 | 0.5 wt % |
| Pyridoxine dioctanoate | 0.1 |
| Pantothenyl ethyl ether | 0.2 |
| Hinokitiol | 0.05 |
| Polyoxyethylene (12) polyoxypropylene (6) decyl tetradecyl | 1.0 |
| 1-Menthol | 0.1 |
| Disinfectants | Q.S. |
| 1,3-Butylene glycol | 3.0 |
| Ethanol | 70.0 |
| Purified water | Balance |

<Preparation Method>

Ethanol-soluble ingredients were added and dissolved into ethanol at room temperature while being stirred. Water-soluble ingredients were dissolved in purified water. The aqueous solution was added to the ethanol solution. After being uniformly mixed, the mixture was filtrated.

| Compounding Example 2 Hair regrowth promoting liquid lotion | |
|---|---|
| Compound 1 | 0.2 wt % |
| Carpronium chloride | 1.0 |
| Pantothenyl ethyl ether | 0.5 |
| Diphenhydrainine hydrochloride | 0.1 |
| Hinokitiol | 0.1 |
| dl-α-Tocopheryl acetate | 0.1 |
| Salicylic acid | 0.2 |
| 1-Menthol | 0.2 |
| Glycyrrhizinic acid | 0.1 |
| Sodium dl-pyrrolidone-carboxylate solution | 1.0 |
| Ethanol | 70.0 |
| Purified water | Balance |

<Preparation Method>

Ethanol-soluble ingredients were added and dissolved into ethanol at room temperature while being stirred. Water-soluble ingredients were dissolved in purified water. The aqueous solution was added to the ethanol solution. After being uniformly mixed, the mixture was filtrated.

| Compounding Example 3 Hair tonic | |
|---|---|
| Compound 3 | 0.1 wt % |
| Paeony root extract (1,3-butylene glycol extract) | 0.01 |
| Hinokitiol | 1.0 |
| Vitamin $B_6$ | 0.2 |
| Vitamin E acetate | 0.02 |
| Menthol | 0.2 |
| Swertia herb extract | 1.0 |
| Salicylic acid | 0.1 |
| Rosae rugosae flos extract (ethanol extract) | 0.5 |
| Propylene glycol | 2.0 |
| Sodium hyaluronate | 0.01 |
| Polyoxyethylene (10) monostearate | 2.0 |
| 75% Ethanol | Balance |

<Preparation Method>

Each of the above ingredients was added and dissolved into 75% ethanol successively with stirring to obtain a hair tonic.

| Compounding Example 4 Hair tonic | |
|---|---|
| Paeonia extract (ethanol extract) | 5.0 wt % |
| Compound 1 | 0.05 |
| Compound 2 | 0.05 |
| Hinokitiol | 1.0 |
| Vitamin $B_6$ | 0.2 |
| Vitamin E acetate | 0.02 |
| Menthol | 0.2 |
| Salicylic acid | 0.1 |
| Pueraria root extract (ethanol extract) | 0.5 |
| Propylene glycol | 2.0 |
| Sodium hyaluronate | 0.01 |
| Polyoxyethylene (10) monostearate | 2.0 |
| 75% Ethanol | Balance |

<Preparation Method>

Each of the above ingredients was added and dissolved into 75% ethanol successively with stirring to obtain a hair tonic.

| Compounding Example 5 Hair tonic | |
|---|---|
| Compound 10 | 0.05 wt % |
| 95% Ethanol | 50.0 |
| Monoammonium glycyrrhizinate | 0.05 |
| Paeonia extract (ethanol extract) | 0.05 |
| Paeony root extract (1,3-butylene glycol extract) | 0.02 |
| Saffron extract (ethanol extract) | 0.02 |
| Rosemary extract (ethanol extract) | 0.02 |
| Peppermint extract (ethanol extract) | 0.02 |
| Japanese angelica root extract (ethanol extract) | 0.02 |
| Althea extract (ethanol extract) | 0.02 |
| Rehmannia root extract (ethanol extract) | 0.02 |
| Coix extract (ethanol extract) | 0.02 |
| Sodium lauryl sulfate | 0.1 |
| N,N-dimethyl-2-decyltetradecylamineoxide | 0.5 |
| Polyoxyethylene (40) hydrogenated castor oil | 0.5 |
| Succinic acid | Q.S. |
| Perfume and coloring agent | Q.S. |
| Purified water | Balance |

<Preparation Method>

A hair tonic was prepared according to Compounding Example 1.

| Compounding Example 6 Hair lotion | |
|---|---|
| 95% Ethanol | 90.0 wt % |
| Vitamin E acetate | 0.05 |
| Compound 6 | 0.01 |
| Sodium lauryl sulfate | 0.06 |
| Propylene glycol | 0.1 |
| Polyoxyethylene (40) hydrogenated castor oil | 0.5 |
| Lactic acid | Q.S. |
| Sodium lactate | Q.S. |
| Perfume and coloring agent | Q.S. |
| Purified water | Balance |

<Preparation Method>

Polyoxyethylene (40) hydrogenated castor oil and perfume were dissolved in 95% ethanol. Then, purified water and the other ingredients were added and dissolved into the mixture successively with stirring to obtain a transparent liquid lotion.

| Compounding Example 7 Hair tonic | |
|---|---|
| Compound 7 | 0.1 wt % |
| Hinokitiol | 1.0 |
| Vitamin $B_6$ | 0.2 |
| Vitamin E acetate | 0.02 |
| Menthol | 0.2 |
| Swertia herb extract | 1.0 |
| Salicylic acid | 0.1 |
| Propylene glycol | 2.0 |
| Polyoxyethylene (10) monostearate | 2.0 |
| 75% Ethanol | Balance |

<Preparation Method>

Each of the above ingredients was added and dissolved into 75% ethanol successively with stirring to obtain a hair tonic.

| Compounding Example 8 Hair tonic | |
|---|---|
| Compound 11 | 0.5 wt % |
| Compound 12 | 0.1 |
| Hinokitiol | 1.0 |
| Vitamin $B_6$ | 0.2 |
| Vitamin E | 0.02 |
| Menthol | 0.2 |
| Salicylic acid | 0.1 |
| Propylene glycol | 2.0 |
| Sodium hyaluronate | 0.01 |
| Polyoxyethylene (10 mol) monostearate | 2.0 |
| 70% Ethanol | Balance |

<Preparation Method>

Each of the above ingredients was added and dissolved into 70% ethanol successively with stirring to obtain a hair tonic.

| Compounding Example 9 O/W type milky lotion | |
|---|---|
| (Phase A) | |
| Polyoxyethylene (60) hydrogenated castor oil | 2.0 wt % |
| Glycerin | 10.0 |
| Dipropylene glycol | 10.0 |

Compounding Example 9 O/W type milky lotion

| | |
|---|---|
| 1,3-Butylene glycol | 4.0 |
| Compound 14 | 0.1 |
| Polyethylene glycol 1500 | 5.0 |
| (Phase B) | |
| Isocetyl octanoate | 10.0 |
| Squalane | 5.0 |
| Vaseline | 2.0 |
| Propyl paraben | 2.0 |
| (Phase C) | |
| 1% Carboxyvinylpolymer aqueous solution | 30.0 |
| Sodium hexametaphosphate | 0.03 |
| Ion-exchanged water | 8.35 |
| (Phase D) | |
| Ion-exchanged water | 4.5 |
| (Phase E) | |
| Potassium hydroxide | 0.12 |
| Ion-exchanged water | Balance |

<Preparation Method>

Phases A and B were heated and dissolved, separately. Both were mixed and treated with a homomixer, thereby obtaining a gel. Phase D was then gradually added to this gel and dispersed by the homomixer. Then, Phases C and E were added to this gel dispersion successively, which were mixed and dissolved in advance separately. The mixture was emulsified by the homomixer to obtain an O/W type milky lotion.

Compounding Example 10 Cream

| | |
|---|---|
| (Phase A) | |
| N,N-Dimethyl-2-tetradecylamineoxide | 2.5 wt % |
| Liquid paraffin | 5.0 |
| Cetostearyl alcohol | 5.5 |
| Glyceryl monostealate | 3.0 |
| Polyoxyethylene (20) 2-octyldodecyl ether | 3.0 |
| Propyl paraben | 0.3 |
| Perfume | 0.1 |
| (Phase B) | |
| Compound 17 | 1.0 |
| Glycerin | 8.0 |
| Dipropylene glycol | 20.0 |
| Polyethylene glycol 4000 | 5.0 |
| Sodium hexametaphosphate | 0.005 |
| Ion-exchanged water | Balance |

<Preparation Method>

Phases A and B were heated and dissolved, separately. Both were mixed and emulsified by a homomixer to obtain a cream.

Compounding Example 11 Aerosol spray

| | |
|---|---|
| (Stock solution) | |
| 95% Ethanol | 50.0 wt % |
| Glycyrrhizic acid | 0.1 |
| Compound 21 | 0.5 |
| Swertia herb extract | 0.1 |
| Sodium laurylsulfate | 0.1 |
| Polyoxyethylene (40) hydrogenated castor oil | 0.5 |
| Lactic acid | Q.S. |
| Sodium lactate | Q.S. |

Compounding Example 11 Aerosol spray (continued)

| | |
|---|---|
| Perfume | Q.S. |
| Ion-exchanged water | Balance |
| (Filling formulation) | |
| Stock solution | 50.0 |
| Liquefied petroleum gas | 50.0 |

<Preparation Method>

A stock solution was prepared by mixing and dissolving the ingredients of stock solution. This stock solution was filled into a can and a valve was fit thereto. Liquefied petroleum gas was filled into the can to obtain an aerosol spray.

Compounding Example 12 Shampoo

| | |
|---|---|
| (1) Sodium cocoylmethyltaurate | 2.0 wt % |
| (2) Polyoxyethylene (8) oleyl ether | 2.0 |
| (3) Lauric acid diethanolamide | 4.0 |
| (4) Ethylene glycol fatty acid ester | 1.0 |
| (5) Glycerine | 0.2 |
| (6) Menthol | 0.1 |
| (7) Compound 23 | 0.1 |
| (8) Disodium edetate | 0.1 |
| (9) Perfume | Q.S. |
| (10) Purified water | Balance |

<Preparation Method>

The ingredient (10) was heated up to 70° C. The ingredients (1)–(9) were added to the heated ingredient (10) successively and the mixture was mixed and dissolved with stirring. The mixture was cooled to obtain a shampoo.

Compounding Example 13 Rinse

| | |
|---|---|
| (1) Stearyl trimethyl ammonium chloride | 1.5 wt % |
| (2) Dimethyl polysiloxane (20 cs) | 3.0 |
| (3) Polyoxyethylene (10) oleyl ether | 1.0 |
| (4) Glycerine | 5.0 |
| (5) Compound 27 | 0.5 |
| (6) 4-tert-Butyl-4'-methoxydibenzoylmethane | Q.S. |
| (7) Ultraviolet absorber | Q.S. |
| (8) Purified water | Balance |

<Preparation Method>

The water phase was prepared by adding the ingredients (1), (3) and (4) to the ingredient (8) and heating up to 70° C. The oil phase was prepared by heating and dissolving the other ingredients up to 70° C. The oil phase was added to the water phase and the mixture was mixed with stirring by an emulsifier. The mixture was cooled to obtain a rinse.

Compounding Example 14 Scalp treatment

| | |
|---|---|
| (Stock solution) | |
| (1) Liquid paraffin | 27.0 wt % |
| (2) Stearic acid | 5.0 |
| (3) Cetanol | 5.0 |
| (4) Sorbitan monooleate | 2.0 |
| (5) Polyoxyethylene sorbitan monooleate | 3.0 |
| (6) Compound 23 | 0.1 |

Compounding Example 14 Scalp treatment (-continued)

| | |
|---|---|
| (7) 1,3-Butylene glycol | 5.0 |
| (8) Antiseptic | Q.S. |
| (9) Purified water | Balance |
| (Filling formulation) | |
| Stock solution | 50.0 |
| Liquefied petroleum gas | 50.0 |

<Preparation Method>

The ingredients (5) and (6) were dissolved into ingredients (1) to (4). After being dissolved with heating up to 80° C., the mixture was cooled down to 30° C. This mixture was added to the mixed solution of the ingredients (7) to (9), which was maintained at 30° C., and mixed with stirring to obtain a stock solution. This stock solution was filled into a can together with a propellant to obtain a scalp treatment.

Compounding Example 15 Scalp treatment

| | |
|---|---|
| (Stock solution) | |
| (1) Hinokitiol | 0.1 wt % |
| (2) Swertia herb extract | 1.0 |
| (3) Vitamin $B_6$ | 0.1 |
| (4) Vitamin E | 0.01 |
| (5) Menthol | 0.1 |
| (6) Salicylic acid | 0.001 |
| (7) Compound 12 | 0.1 |
| (8) Polyoxyethylene sorbitan monooleate | 0.1 |
| (9) Propylene glycol | 2.0 |
| (10) 75% Ethanol | Balance |
| (Filling formulation) | |
| Stock solution | 50.0 |
| Dimethyl ether | 50.0 |

<Preparation Method>

A scalp treatment was prepared according to Compounding Example 14.

In the following, the compounds and manufacturing processes thereof in accordance with the present invention are exemplified.

Compound 29

{2-[1-(N-Cyclohexylcarbamoyl)-2-piperidyl]ethoxy}-N-[3-(dimethylamino)propyl]formamide

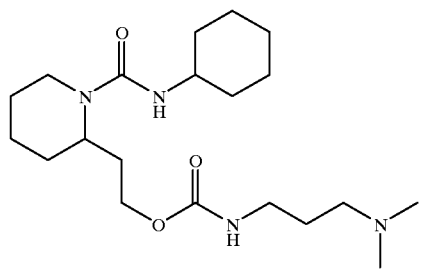

In Example 1, cyclohexylisocyanate is used in the place of octadecyl isocyanate to obtain the entitled compound.

Compound 30

[2-[1-[N-(4-Butylphenyl)carbamoyl]-2-piperidyl]ethoxy]-N-[ 3-(dimethylamino)propyl]formamide

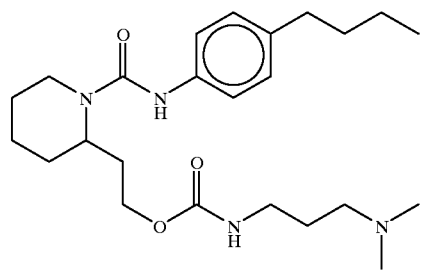

In Example 1, 4-butylphenyl isocyanate is used in the place of octadecyl isocyanate to obtain the entitled compound.

Compound 31

N-[3 -(Dimethylamino)propyl]-{5-[1-(N-phenethylcarbamoyl)-2-piperidyl]pentyloxy}formamide

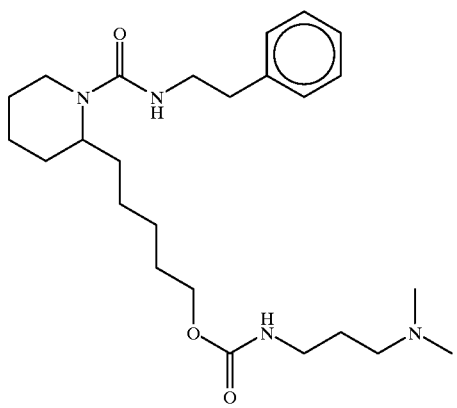

In Example 1, 2-(5-(hydroxypentyl)piperidine and phenethyl isocyanate are used in the place of 2-(2-hydroxyethyl)piperidine and octadecyl isocyanate, respectively, to obtain the entitled compound.

Compound 32

N-(2-Aziridinoethyl)-{2-[1-(N-octadecylcarbamoyl)-2-piperidyl]ethoxy}formamide

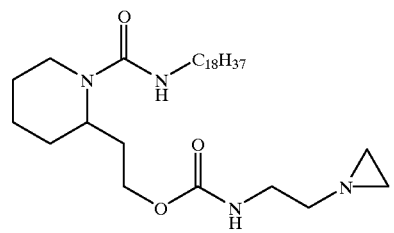

In Example 1 (2), 1-(2-aminoethyl)aziridine is used in the place of N,N-dimethyl-1,3-propanediamine to obtain the entitled compound.

Compound 33

{2-[1-(N-Octadecylcarbamoyl)-2-piperidyl]ethoxy}-N-(2-pyrrolidinoethyl)formamide

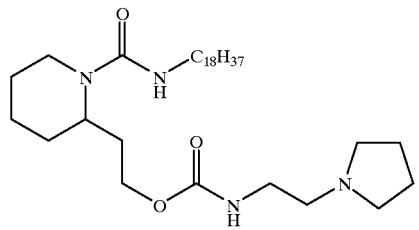

In Example 1 (2), 1-(2-aminoethyl)pyrrolidine is used in the place of N,N-dimethyl-1,3-propanediamine to obtain the entitled compound.

Compound 34

N-[3-(4-Methylpiperidino)propyl]-{2-[1-(N-octadecylcarbamoyl)-2-piperidyl]ethoxy}formamide

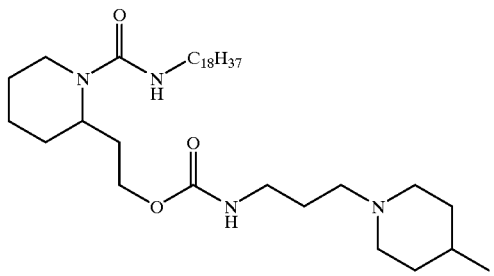

In Example 1 (2), 1-(3-aminopropyl)-4-methylpiperidine is used in the place of N,N-dimethyl-1,3-propanediamine to obtain the entitled compound.

Compound 35

{2-[1-(N-Octadecylcarbamoyl)-2-piperidyl]ethoxy}-N-[2-(1-piperazyl)ethyl]formamide dihydrochloride

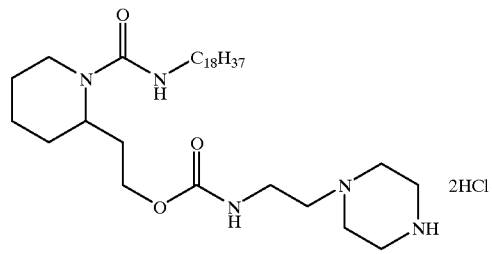

In Example 1 (2), 1-(2-aminoethyl)-4-benzyloxycarbonylpiperazine is used in the place of N,N-dimethyl-1,3-propanediamine to obtain {2-[1-(N-octadecylcarbamoyl)-2-piperidyl]ethoxy}-N-[2-(4-benzyloxycarbonyl-piperazyl)ethyl]formamide.

This compound is subjected to catalytic reduction in the presence of 10% palladium-carbon to obtain {2-[1-(N-octadecylcarbamoyl)-2-piperidyl]ethoxy}-N-[2-(1-piperazyl)ethyl]formamide.

In the similar manner to Example 2, this compound is converted into its hydrochloride to obtain the entitled compound.

Compound 36

{2-[1-(N-Octadecylcarbamoyl)-2-piperidyl]ethoxy}-N-(5-pyrrolidinopentyl)formamide

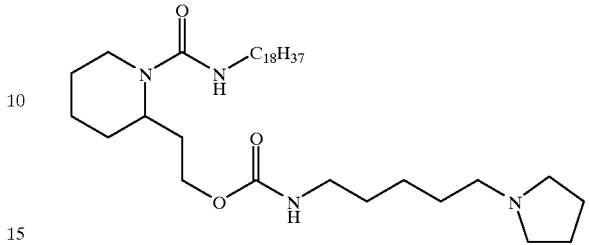

In Example 1 (2), 5-pyrrolidinoamylamine is used in the place of N,N-dimethyl-1,3-propanediamine to obtain the entitled compound.

Compound 37

N-[3-(1-Imidazolyl)propyl]-{2-[1-(N-octadecylcarbamoyl)-2-piperidyl]ethoxy}formamide

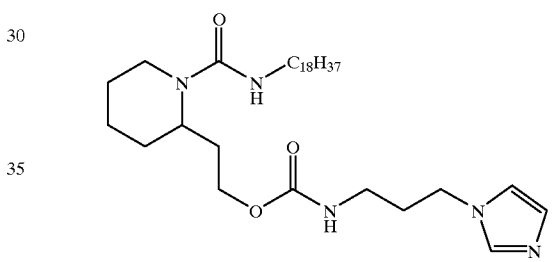

In Example 1 (2), 1-(3-aminopropyl)imidazole is used in the place of N,N-dimethyl-1,3-propanediamine to obtain the entitled compound.

Compound 38

{2-[1-(N-Octadecylcarbamoyl)-2-piperidyl]ethoxy}-N-[3-(2-oxopyrrolidino)propyl]formamide

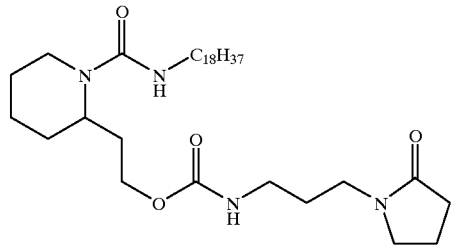

In Example 1 (2), 1-(3-aminopropyl)-2-pyrrolidinone is used in the place of N,N-dimethyl-1,3-propanediamine to obtain the entitled compound.

Compound 39

N-[2-(Diisobutylamino)ethyl]-{2-[1-(N-octadecylcarbamoyl)-2-piperidyl]ethoxy}formamide

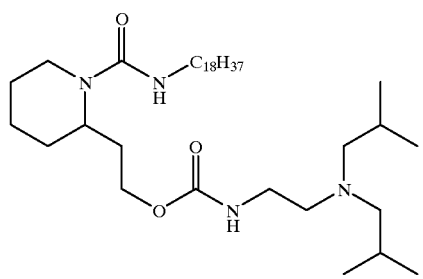

In Example 1 (2), N,N-diisobutylethylenediamine is used in the place of N,N-dimethyl-1,3-propanediamine to obtain the entitled compound.

Compound 40

N-[4-(Diethylamino)butyl]-{2-[1-(N-octadecylcarbamoyl)-2-piperidyl]ethoxy}formamide

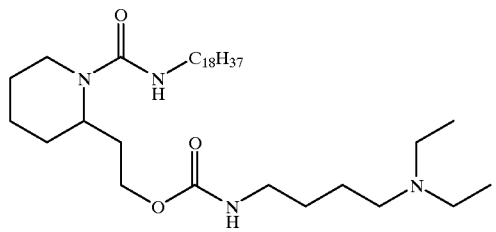

In Example 1 (2), 4-diethylaminobutylamine is used in the place of N,N-dimethyl-1,3-propanediamine to obtain the entitled compound.

Compound 41

N-[3-(Methylphenylamino)propyl]- {2-[1-(N-octadecylcarbamoyl)-2-piperidyl]ethoxy}formamide

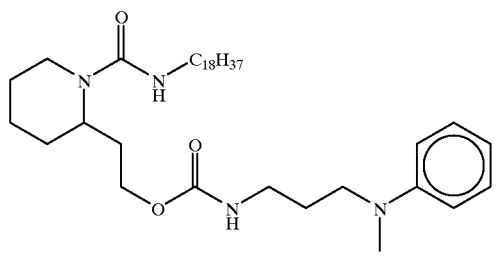

In Example 1 (2), N-(3-aminopropyl)-N-methylaniline is used in the place of N,N-dimethyl-1,3-propanediamine to obtain the entitled compound.

Compound 42

N-(2-Aminoethyl)-{2-[1-(N-octadecylcarbamoyl)-2-piperidyl]ethoxy}formamide

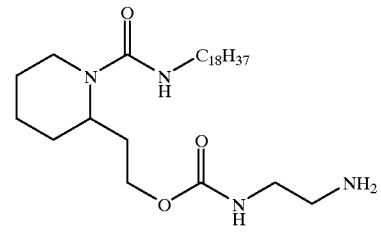

In Example 1 (2), ethylenediamine is used in the place of N,N-dimethyl-1,3-propanediamine to obtain the entitled compound.

Compound 43

N-[3 -(Dibenzylamino)propyl]-{2-[1-(N-octadecylcarbamoyl)-2-piperidyl]ethoxy}formamide

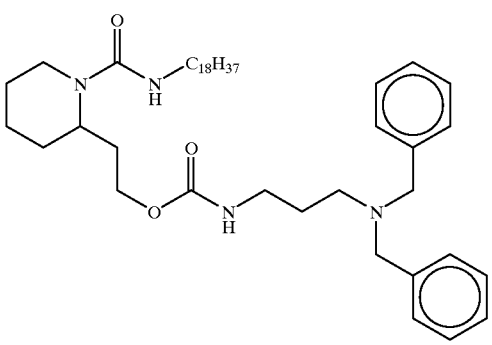

In Example 1 (2), N,N-dibenzyl-1,3-propanediamine is used in the place of N,N-dimethyl-1,3-propanediamine to obtain the entitled compound.

Compound 44

N-{3-[Bis(2-hydroxyethyl)amino]propyl}-{2-[1-(N-octadecylcarbamoyl)-2-piperidyl]ethoxy}formamide

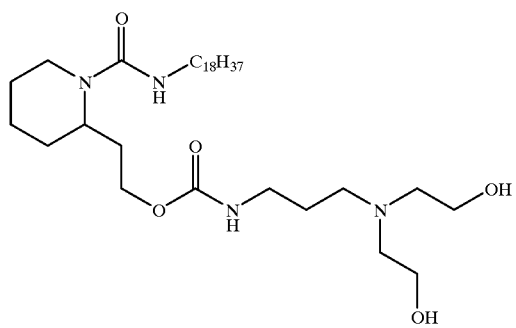

In Example 1 (2), N-(3-aminopropyl)diethanolamine is used in the place of N,N-dimethyl-1,3-propanediamine to obtain the entitled compound.

Compound 45

N-(Dimethylamino)-{2-[1-(N-octadecylcarbamoyl)-2-piperidyl]ethoxy}formamide

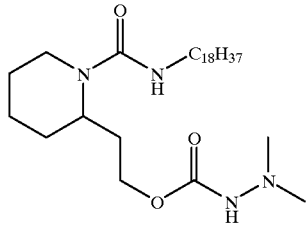

In Example 1 (2), N,N-dimethylhydrazine is used in the place of N,N-dimethyl-1,3-propanediamine to obtain the entitled compound.

Compound 46

{2-[4-Chloro-1-(N-octadecylcarbamoyl)-2-piperidyl]ethoxy}-N-[3-(dimethylamino)propyl]formamide

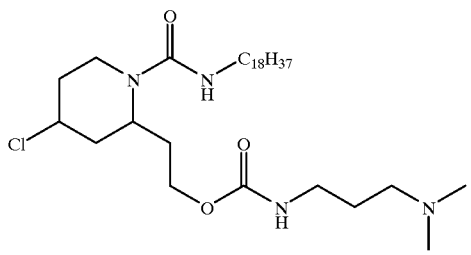

In Example 1, 4-chloro-2-(2-hydroxyethyl)piperidine is used in the place of 2-(2-hydroxyethyl)piperidine to obtain the entitled compound.

Compound 47

N-[3-(Dimethylamino)propyl]- {2-[3-methyl-1-(N-octadecylcarbamoyl)-2-piperidyl]ethoxy}formamide

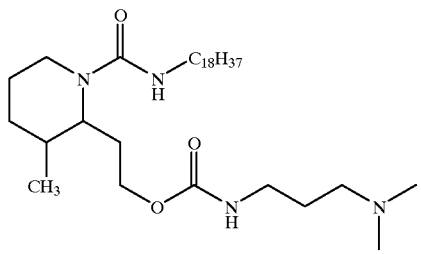

In Example 1, 2-(2-hydroxyethyl)-3-methylpiperidine is used in the place of 2-(2-hydroxyethyl)piperidine to obtain the entitled compound.

Compound 48

{2-[5-Acetyl-1-(N-octadecylcarbamoyl)-2-piperidyl]ethoxy}-N-[3-(dimethylamino)propyl]formamide

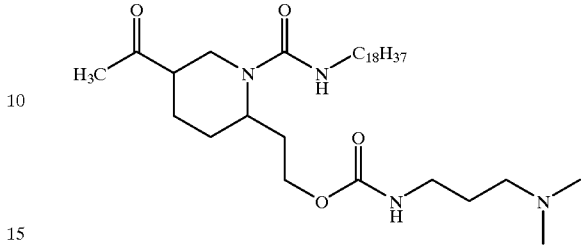

In Example 1, 5-acetyl-2-(2-hydroxyethyl)piperidine is used in the place of 2-(2-hydroxyethyl)piperidine to obtain the entitled compound.

Compound 49

N-[3-(Dimethylamino)propyl]-{2-[4-nitro-1 -(N-octadecylcarbamoyl)-2-piperidyl]ethoxy}formamide

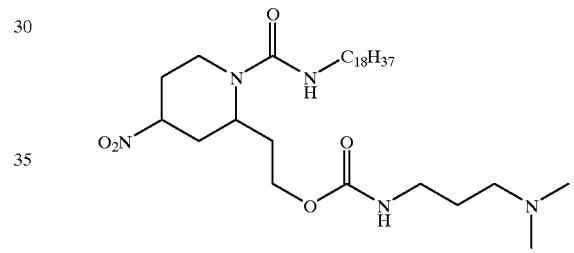

In Example 1, 2-(2-hydroxyethyl)-4-nitropiperidine is used in the place of 2-(2-hydroxyethyl)piperidine to obtain the entitled compound.

Compound 50

N-[3-(Dimethylamino)propyl]-{2-[5-methoxycarbonyl- 1 -(N-octadecylcarbamoyl)-2-piperidyl]ethoxy}formamide

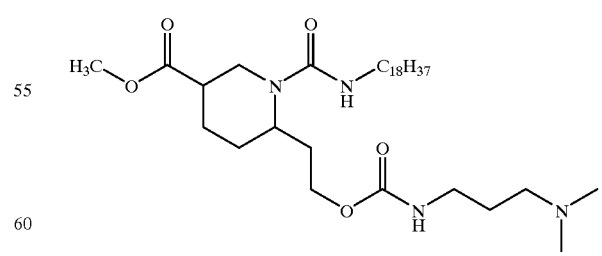

In Example 1, 2-(2-hydroxyethyl)-5-methoxycarbonylpiperidine is used in the place of 2-(2-hydroxyethyl) piperidine to obtain the entitled Compound 51

{2-[5-Carbamoyl-1-(N-octadecylcarbamoyl)-2-piperidyl]ethoxy}-N-[3-(dimethylamino)propyl]formamide

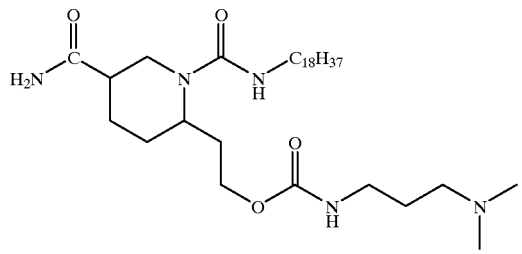

In Example 1, 5-carbamoyl-2-(2-hydroxyethyl)piperidine is used in the place of 2-(2-hydroxyethyl)piperidine to obtain the entitled compound.

Compound 52

N-[3-(Dimethylamino)propyl]-{2-[5-methylcarbamoyl-1-(N-octadecylcarbamoyl)-2-piperidyl]ethoxy}formamide

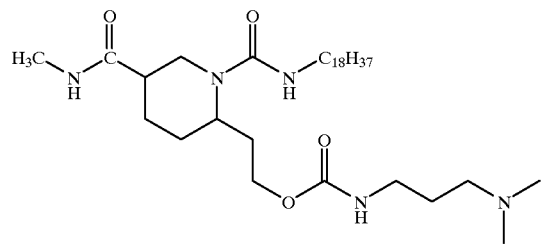

In Example 1, 2-(2-hydroxyethyl)-5-methylcarbamoylpiperidine is used in the place of 2-(2-hydroxyethyl)piperidine to obtain the entitled compound.

Compound 53

N-[3-(Dimethylamino)propyl]-{2-[4-dimethylamino-1-(N-octadecylcarbamoyl)-2-piperidyl]ethoxy}formamide

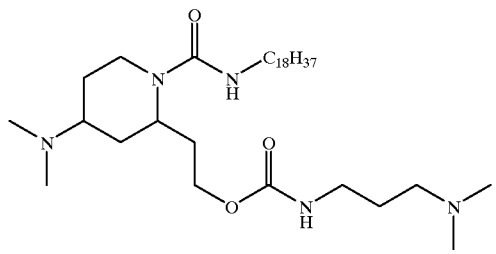

In Example 1, 4-dimethylamino-2-(2-hydroxyethyl)piperidine is used in the place of 2-(2-hydroxyethyl)piperidine to obtain the entitled compound.

Compound 54

{2-[4-Acetylamino-1-(N-octadecylcarbamoyl)-2-piperidyl]ethoxy}-N-[3-(dimethylamino)propyl]formamide

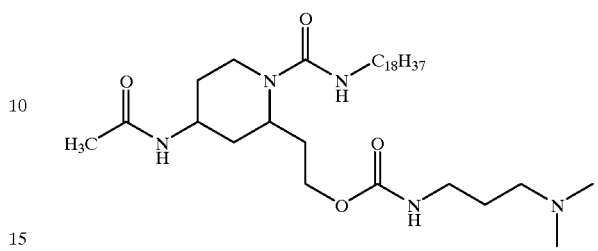

In Example 1, 4-acetylamino-2-(2-hydroxyethyl)piperidine is used in the place of 2-(2-hydroxyethyl)piperidine to obtain the entitled compound.

Compound 55

N-[3-(Dimethylamino)propyl]-{2-[4-methoxy-1-(N-octadecylcarbamoyl)-2-piperidyl]ethoxy}formamide

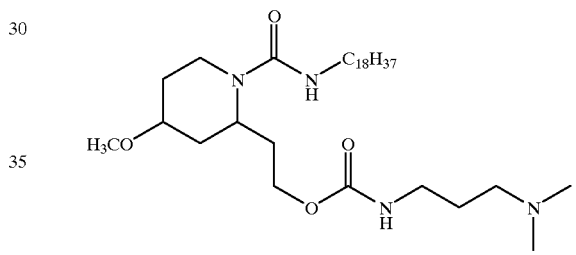

In Example 1, 4-methoxy-2-(2-hydroxyethyl)piperidine is used in the place of 2-(2-hydroxyethyl)piperidine to obtain the entitled compound.

Compound 56

{2-[4-Acetoxy-1-(N-octadecylcarbamoyl)-2-piperidyl]ethoxy}-N-[3-(dimethylamino)propyl]formamide

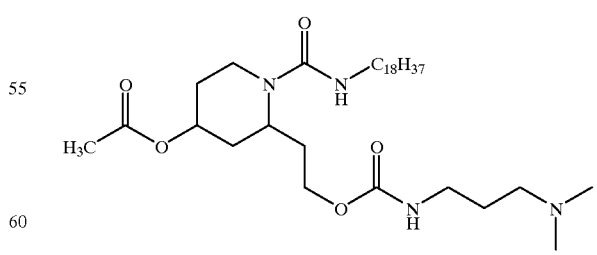

In Example 1, 4-acetoxy-2-(2-hydroxyethyl)piperidine is used in the place of 2-(2-hydroxyethyl)piperidine to obtain the entitled compound.

Compound 57

N-[3-(Dimethylamino)propyl]-N-methyl-{2-[1-(N-octadecylcarbamoyl)-2-piperidyl]ethoxy}formamide

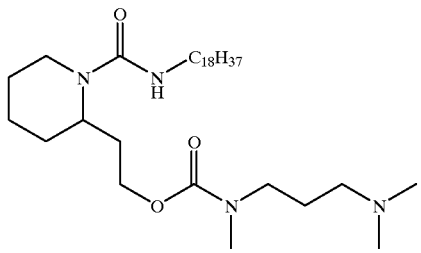

In Example 1 (2), N,N,N'-trimethyl-1,3-propanediamine is used in the place of N,N-dimethyl-1,3-propanediamine to obtain the entitled compound.

Compound 58

N-Acetyl-{2-[1-(N-acetyl-N-octadecylcarbamoyl)-2-piperidyl]ethoxy}-N-[3-(dimethyl amino)propyl]formamide

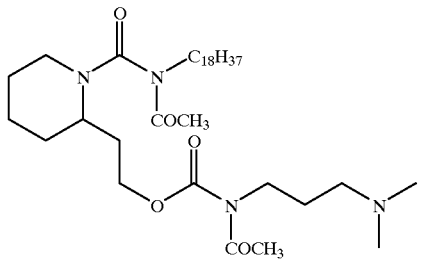

N-[3-(Dimethylamino)propyl]-{2-[1-(N-octadecylcarbamoyl)-2-piperidyl]ethoxy}formamide obtained in Example I is subjected to acetylation to obtain the entitled compound.

Compound 59

N-[3 -(Dimethylamino)propyl]-N-methylcarbamoyl-{2-[1-(N-methylcarbamoyl-N-octadecylcarbamoyl)-2-piperidyl]ethoxy}formamide

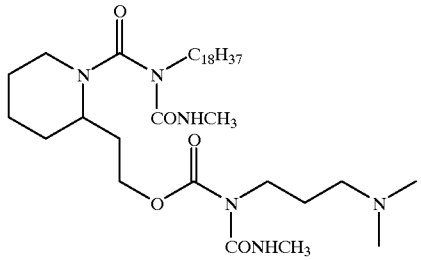

N-[3-(Dimethylamino)propyl]-{2-[1-(N-octadecylcarbamoyl)-2-piperidyl]ethoxy}formamide obtained in Example 1 is subjected to methylcarbamoylation to obtain the entitled compound.

Compound 60

[2-[1-[N-[3-(Dimethylamino)propyl]carbamoyl]-2-piperidyl]ethoxy]-N-octadecyl formamide

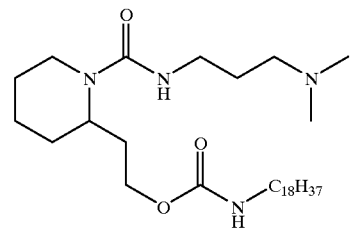

In Example 1 (1), 3-(dimethylamino)propyl isocyanate is used in the place of octadecyl isocyanate to obtain N-[3-(dimethylamino)propyl]-[2-(2-hydroxyethyl) piperidino] formamide.

In Example 1 (2), this compound and octadecylamine are used in the place of [2-(2-hydroxyethyl)piperidino]-N-octadecylformamide and N,N-dimethyl-1,3-propanediamine, respectively, to obtain the entitled compound.

Compound 61

[2- [1-[N-(2-Morpholinoethyl)carbamoyl]-2-piperidyl]ethoxy]-N-octadecylformamide

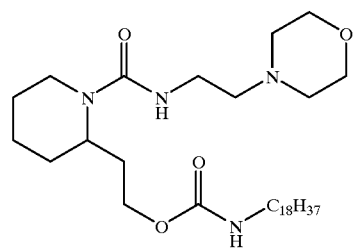

In Example 1 (1), 2-morpholinoethyl isocyanate is used in the place of octadecyl isocyanate to obtain [2-(2-hydroxyethyl)piperidino]-N-(2-morpholinoethyl) formamide.

In Example 1 (2), this compound and octadecylamine are used in the place of [2-(2-hydroxyethyl)piperidino]-N-octadecylformamide and N,N-dimethyl-1,3-propanediamine, respectively, to obtain the entitled compound.

Compound 62

[2-[1-[N-[3-(Dimethylamino)propyl]carbamoyl]-2-piperidyl]ethoxy]-N-methyl-N-octadecylformamide

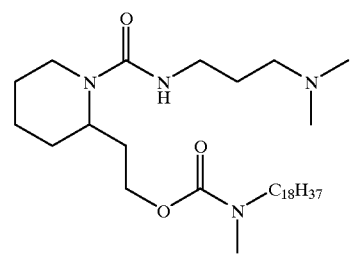

In Example 1 (2), N-[3-(dimethylamino)propyl]-[2-(2-hydroxyethyl)piperidino]formamide obtained in the way of manufacturing Compound 60 and N-methyl-N-octadecylamine are used in the place of [2-(2-hydroxyethyl) piperidino]-N-octadecylformamide and N,N-dimethyl-1,3- propanediamine, respectively, to obtain the entitled compound.

Compound 63

[2-[2-[4-(Dimethylamino)butoxy]ethyl]piperidino]-N-methyl-N-octadecylformamide

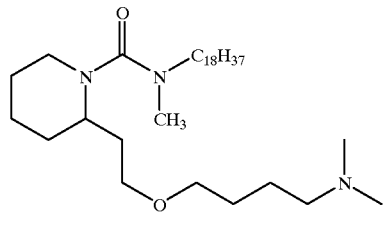

[2-(2-Hydroxyethyl)piperidine is reacted with phenyl chlorocarbonate in methylene chloride in the presence of pyridine and further reacted with N-methyl-N-octadecylamine to obtain [2-(2-hydroxyethyl)piperidino]-N-methyl-N-octadecyl formamide.

This compound and 1-bromo-4-chlorobutane are reacted in acetone in the presence of potassium carbonate at reflux temperature to obtain {2-[2-(4-chlorobutoxy)ethyl]piperidino}-N-methyl-N-octadecylformamide.

This compound and dimethylamine are reacted in acetone in the presence of potassium carbonate at reflux temperature to obtain the entitled compound.

Compound 64

N-Methyl-{2-[2-(2-morpholinoethoxy)ethyl]piperidino}-N-octadecylformamide

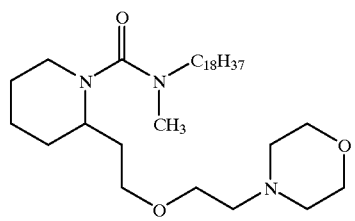

{2-[2-(4-Chlorobutoxy)ethyl]piperidino}-N-methyl-N-octadecylformamide obtained in the way of manufacturing Compound 63 and morpholine are reacted in acetone in the presence of potassium carbonate at reflux temperature, to obtain the entitled compound.

Compound 65

N-[3-(Dimethylamino)propyl]-{2-[2-(octadecyloxy)ethyl]piperidino}formamide

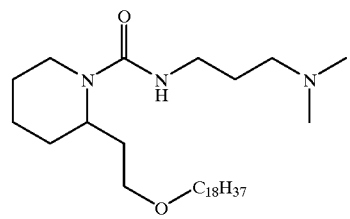

In Example 1 (1), 3-chloropropyl isocyanate is used in the place of octadecyl isocyanate to obtain N-(3-chloropropyl)-12-(2-hydroxyethyl)piperidino]formamide.

This compound and 1-bromooctadecane are reacted in acetone in the presence of potassium carbonate at reflux temperature to obtain N-(3-chloropropyl)-{2-[2-(octadecyloxy)ethyl]piperidino}formamide.

This compound and dimethylamine are reacted in acetone in the presence of potassium carbonate at reflux temperature to obtain the entitled compound.

Compound 66

2-[1-(N-Octadecylcarbamoyl)-2-piperidyl]ethyl 4-(dimethylamino)butanoate

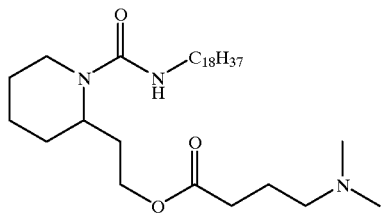

DCC is added to N,N-dimethylformamide solution of [2-(2-hydroxyethyl)piperidino]-N-octadecylformamide and 4-(dimethylamino)butyrate, and then tha mixture is reacted at room temperature to obtain the entitled compound.

Compound 67

[2-[2-[1-[N-[3-(Dimethylamino)propyl]carbamoyl]]piperidyl]ethyl]octadecanoate

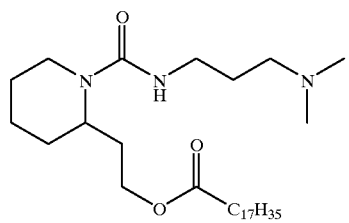

DCC is added to N,N-dimethylformamide solution of N-[3-(dimethylamino)propyl]-[2-(2-hydroxyethyl)piperidino]formamide obtained in the way of manufacturing Compound 60 and stearic acid, and then the mixture is reacted at room temperature to obtain the entitled compound.

Compound 68

2-[2-[3-(Dimethylamino)propylamino]ethyl)piperidino]-N-methyl-N-octadecylformamide

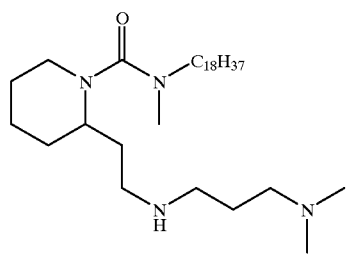

1,4-Dioxane solution of [2-(2-hydroxyethyl)piperidino]-N-methyl-N-octadecyl formamide obtained in the way of manufacturing Compound 63 and p-toluenesulfonyl chloride to sodium hydroxide solution, and trhen the mixture is reacted at room temperature to obtain N-methyl-N-octadecyl- { 2-[2-(tosyloxy)ethyl]piperidino}formamide.

This compound and N,N-dimethyl-1,3-propanediamine are reacted in acetone in the presence of potassium carbonate at reflux temperature to obtain the entitled compound.

Compound 69
N-Methyl-{2-[2-(3-morpholinopropylamino)ethyl]piperidino}-N-octadecylformamide

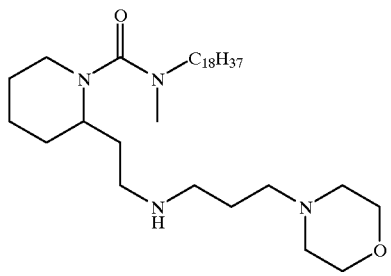

N-Methyl-N-octadecyl-{2-[2-(tosyloxy)ethyl]piperidino) formamide obtained in the way of manufacturing Compound 68 and 1-(3-aminopropyl)morpholine are reacted in acetone in the presence of potassium carbonate at reflux temperature to obtain the entitled compound.

Compound 70
N-[3-(Dimethylamino)propyl]-N-methyl-{2-2-(octadecylamino)ethyl]piperidino}formamide

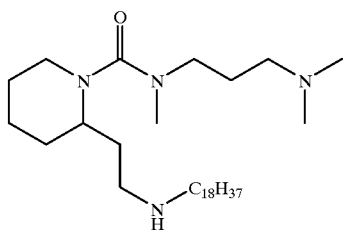

2-(2-Hydroxyethyl)piperidine and phenyl chlorocarbonate are reacted in methylene chloride in the presence of pyridine and further reacted with N,N,N'-trimethyl-1,3-propanediamine to obtain N-[3-(dimethylamino)propyl]-[2-(2-hydroxyethyl)piperidino]-N-methylformamide.

1,4-Dioxane solution of this compound and p-toluenesulfonyl chloride is added to sodium hydroxide solution, and the mixture is reacted at room temperature to obtain N-[3-(dimethylamino)propyl]-N-methyl-{2-[2-(tosyloxy)ethyl]piperidino}formamide.

This compound and octadecylamine are reacted in acetone in the presence of potassium carbonate at reflux temperature to obtain the entitled compound.

Compound 71
N-Methyl-N-(3-morpholinopropyl)-{2-[2-(octadecylamino)ethyl]piperidino}formamide

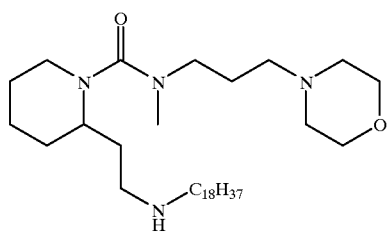

2-(2-Hydroxyethyl)piperidine and phenyl chlorocarbonate are reacted in methylene chloride in the presence of pyridine and further reacted with 4-[3-(methylamino)propyl]morpholine to obtain [2-(2-hydroxyethyl)piperidino]-N-methyl-N-(3-morpholinopropyl)formamide.

1,4-Dioxane solution of this compound and p-toluenesulfonyl chloride is added to sodium hydroxide solution, and the mixture is reacted at room temperature to obtain N-methyl-N-(3-morpholinopropyl)-{2-[2-(tosyloxy)ethyl]piperidino}formamide.

This compound and octadecylamine are reacted in acetone in the presence of potassium carbonate at reflux temperature to obtain the entitled compound.

Compound 72
[2-[1-(12-Cyclohexyldodecyl)-2-piperidyl]ethoxy}-N-3-(dimethylamino)propyl]formamide

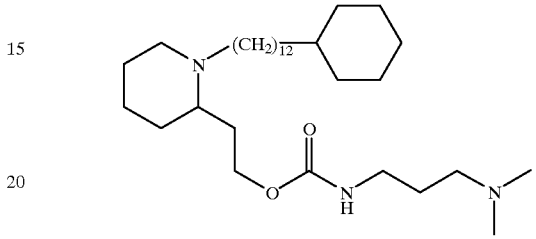

In Example 14, 1-bromo-12-cyclohexyldodecane is used in the place of 1-bromoocatadecane to obtain the entitled compound.

Compound 73
[2-[1-[3-(Dimethylamino)propyl]-2-piperidyl]ethoxy]-N-octadecylformamide

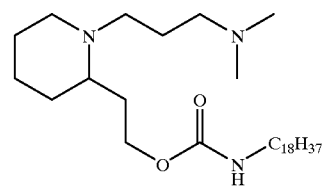

In Example 14 (1), 1-bromo-3-dimethylaminopropane is used in the place of 1-bromooctadecane to obtain 2-{1-[3-(dimethylamino)propyl]-2-piperidyl}ethan-1-ol.

In Example 14 (2), this compound and octadecylamine are used in the place of 2-(1-octadecyl-2-piperidyl)ethan-1-ol and N,N-dimethyl-1,3-propanediamine, respectively, to obtain the entitled compound.

Compound 74
2-[2-[4-(Dimethylamino)butoxy]ethyl]-1-octadecylpiperidine

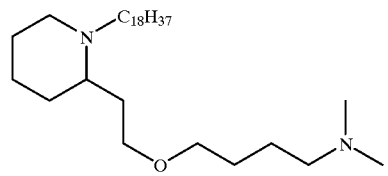

2-(1-Octadecyl-2-piperidyl)ethan-1-ol and 1-bromo-4-chlorobutane are reacted in acetone in the presence of potassium carbonate at reflux temperature to obtain 2-[2-(4-chlorobutoxy)ethyl]-1-octadecylpiperidine.

This compound and dimethylamine are reacted in acetone in the presence of potassium carbonate at reflux temperature to obtain the entitled compound.

Compound 75

1-[3-(Dimethylamino)propyl]-2-[2-(octadecyloxy)ethyl]piperidine

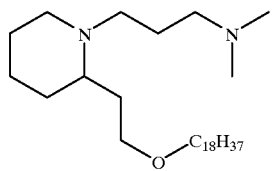

In Example 14 (1), 1-bromo-3-chloropropane is used in the place of 1-bromooctadecane to obtain 2-[1-(3-chloropropyl)-2-piperidyl]ethan-1-ol.

This compound and 1-bromooctadecane are reacted in acetone in the presence of potassium carbonate at reflux temperature to obtain 1-(3-chloropropyl)-2-[2-(octadecyloxy)ethyl]piperidine.

This compound and dimethylamine are reacted in acetone in the presence of potassium carbonate at reflux temperature to obtain the entitled compound.

Compound 76

2-(1-Octadecyl-2-piperidyl)ethyl 3-(dimethylamino)propylcarboxylate

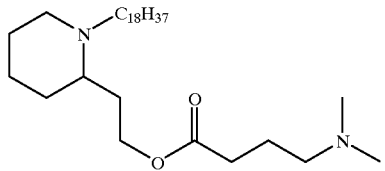

DCC is added to N,N-dimethylformamide solution of 2-(1-octadecyl-2-piperidyl) ethan-1-ol and 4-(dimethylamino)butyrate, and then the mixture is reacted at room temperature to obtain the entitled compound.

Compound 77

2-{1-[3-(Dimethylamino)propyl]-2-piperidyl}ethyl octadecanoate

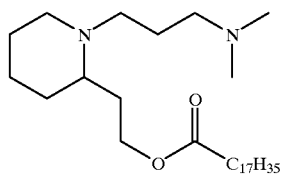

DCC is added to N,N-dimethylformamide solution of 2-{1-[3-(dimethylamino) propyl]-2-piperidyl}ethan-1-ol obtained in the way of manufacturing Compound 73 and stearic acid, and then the mixture is reacted at room temperature to obtain the entitled compound.

Compound 78

1-Octadecyl-2-{2-[3-(dimethylamino)propylamino]ethyl}piperidine

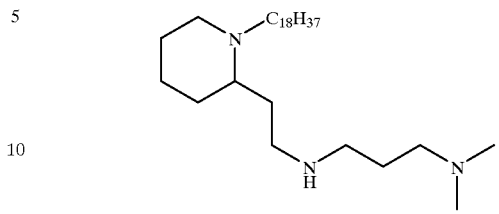

1,4-Dioxane solution of 2-(1-octadecyl-2-piperidyl)ethan-1-ol and p-toluenesulfonyl chloride is added to sodium hydroxide solution and then the mixture is reacted at room temperature to obtain 1-octadecyl-2-[2-(tosyloxy)ethyl]piperidine.

This compound and N,N-dimethyl-1,3-propanediamine are reacted in acetone in the presence of potassium carbonate at reflux temperature to obtain the entitled compound.

Compound 79

1-[3-(Dimethylamino)propyl]-2-[2-(octadecylamino)ethyl]piperidine

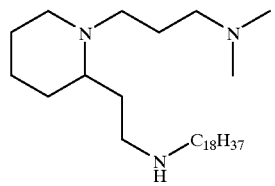

1,4-Dioxane solution of 2-{1-[3-(dimethylamino)propyl]-2-piperidyl}ethan-1-ol obtained in the way of manufacturing Compound 73 and p-toluenesulfonyl chloride is added to sodium hydroxide solution and then the mixture is reacted at room temperature to obtain 1-[3-(dimethylamino)propyl]-2-12-(tosyloxy)ethyl]piperidine.

This compound and octadecylamine are reacted in acetone in the presence of potassium carbonate at reflux temperature to obtain the entitled compound.

Compound 80

[2-[1-[4-(Dimethylamino)butanoyl]-2-piperidyl]ethoxy]-N-octadecylformamide

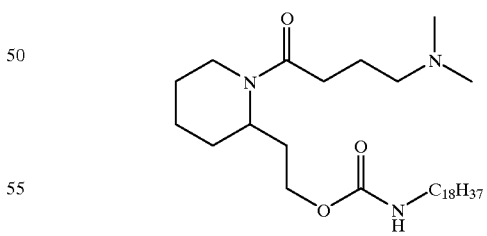

2-(2-Hydroxyethyl)piperidine, HOBt and WSCI are added to N,N-dimethylformamide solution of 4-(dimethylamino)butyrate while being cooled with ice and the mixture is reacted at room temperature to obtain 1-[4-(dimethylamino)butanoyl]-2-(2-hydroxyethyl)piperidine.

In Example 5 (2), this compound and octadecylamine are used in the place of 1-[2-(2-hydroxyethyl)piperidino]octadecan-1-one and N,N-dimethyl-1,3-propanediamine, respectively, to obtain the entitled compound.

Compound 81
2-[2-[4-(Dimethylamino)butoxy]ethyl]-1-octadecanoylpiperidine

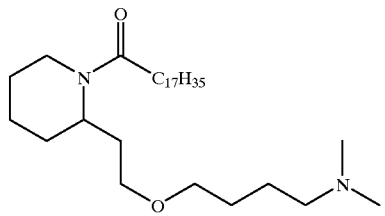

1-[2-(2-Hydroxyethyl)piperidino]octadecan-1-one and 1-bromo-4-chlorobutane are reacted in acetone in the presence of potassium carbonate at reflux temperature to obtain 2-[2-(4-chlorobutoxy)ethyl]-1-octadecanoylpiperidine.

This compound and dimethylamine are reacted in acetone in the presence of potassium carbonate at reflux temperature to obtain the entitled compound.

Compound 82
1-[4-(Dimethylamino)butanoyl]-2-[2-(octadecyloxy)ethyl]piperidine

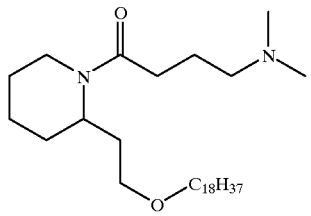

2-(2-Hydroxyethyl)piperidine, HOBt and WSCI are added to N,N-dimethylformamide solution of 4-chlorobutyrate while being cooled with ice and the mixture is reacted at room temperature to obtain 1-(4-(chlorobutanoyl)-2-(2-hydroxyethyl)piperidine.

This compound and 1-bromooctadecane are reacted in acetone in the presence of potassium carbonate at reflux temperature to obtain 1-(4-chlorobutanoyl)-2-[2-(octadecyloxy)ethyl]piperidine.

This compound and dimethylamine are reacted in acetone in the presence of potassium carbonate at reflux temperature to obtain the entitled compound.

Compound 83
2-(1-Octadecanoyl-2-piperidyl)ethyl 3-(dimethylamino)propylcarboxylate

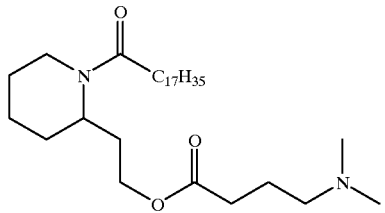

Ethyl chlorocarbonate is added to methylene chloride solution of 4-(N,N-dimethylamino)butyrate in the presence of triethylamine at 0° C. and the mixture is reacted. 1-[2-(2-Hydroxyethyl)piperidino]octadecan-1-one is added to the reaction mixture and the reaction is effected at room temperature to obtain the entitled compound.

Compound 84
2-[2-[1-[4-(Dimethylamino)butanoyl]piperidino]ethyl octadecanoate

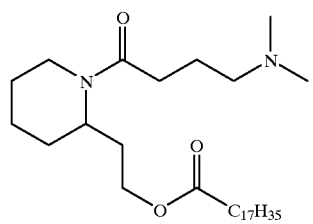

DCC is added to N,N-dimethylformamide solution of 1-[4-(dimethylamino)butanoyl]-2-(2-hydroxyethyl)piperidine obtained in the way of manufacturing Compound 80 and stearic acid, and then the mixture is reacted at room temperature to obtain the entitled compound.

Compound 85
1-Octadecanoyl-2-[2-[3-(dimethylamino)propylamino]ethyl]piperidine

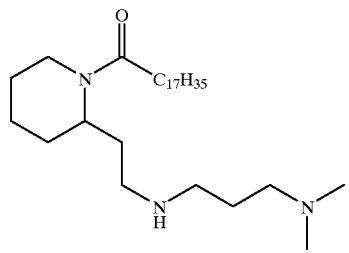

1,4-Dioxane solution of 1-[2-(2-hydroxyethyl)piperidino]octadecan-1-one and p-toluenesulfonyl chloride is added to sodium hydroxide solution and the mixture is reacted at room temperature to obtain 1-octadecanoyl-2-[2-(tosyloxy)ethyl]piperidine.

This compound and N,N-dimethyl-1,3-propanediamine are reacted in acetone in the presence of potassium carbonate at reflux temperature to obtain the entitled compound.

Compound 86
1-[4-(Dimethylamino)butanoyl]-2-[2-(octadecylamino)ethyl]piperidine

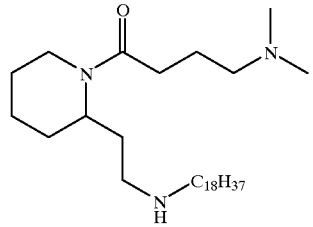

1,4-Dioxane solution of 1-[4-(dimethylamino)butanoyl]-2-(2-hydroxyethyl)-piperidine obtained in the way of manufacturing Compound 80 and p-toluenesulfonyl chloride is added to sodium hydroxide solution and then the mixture is reacted at room temperature to obtain 1-[4-(dimethylamino)butanoyl]-2-[2-(tosyloxy)ethyl]piperidine.

This compound and octadecylamine are reacted in acetone in the presence of potassium carbonate at reflux temperature to obtain the entitled compound.

Compound 87

Octadecyl 2-[2-[N-[2-(morpholino)ethyl]carbamoyloxy]ethyl]piperidinecarboxylate

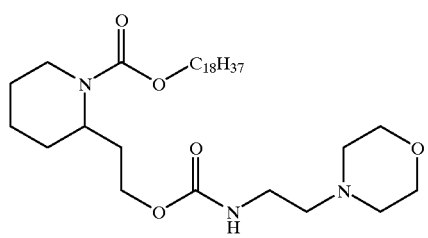

In Example 12 (2), 4-(²-aminoethyl)morpholine is used in the place of N,N-dimethyl-1,3-propanediamine to obtain the entitled compound.

Compound 88

Octadecyl 2-[2-[N-[3-(pyrrolidino)propyl]carbamoyloxy]ethyl]piperidinecarboxylate

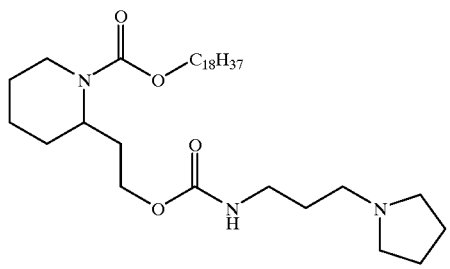

In Example 12 (2), 1-(³-aminopropyl)pyrrolidine is used in the place of N,N-dimethyl-1,3-propanediamine to obtain the entitled compound.

Compound 89

3-(Dimethylamino)propyl 2-[2-(N-octadecylcarbamoyloxy)ethyl]piperidinecarboxylate

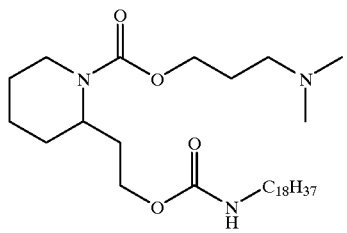

According to the method in Example 1 (2), 3-(dimethylamino)-1-propanol and phenyl chlorocarbonate are reacted in the presence of pyridine. Then, the resulting residue and 2-(2-hydroxyethyl)piperidine are reacted to obtain 3-(dimethylamino)propyl 2-[2-(hydroxyethyl)]piperidinecarboxylate.

In Example 12 (2), this compound and octadecylamine are used in the place of octadecyl 2-(2-hydroxyethyl)piperidinecarboxylate and N,N-dimethyl-1,3-propanediamine, respectively, to obtain the entitled compound.

Compound 90

Octadecyl 2-[2-[4-(dimethylamino)butoxy]ethyl]piperidinecarboxylate

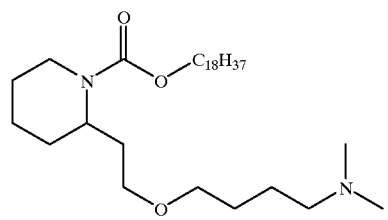

Sodium hydride is added to tetrahydrofuran solution of octadecyl 2-(2-hydroxyethyl)piperidinecarboxylate and the mixture is reacted at 0° C. Then, 1-bromo-4-chlorobutane is added to the reaction mixture and reacted to obtain octadecyl 2-(4-chlorobutoxyethyl)piperidinecarboxylate.

This compound and dimethylamine are reacted in acetone in the presence of potassium carbonate at reflux temperature to obtain the entitled compound.

Compound 91

3-(Dimethylamino)propyl 2-[2-(octadecyloxy)ethyl]piperidinecarboxylate

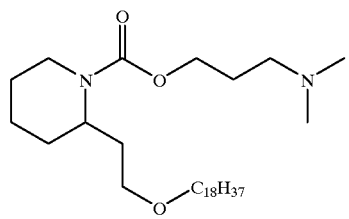

According to the method in Example 1 (2), 3-(chloro)-1-propanol and phenyl chlorocarbonate are reacted. Then, the resulting residue and 2-(2-hydroxyethyl)piperidine are reacted to obtain 3-chloropropyl 2-[2-(hydroxyethyl)]piperidinecarboxylate.

This compound and 1-bromooctadecane are reacted in acetone in the presence of potassium carbonate at reflux temperature to obtain ³-chloropropyl 2-[2-(octadecyloxy)ethyl]piperidinecarboxylate.

This compound and dimethylamine are reacted in acetone in the presence of potassium carbonate at reflux temperature to obtain the entitled compound.

Compound 92

Octadecyl 2-[2-[4-(dimethylamino)butanoyl]ethyl]piperidinecarboxylate

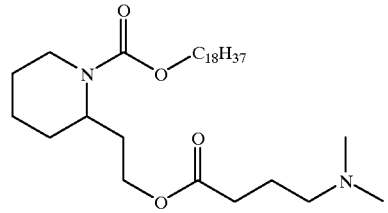

Ethyl chlorocarbonate was added to methylene chloride solution of 4-(dimethylamino)butyrate in the presence of triethylamine at 0° C. and the mixture is reacted. Octadecyl 2-(2-hydroxyethyl)piperidinecarboxylate is added to the reaction mixture and reacted at room temperature to obtain the entitled compound.

Compound 93
3-(Dimethylamino)propyl 2-[2-(octadecanoyloxy)ethyl]piperidinecarboxylate

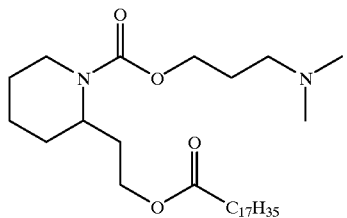

DCC is added to N,N-dimethylformamide solution of 3-(dimethylamino)propyl 2-[2-(hydroxyethyl)]piperidinecarboxylate obtained in the way of manufacturing Compound 89 and stearic acid, and then the mixture is reacted at room temperature to obtain the entitled compound.

Compound 94
Octadecyl 2-[2-[3-(dimethylamino)propylamino]ethyl]piperidinecarboxylate

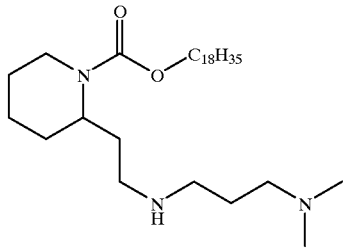

1,4-Dioxane solution of octadecyl 2-(2-hydroxyethyl) piperidinecarboxylate and p-toluenesulfonyl chloride is added to sodium hydroxide solution and the mixture is reacted at room temperature to obtain octadecyl 2-[2-(tosyloxy)ethyl]piperidinecarboxylate.

This compound and N,N-dimethyl-1,3-propanediamine are reacted in acetone in the presence of potassium carbonate at reflux temperature to obtain the entitled compound.

Compound 95
3-(Dimethylamino)propyl 2-[2-(octadecylamino)ethyl]piperidinecarboxylate

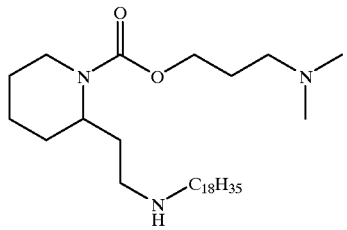

1,4-Dioxane solution of 3-(dimethylamino)propyl 2-[2-(hydroxyethyl)]piperidine carboxylate obtained in the way of manufacturing Compound 89 and p-toluenesulfonyl chloride is added to sodium hydroxide solution and the mixture is reacted at room temperature to obtain 3-(dimethylamino)propyl 2-[2-(tosyloxy)ethyl]piperidinecarboxylate.

This compound and octadecylamine are reacted in acetone in the presence of potassium carbonate at reflux temperature to obtain the entitled compound.

What is claimed is:

1. A 1,2-di-substituted piperidine derivative or a salt thereof expressed by the following Formula (I):

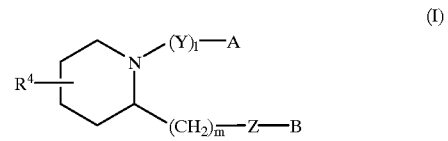

wherein each of A and B is $R^1$ or $—(CH_2)_n—NR^2R^3$, wherein when A is $R^1$, B is $—(CH_2)_n—NR^2R^3$ and when A is $—(CH_2)_n—NR^2R^3$, B is $R^1$;

Y is —CO—, —CONR$^5$— or —COO—;

Z is —O—, —OCO—, —OCONR$^6$— or —NR$^6$—;

$R^1$ is an alkyl group of $C_{10–30}$;

$R^2$ and $R^3$ individually represent a hydrogen atom, a lower alkyl group, a phenyl group or a benzyl group, or together represent a heterocycle having 3–7 members;

wherein when $—(Y)_1—A$ is $—CONR^5—(CH_2)_n—NR^2R^3$, or when $—Z—B$ is $—OCONR^6—(CH_2)_n—NR^2R^3$ or $—NR^6—(CH_2)_n—NR^2R^3$, said $—NR^5—(CH_2)_n—NR^2R^3$ of $—(Y)_1—A$ and said $—NR^6—(CH_2)_n—NR^2R^3$ of $—Z—B$ may be expressed by the following Group W:

wherein ring E is a heterocycle of 6 or 7 members including two nitrogen atoms and $R^2$ is a hydrogen atom, a lower alkyl group, a phenyl group or a benzyl group;

$R^4$ is selected from the group consisting of a hydrogen atom, a halogen atom, a lower alkyl group, a lower acyl group, a nitro group, a cyano group, a lower alkoxycarbonyl group, a carbamoyl group, a lower alkylcarbamoyl group, a lower alkylamino group, a lower acylamino group, a lower alkoxy group and a lower acyloxy group;

$R^5$ is a hydrogen atom, a lower alkyl group, a lower acyl group or a lower alkylcarbamoyl group; wherein when $—(Y)_1—A$ is $—CONR^5—(CH_2)_n—NR^2R^3$, $—(Y)_1—A$ may be —CO—W;

$R^6$ is a hydrogen atom, a lower alkyl group, a lower acyl group or a lower alkylcarbamoyl group; wherein when $—Z—B$ is $—OCONR^6—(CH_2)_n—NR^2R^3$ or $—NR^6—(CH_2)_n—NR^2R^3$, $—Z—B$ may be —OCO—W or said Group W;

l is 0 or 1;

m is an integer of 2–5; and n is an integer of 0–5.

2. A 1,2-di-substituted piperidine derivative or a salt thereof expressed by the following formula (I):

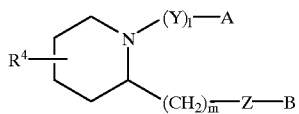

wherein each of A and B is $R^1$ or $-(CH_2)_n-NR^2R^3$, wherein when A is $R^1$, B is $-(CH_2)_n-NR^2R^3$ and when A is $-(CH_2)_n-NR^2R^3$, B is $R^1$;

Y is —CO—;

Z is —O—, —OCO— or —OCONR$^6$—;

$R^1$ is a hydrocarbon group of $C_{1-30}$;

$R^2$ and $R^3$ individually represent a hydrogen atom, a lower alkyl group, a phenyl group or a benzyl group, or together represent a heterocycle having 3–7 members;

wherein when —Z—B is —OCONR$^6$—(CH$_2$)$_n$—NR$^2$R$^3$, said —NR$^6$—(CH$_2$)$_n$—NR$^2$R$^3$ of —Z—B may be expressed by the following Group W:

wherein ring E is a heterocycle of 6 or 7 members including two nitrogen atoms and $R^2$ is a hydrogen atom, a lower alkyl group, a phenyl group or a benzyl group;

$R^4$ is selected from the group consisting of a hydrogen atom, a halogen atom, a lower alkyl group, a lower acyl group, a nitro group, a cyano group, a lower alkoxycarbonyl group, a carbamoyl group, a lower alkylcarbamoyl group, a lower alkylamino group, a lower acylamino group, a lower alkoxy group and a lower acyloxy group;

$R^6$ is a hydrogen atom, a lower alkyl group, a lower acyl group or a lower alkylcarbamoyl group; wherein when —Z—B is —OCONR$^6$—(CH$_2$)$_n$— NR$^2$R$^3$, —Z—B may be —OCO—W;

l is 1;

m is an integer of 2–5; and n is an integer of 0–5.

3. A 1,2-di-substituted piperidine derivative or a salt thereof expressed by the following formula (I):

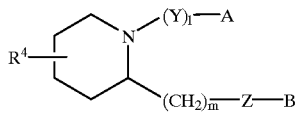

wherein each of A and B is $R^1$ or $-(CH_2)_n-NR^2R^3$, wherein when A is $R^1$, B is $-(CH_2)_n-NR^2R^3$ and when A is $-(CH_2)_n-NR^2R^3$, B is $R^1$;

Y is —CONR$^5$—;

Z is —O—, —OCO— or —OCONR$^6$—;

$R^1$ is a hydrocarbon group of $C_{1-30}$;

$R^2$ and $R^3$ individually represent a hydrogen atom, a lower alkyl group, a phenyl group or a benzyl group, or together represent a heterocycle having 3–7 members;

wherein when —(Y)$_l$—A is —CONR$^5$—(CH$_2$)$_n$—NR$^2$R$^3$, or when —Z—B is —OCONR$^6$—(CH$_2$)$_n$—NR$^2$R$^3$, said —NR$^5$—(CH$_2$)$_n$—NR$^2$R$^3$ of —(Y)$_l$—A and said —NR$^6$—(CH$_2$)$_n$—NR$^2$R$^3$ of —Z—B may be expressed by the following Group W:

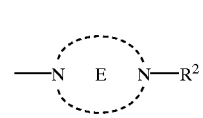

wherein ring E is a heterocycle of 6 or 7 members including two nitrogen atoms and $R^2$ is a hydrogen atom, a lower alkyl group, a phenyl group or a benzyl group;

$R^4$ is selected from the group consisting of a hydrogen atom, a halogen atom, a lower alkyl group, a lower acyl group, a nitro group, a cyano group, a lower alkoxycarbonyl group, a carbamoyl group, a lower alkylcarbamoyl group, a lower alkylamino group, a lower acylamino group, a lower alkoxy group and a lower acyloxy group;

$R^5$ is a hydrogen atom, a lower alkyl group, a lower acyl group or a lower alkylcarbamoyl group; wherein when —(Y)$_l$—A is —CONR$^5$—(CH$_2$)$_n$—NR$^2$R$^3$, —(Y)$_l$—A may be —CO—W;

$R^6$ is a hydrogen atom, a lower alkyl group, a lower acyl group or a lower alkylcarbamoyl group; wherein when —Z—B is —OCONR$^6$—(CH$_2$)$_n$—NR$^2$R$^3$, —Z—B may be —OCO—W;

l is 1;

m is an integer of 2–5; and n is an integer of 0–5.

4. A 1,2-di-substituted piperidine derivative or a salt thereof expressed by the following formula (I):

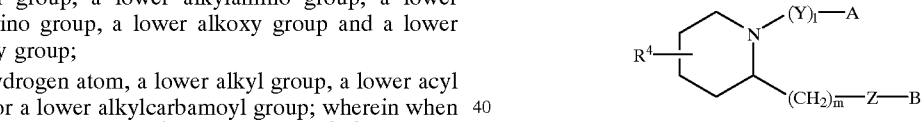

wherein each of A and B is $R^1$ or $-(CH_2)_n-NR^2R^3$, wherein when A is $R^1$, B is $-(CH_2)_n-NR^2R^3$ and when A is $-(CH_2)_n-NR^2R^3$, B is $R^1$;

Y is —COO—;

Z is —O—, —OCO—, —OCONR$^6$— or —NR$^6$—;

$R^1$ is a hydrocarbon group of $C_{1-30}$;

$R^2$ and $R^3$ individually represent a hydrogen atom, a lower alkyl group, a phenyl group or a benzyl group, or together represent a heterocycle having 3–7 members;

wherein when —Z—B is —OCONR$^6$—(CH$_2$)$_n$—NR$^2$R$^3$ or —NR$^6$—(CH$_2$)$_n$—NR$^2$R$^3$, said —NR$^6$—(CH$_2$)$_n$—NR$^2$R$^3$ of —Z—B may be expressed by the following Group W:

wherein ring E is a heterocycle of 6 or 7 members including two nitrogen atoms and $R^2$ is a hydrogen atom, a lower alkyl group, a phenyl group or a benzyl group;

$R^4$ is selected from the group consisting of a hydrogen atom, a halogen atom, a lower alkyl group, a lower acyl group, a nitro group, a cyano group, a lower alkoxycarbonyl group, a carbamoyl group, a lower alkylcarbamoyl group, a lower alkylamino group, a lower acylamino group, a lower alkoxy group and a lower acyloxy group;

$R^6$ is a hydrogen atom, a lower alkyl group, a lower acyl group or a lower alkylcarbamoyl group; wherein when —Z—B is —OCONR$^6$—(CH$_2$)$_n$—NR$^2$R$^3$ or —NR$^6$—(CH$_2$)$_n$—NR$^2$R$^3$, —Z—B may be —OCO—W or said group W;

l is 1;

m is an integer of 2–5; and n is an integer of 0–5.

5. A 1,2-di-substituted piperidine derivative or a salt thereof expressed by the following formula (I):

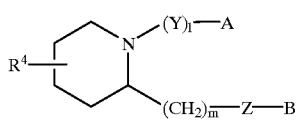

wherein:

A is $R^1$;

B is —(CH$_2$)$_n$—NR$^2$R$^3$;

Y is —CO—, —CONR$^5$— or —COO—;

Z is —O—, —OCO—, —OCONR$^6$— or —NR$^6$—;

$R^1$ is a hydrocarbon group of $C_{1-30}$;

$R^2$ and $R^3$ individually represent a hydrogen atom, a lower alkyl group, a phenyl group or a benzyl group, or together represent a heterocycle having 3–7 members;

wherein when —Z—B is —OCONR$^6$—(CH$_2$)$_n$—NR$^2$R$^3$ or —NR$^6$—(CH$_2$)$_n$—NR$^2$R$^3$, said —NR$^6$—(CH$_2$)$_n$—NR$^2$R$^3$ of —Z—B may be expressed by the following Group W:

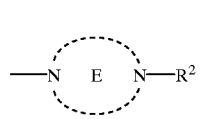

wherein ring E is a heterocycle of 6 or 7 members including two nitrogen atoms and $R^2$ is a hydrogen atom, a lower alkyl group, a phenyl group or a benzyl group;

$R^4$ is selected from the group consisting of a hydrogen atom, a halogen atom, a lower alkyl group, a lower acyl group, a nitro group, a cyano group, a lower alkoxycarbonyl group, a carbamoyl group, a lower alkylcarbamoyl group, a lower alkylamino group, a lower acylamino group, a lower alkoxy group and a lower acyloxy group;

$R^5$ is a hydrogen atom, a lower alkyl group, a lower acyl group or a lower alkylcarbamoyl group;

$R^6$ is a hydrogen atom, a lower alkyl group, a lower acyl group or a lower alkylcarbamoyl group; wherein when —Z—B is —OCONR$^6$—(CH$_2$)$_n$—NR$^2$R$^3$ or —NR$^6$—(CH$_2$)$_n$—NR$^2$R$^3$, —Z—B may be —OCO—W or said Group W;

l is 0 or 1;

m is an integer of 2–5; and n is an integer of 0–5;

wherein when l=0, Z is —OCONR$^6$—, —OCO— or —NR$^6$—;

wherein when —(Y)$_1$—=—CONR$^5$— or —CO—, Z is —OCONR$^6$—, —O—, or —OCO—.

6. A 1,2-di-substituted piperidine derivative or a salt thereof expressed by the following formula (I):

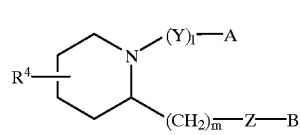

wherein each of A and B is $R^1$ or —(CH$_2$)$_n$—NR$^2$R$^3$, wherein when A is $R^1$, B is —(CH$_2$)$_n$—NR$^2$R$^3$ and when A is —(CH$_2$)$_n$—NR$^2$R$^3$, B is $R^1$;

Y is —CO—, —CONR$^5$— or —COO—;

Z is —OCONR$^6$—;

$R^1$ is a hydrocarbon group of $C_{1-30}$;

$R^2$ and $R^3$ individually represent a hydrogen atom, a lower alkyl group, a phenyl group or a benzyl group, or together represent a heterocycle having 3–7 members;

wherein when —(Y)$_1$—A is —CONR$^5$—(CH$_2$)$_n$—NR$^2$R$^3$, or when —Z—B is —OCONR$^6$—(CH$_2$)$_n$—NR$^2$R$^3$, said —NR$^5$—(CH$_2$)$_n$—NR$^2$R$^3$ of —(Y)$_1$—A and said —NR$^6$—(CH$_2$)$_n$—NR$^2$R$^3$ of —Z—B may be expressed by the following Group W:

wherein ring E is a heterocycle of 6 or 7 members including two nitrogen atoms and $R^2$ is a hydrogen atom, a lower alkyl group, a phenyl group or a benzyl group;

$R^4$ is selected from the group consisting of a hydrogen atom, a halogen atom, a lower alkyl group, a lower acyl group, a nitro group, a cyano group, a lower alkoxycarbonyl group, a carbamoyl group, a lower alkylcarbamoyl group, a lower alkylamino group, a lower acylamino group, a lower alkoxy group and a lower acyloxy group;

$R^5$ is a hydrogen atom, a lower alkyl group, a lower acyl group or a lower alkylcarbamoyl group; wherein when —(Y)$_1$—A is —CONR$^5$—(CH$_2$)$_n$NR$^2$R$^3$, —(Y)$_1$—A may be —CO—W;

$R^6$ is a hydrogen atom, a lower alkyl group, a lower acyl group or a lower alkylcarbamoyl group; wherein when —Z—B is —OCONR$^6$—(CH$_2$)$_n$—NR$^2$R$^3$, —Z—B may be —OCO—W;

l is 0 or 1;

m is an integer of 2–5; and n is an integer of 0–5.

7. A 1,2-di-substituted piperidine derivative or a salt thereof according to claim 1, wherein when l=0, Z is —OCONR$^6$—, —OCO—, or —NR$^6$—; and wherein when —(Y)$_1$—=—CONR$^5$— or —CO—, Z is —OCONR$^6$—, —O—, or —OCO—.

8. A 1,2-di-substituted piperidine derivative or a salt thereof according to claim 3, wherein $R^5$ is a hydrogen atom.

9. A 1,2-di-substituted piperidine derivative or a salt thereof according to claim 6, wherein $R^6$ is a hydrogen atom.

10. A 1,2-di-substituted piperidine derivative or a salt thereof according to claim 6, which is expressed by the following Formula (IA):

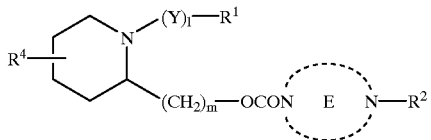

(IA)

wherein ring E is a heterocycle of 6 or 7 members including two nitrogen atoms;

$R^1$ is a hydrocarbon group of $C_{1-30}$;

$R^2$ is a hydrogen atom, a lower alkyl group, a phenyl group or a benzyl group;

$R^4$ is selected from the group consisting of a hydrogen atom, a halogen atom, a lower alkyl group, a lower acyl group, a nitro group, a cyano group, a lower alkoxycarbonyl group, a carbamoyl group, a lower alkylcarbamoyl group, a lower alkylamino group, a lower acylamino group, a lower alkoxy group and a lower acyloxy group;

Y is —CO—, —CONR⁵— or —COO—;

l is 0 or 1; and m is an integer of 2–5.

11. A 1,2-di-substituted piperidine derivative or a salt thereof according to claim 10, wherein l is 1 and Y is —CO—.

12. A 1,2-di-substituted piperidine derivative or a salt thereof according to claim 1, wherein $R^4$ is a hydrogen atom.

13. A 1,2-di-substituted piperidine derivative or a salt thereof according to claim 1, wherein m is 2.

14. A 1,2-di-substituted piperidine derivative or a salt thereof according to claim 1, wherein n is an integer of 2–5.

15. A hair growth promoting composition comprising an effective amount of an 1,2-di-substituted piperidine derivative or the pharmacologically acceptable salt thereof expressed by the following formula (I):

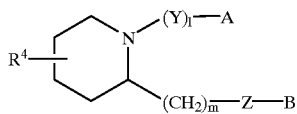

(I)

wherein each of A and B is $R^1$ or —(CH₂)ₙ—NR²R³, wherein when A is $R^1$, B is —(CH₂)ₙ—NR²R³ and when A is —(CH₂)ₙ—NR²R³, B is $R^1$;

Y is —CO—, —CONR⁵— or —COO—;

Z is —O—, —OCO—, —OCONR⁶— or —NR⁶—;

$R^1$ is a hydrocarbon group of $C_{1-30}$;

$R^2$ and $R^3$ individually represent a hydrogen atom, a lower alkyl group, a phenyl group or a benzyl group, or together represent a heterocycle having 3–7 members;

wherein when —(Y)₁—A is —CONR⁵—(CH₂)ₙ—NR²R³, or when —Z—B is —OCONR⁶—(CH₂)ₙ—NR²R³ or —NR⁶—(CH₂)ₙ—NR²R³, said —NR⁵—(CH₂)ₙ—NR²R³ of —(Y)₁—A and said —NR⁶—(CH₂)ₙ—NR²R³ of —Z—B may be expressed by the following Group W:

(W)

wherein ring E is a heterocycle of 6 or 7 members including two nitrogen atoms and $R^2$ is a hydrogen atom, a lower alkyl group, a phenyl group or a benzyl group;

$R^4$ is selected from the group consisting of a hydrogen atom, a halogen atom, a lower alkyl group, a lower acyl group, a nitro group, a cyano group, a lower alkoxycarbonyl group, a carbamoyl group, a lower alkylcarbamoyl group, a lower alkylamino group, a lower acylamino group, a lower alkoxy group and a lower acyloxy group;

$R_5$ is a hydrogen atom, a lower alkyl group, a lower acyl group or a lower alkylcarbamoyl group; wherein when —(Y)₁—A is —CONR⁵—(CH₂)ₙ—NR²R³, —(Y)₁—A may be —CO—W;

$R^6$ is a hydrogen atom, a lower alkyl group, a lower acyl group or a lower alkylcarbamoyl group; wherein when —Z—B is —OCONR⁶—(CH₂)ₙ—NR²R³ or —NR⁶—(CH₂)ₙ—NR²R³, —Z—B may be —OCO—W or said Group W;

l is 0 or 1;

m is an integer of 2–5; and n is an integer of 0–5.

16. An external preparation for skin comprising an 1,2-di-substituted piperidine derivative or the pharmacologically acceptable salt thereof expressed by the following formula (I):

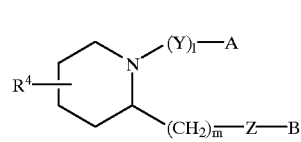

(I)

wherein each of A and B is $R^1$ or —(CH₂)ₙ—NR²R³, wherein when A is $R^1$, B is —(CH₂)ₙ—NR²R³ and when A is —(CH₂)ₙ—NR²R³, B is $R^1$;

Y is —CO—, —CONR⁵— or —COO—;

Z is —O—, —OCO—, —OCONR⁶— or —NR⁶—;

$R^1$ is a hydrocarbon group of $C_{1-30}$;

$R^2$ and $R^3$ individually represent a hydrogen atom, a lower alkyl group, a phenyl group or a benzyl group, or together represent a heterocycle having 3–7 members;

wherein when —(Y)₁—A is —CONR⁵—(CH₂)ₙ—NR²R³, or when —Z—B is —OCONR⁶—(CH₂)ₙ—NR²R³ or —NR⁶—(CH₂)ₙ—NR²R³, said —NR⁵—(CH₂)ₙ—NR²R³ of —(Y)₁—A and said —NR⁶—(CH₂)ₙ—NR²R³ of —Z—B may be expressed by the following Group W:

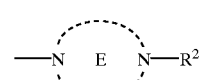

(W)

wherein ring E is a heterocycle of 6 or 7 members including two nitrogen atoms and $R^2$ is a hydrogen atom, a lower alkyl group, a phenyl group or a benzyl group;

R[4] is selected from the group consisting of a hydrogen atom, a halogen atom, a lower alkyl group, a lower acyl group, a nitro group, a cyano group, a lower alkoxycarbonyl group, a carbamoyl group, a lower alkylcarbamoyl group, a lower alkylamino group, a lower acylamino group, a lower alkoxy group and a lower acyloxy group;

R[5] is a hydrogen atom, a lower alkyl group, a lower acyl group or a lower alkylcarbamoyl group, wherein when $-(Y)_1-A$ is $-CONR^5-(CH_2)_n-NR^2R^3$, $-(Y)_1-A$ may be $-CO-W$;

R[6] is a hydrogen atom, a lower alkyl group, a lower acyl group or a lower alkylcarbamoyl group; wherein when $-Z-B$ is $-OCONR^6-(CH_2)_n-NR^2R^3$ or $-NR^6-(CH_2)_n-NR^2R^3$, $-Z-B$ may be $-OCO-W$ or said Group W;

l is 0 or 1;
m is an integer of 2–5; and
n is an integer of 0–5.

17. A method for promoting hair growth, which comprises:
applying on skin of mammals an effective amount of an 1,2-di-substituted piperidine derivative or the pharmacologically acceptable salt thereof expressed by the following formula (I):

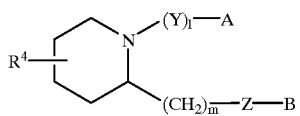

wherein each of A and B is R[1] or $-(CH_2)_n-NR^2R^3$, wherein when A is R[1], B is $-(CH_2)_n-NR^2R^3$ and when A is $-(CH_2)_n-NR^2R^3$, B is R[1];

Y is $-CO-$, $-CONR^5-$ or $-COO-$;
Z is $-O-$, $-OCO-$, $-OCONR^6-$ or $-NR^6-$;
R[1] is a hydrocarbon group of $C_{1-30}$,
R[2] and R[3] individually represent a hydrogen atom, a lower alkyl group, a phenyl group or a benzyl group, or together represent a heterocycle having 3–7 members;

wherein when $-(Y)_1-A$ is $-CONR^5-(CH_2)_n-NR^2R^3$, or when $-Z-B$ is $-OCONR^6-(CH_2)_n-NR^2R^3$, or $-NR^6-(CH_2)_n-NR^2R^3$, said $-NR^5-(CH_2)_n-NR^2R^3$ of $-(Y)_1-A$ and said $-NR^6-(CH_2)_n-NR^2R^3$ of $-Z-B$ may be expressed by the following Group W:

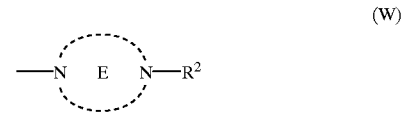

wherein ring E is a heterocycle of 6 or 7 members including two nitrogen atoms and R[2] is a hydrogen atom, a lower alkyl group, a phenyl group or a benzyl group;

R[4] is selected from the group consisting of a hydrogen atom, a halogen atom, a lower alkyl group, a lower acyl group, a nitro group, a cyano group, a lower alkoxycarbonyl group, a carbamoyl group, a lower alkylcarbamoyl group, a lower alkylamino group, a lower acylamino group, a lower alkoxy group and a lower acyloxy group;

R[5] is a hydrogen atom, a lower alkyl group, a lower acyl group or a lower alkylcarbamoyl group; wherein when $-(Y)_1-A$ is $-CONR^5-(CH_2)_n-NR^2R^3$, $-(Y)_1-A$ may be $-CO-W$;

R[6] is a hydrogen atom, a lower alkyl group, a lower acyl group or a lower alkylcarbamoyl group; wherein when $-Z-B$ is $-OCONR^6-(CH_2)_n-NR^2R^3$ or $-NR^6-(CH_2)_n-NR^2R^3$, $-Z-B$ may be $-OCO-W$ or said Group W;

l is 0 or 1;
m is an integer of 2–5; and
n is an integer of 0–5.

18. A method for promoting hair growth according to claim 17, wherein the skin of mammals is human scalp.

* * * * *